US008168207B2

(12) United States Patent
Chang et al.

(10) Patent No.: US 8,168,207 B2
(45) Date of Patent: May 1, 2012

(54) **IMMUNOGENIC PROTEINS OF *LEPTOSPIRA***

(75) Inventors: Yung-Fu Chang, Ithaca, NY (US); Raghavan U. M. Palaniappan, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 519 days.

(21) Appl. No.: 12/259,782

(22) Filed: Oct. 28, 2008

(65) Prior Publication Data

US 2011/0110966 A1 May 12, 2011

Related U.S. Application Data

(60) Division of application No. 11/102,476, filed on Apr. 8, 2005, now Pat. No. 7,655,427, which is a continuation of application No. PCT/US03/032385, filed on Oct. 10, 2003.

(60) Provisional application No. 60/417,721, filed on Oct. 10, 2002.

(51) Int. Cl.
*A61K 39/002* (2006.01)

(52) U.S. Cl. .................. 424/269.1; 424/234.1; 530/300; 530/350

(58) Field of Classification Search ........................ None
See application file for complete search history.

(56) References Cited

U.S. PATENT DOCUMENTS

2004/0058323 A1 3/2004 Ko et al.

FOREIGN PATENT DOCUMENTS

WO 03/098214 A1 11/2003

OTHER PUBLICATIONS

Greenspan et al (Nature Biotechnology 7: 936-937, 1999).*
Chothia et al (The EMBO Journal, 1986, 5/4:823-26).*
Jusuf et al., "Leptospira Interrogans Surface Protein LK90 (LK90) Gene, Complete Cds," GenEmbl Database, Accession No. U95056, 3 p. (1997).
Jusuf et al., "Surface Protein Lk90," GenEmbl Database, Accession No. O05734, 2 p. (1997).
Palaniappan et al., "Cloning and Characterization of a LigB Protein of Leptospira Interrogans," GenEmbl Database, Accession No. Q7X2A1, 3 p. (2002).
Palaniappan et al., "Cloning and Molecular Characterization of an Immunogenic LigA Protein of Leptospira Interrogans," Infection and Immunity, 70:5924-5930 (2002).
Palaniappan et al., "Leptospira Interrogans Serovar Pomona Immunoglobulins-like B Protein Gene, Complete cds," GemEmbl Database, Accession No. AF534640, 5 pg. (2002).
Ren et al., "Leptospira Interrogans Serovar Lai Str. 566601 Chromosomes I, Section 342 of 397 of the Complete Sequence," GenEmbl Database, Accession No. ae011533, 2p. (2002).
Ren et al., "Surface Protein LK90-Like Protein," GenEmbl Database, Accession Nos. Q8EZS3 & Q8F124, 4 p. (2002).

* cited by examiner

*Primary Examiner* — Jennifer Graser
(74) *Attorney, Agent, or Firm* — LeClairRyan, a Professional Corporation

(57) ABSTRACT

The invention provides novel immunogenic proteins LigA and LigB from *Leptospira* for use in the development of effective vaccines and antibodies, as well as improved diagnostic methods and kits.

14 Claims, 27 Drawing Sheets

```
TAACTTGGTTCTCCTCCAATCCTTCTAGTGTTGTAATTGAAAAACACTCCCGGCAAAAAGGTCTCGCGTTCG   3384
 V  T  W  F  S  S  N  P  S  S  V  I  E  N  T  P  G  K  K  G  L  A  F
CTTCTGAATTAGGAGAACCCGACATTACGGTATTCTACGATCACACTCCAGAGTTCTTATACTCCAGTTA    3456
 A  S  E  L  G  E  P  D  I  T  V  F  Y  D  H  H  T  Q  S  Y  T  P  V
CGGTTACGGGAAGTGGTATAGTAAATATCACTATTAGTCTTTCCATTTCGAAAAACAAAGGTTCAACCC     3528
 T  V  T  E  S  G  I  V  N  I  T  I  S  L  S  S  I  S  K  T  K  G  S  T
ATCAATTAAAGCTACCGGAAAGTTTGAGAATGGTGCCGAAATAGATCTCACTGAACTTGTAACTTGGAGTT   3600
 H  Q  F  K  A  T  G  K  F  E  N  G  A  E  I  D  L  T  E  L  V  T  W  S
CTTCCAATCCTACGGTGGTTTCTATTAGCAATGTGATGACGAAAGAGGTTTGGCAACTGCTCTTTCCGTAG   3672
 S  S  N  P  T  V  V  S  I  S  N  V  D  D  E  R  G  L  A  T  A  L  S  V
GTTCCTCCAAAATATCTGTAGATTACAATTCTATCAGTAGCTCTATCGATTTTGAAGTAACTCCAGAAATAT  3744
 G  S  S  K  I  S  V  D  Y  N  S  I  S  S  I  D  F  E  V  T  P  E  I
TAGCCTCTATTAAAACGGAGCCATAAACATGAAAACATTAACAATGTTTACACATTCGCAAAAAACAAACAAT 3816
 L  A  S  I  K  T  E  P
GAGTTCGTGACCTTTCTTTATTACGAATTCATTGAGTTATTGAATAACGCCGATTTTATGGAAAAGGAGCA   3888
ACTCAAGTTTATCGGTATGATTGTAACCTTGTGACCCTTGTGATCGTTCTTCTTCCTAACTTTTGTTCCT    3960
AAAAACACGCCCGCAGATTCTGCCGGAGTGTTTTT                                       3993
```

```
ACAGCAAATACACAAATGAAAACTTCAAATAAATAAACAGCAAATACACAAATGAAAACTTTAAATAA      72
AACAATTAGAGTGAGTGTTTATGAAGAAAAATATTTGTATTTCGATTTTTCTTTCGATGTTTTTCAAGTT    144
                    M  K  K  I  F  C  I  S  I  F  L  S  M  F  F  Q  G
GTATGTCTTGGCCACTTTTAAGGTAATTAACCGGTCTGGTAGGATAACCGCTGGTAAAAAAGTAATGGGCTGTCCTTTT  216
 C  M  S  W  P  L  L  T  G  L  V  G  L  T  A  G  K  K  S  N  G  L  S  F
TCCACCTTCTGTTAGGTAACTCCTAATCCGACTATTACGAAGAATCGAACTCAGTTATCAAGATTCGTCTATCG      288
 F  H  L  L  G  N  S  N  P  T  I  T  R  I  E  L  S  Y  Q  D  S  S  I
CAAACGGTACCAGTACAACCCTAGAAGTTACGCCGATTCCCAATCTTTGATAACGGAACAAATCAGAATATTACGGATT   360
 A  N  G  T  S  T  L  E  V  T  A  I  F  D  N  G  T  N  Q  N  I  T  D
CGACATCCATCGTCGTCCCCGATTCCCAATCCGTTGTAACCAAGGTAACAGAGTCAGGAGAATCGCTTCTG     432
 S  T  S  I  V  P  D  S  Q  S  V  V  T  I  Q  N  R  V  R  G  I  A  S
GTTCTTCCATTATAAAGCAGAATATAACGGCCTGTACTCTGAAACAAAAATTACAGTTACACCAGCCACTC    504
 G  S  S  I  K  A  E  Y  N  G  L  Y  S  E  Q  K  I  T  V  T  P  A  T
TTAACTCAATTCAAGTTACGAGTTTAGAGTCAGGTATACTTCCTAAAGTACTAAGTACTGTCAATTCTCAGCCA    576
 L  N  S  I  Q  V  T  S  L  E  S  G  I  L  P  K  G  T  N  R  Q  F  S  A
TCGGTATCTTTTCGGATGGTTCTCATCAGGATATTTCCAACGATCCATTGATCGTTTGGTCCTCCCAGTAATC    648
 I  G  I  F  S  D  G  S  H  Q  D  I  S  N  D  P  L  I  V  W  S  S  N
CTGATTTGGTAGCAAGTAGATGATTCAGGGCTCAATTTAGGAACAGCTCATATTCGTGCAT      720
 L  I  F  S  G  L  A  S  G  I  N  L  G  T  A  H  I  R  A
CCTTTCAATCAAAACAAGGGGCTGAAGAAATGACCGTTGGAGATGCTGTCTTCTCAAATCCAAGTAACTT     792
 P  D  L  V  Q  V  D  D  S  K  Q  G  A  E  E  M  T  V  G  D  A  V  L  S  Q  I  Q  V  T
CAAACAATCCGAATATTCCTCTCGGAAAAACAAAACTTGCTACCACTATCAGATAACTCTA      864
 S  F  Q  S  K  Q  G  A  E  E  M  T  V  G  D  A  V  L  S  Q  I  Q  V  T
ACAGGGATATTCCCTCTTCTGTTATCTGGAATTCTGCTTCACTATTCCTAATTCCACTATGCTAATATTCAAAACAACGAA    936
 N  R  D  I  S  S  V  I  W  N  S  S  N  S  T  I  A  N  I  Q  N  G
TATTAGAAACAGCTGATACTGGTATTGTCACTATTTCTTCTGCTTCTAGCGAGAATATAATAGGCTCCGTAAAC   1008
 I  L  E  T  A  D  T  G  I  V  T  I  S  A  S  E  N  I  I  G  S  V  K
TAATCGTTACTCCAGCAGCCTTAGTTTCTGTTTCTATTTCGTATTACAGATAATCAAACTCGGATATTACCGACATATTAC   1080
 L  V  T  P  A  A  L  V  S  I  S  V  S  P  T  N  S  T  V  A  K  G  L
AAGAAAACTTTAAGGCTACAGGGATCTTTACAGATAATTCAAACTCGGATATTACCGACATATTGG       1152
 Q  E  N  F  K  A  T  G  I  F  T  D  N  S  N  S  D  I  T  D  Q  V  T  W
```

Fig.8A

```
ATTCTTCTAATACCGATATATTCTCTCAATTTCCAATGCAAGTGATAGCCACGGGTTAGCTTCCACACTCAACC      1224
 D   S   S   N   T   D   I   L   S   I   S   N   A   S   D   S   H   G   L   A   S   T   L   N
AAGGGAATGTTAAAGTCACTGCTTCCATCGGTGGAATACAAGGATCCACTGATTTTACAGTTACACAAGCTG      1296
 Q   G   N   V   K   V   T   A   S   I   G   G   I   Q   G   S   T   D   F   T   V   T   Q   A
CTTTGACTTCGATCGAAGTCTCTCCAGTTTTACCTTGCAAAAGGACTAACTTGAATTCACTTCTTCAGCAATCG      1368
 A   L   T   S   I   E   V   S   P   V   L   P   S   I   A   K   G   L   T   Q   K   F   T   A
TCGGGATTTTTACGGATAATTCTAAAAAGGATATTACGGATCAAGTCACTTGGAATTCACTTCTTCAGCAATCG      1440
 I   G   I   F   T   D   N   S   K   K   D   I   T   D   Q   V   T   W   N   S   S   S   A   I
TAAGCGTGTCTAACTTAGACGACAATAAAGGTCTGGGAAAAGCTCACGCTGTTGGAGACACGACTATTACCG      1512
 V   S   V   S   N   L   D   D   N   K   G   L   G   K   A   H   A   V   G   D   T   T   I   T
CAACCTTAGGAAAAAGTTTCAGGTAAAACTTGGCTTAACTCAAAAAATTTTCTCCTACAGGATCTACTCTGACAACT      1584
 A   T   L   G   K   V   S   G   K   T   W   L   T   V   P   A   V   L   T   S   I   Q   I
ATCCTGTAAATCCTTCTCTTGCAAAAGGTTTACGTGGTTACGCCGTTCTTCATCCGATTCTTCAAACGCCC      1656
 N   P   V   N   P   S   L   A   K   G   L   T   Q   K   F   S   A   T   G   I   Y   S   D   N
CTAACAAGGACATCACTTCCCGTTCTACGGACAGCAGCCTTACAGGCTGCAAAGTCACTGGTATCTTTACAGAGCC      1728
 S   N   K   D   I   T   S   A   V   T   W   F   S   S   D   S   S   I   A   T   I   S   N   A
AAAAAATCAAGGAAACGCTTATCTGTTACAGGATCAGCAGCCTTACAGGCTGCAAAGTCACTGGTATCTTTACAGAGCC      1800
 Q   K   N   Q   G   N   A   Y   G   A   A   T   C   A   T   D   I   K   A   T   F   G   K   V
GTAGTCCGGTTTCTACCTTGTCTACACCGCAAAAGATTCAAGGCTACTGGTATCTTTACAGAATTCGATATTA      1872
 S   S   P   V   S   T   L   S   V   T   A   A   K   L   V   E   I   Q   I   T   P   A   A   A
CCAAAGCAAAAGGACTCACAGAAGATTCCTAATACGGATATTGCTGAAATTACAAATACCAGTGAAGTAAAGGTA      1944
 S   K   A   K   G   L   T   E   R   F   K   A   T   G   I   F   T   D   N   S   N   D   I
CAAATCAGGTTACTTGGAATTCCTCTAATACGGATATTGCTGAAATTACAAATACCAGTGAAGTAAAGGTA      2016
 T   N   Q   V   T   W   N   S   S   N   T   D   I   A   E   I   T   N   T   S   G   S   K   G
TTACAACCACACACTCACCCAGGATCGAATCATTCAAGATCCATTGATTGATTTGCCTAACACCTATAAAATCGTTAAAGGTC      2088
 I   T   N   T   L   T   P   G   S   S   E   I   S   A   L   G   S   I   K   S   K   V
TTTTAAAGTAACTCCGGCACACTTGATTGATTGATTTGCCTAACACCTATAAAATCGTTAAAGGTC      2160
 I   L   K   V   T   P   A   Q   L   I   S   I   A   V   T   P   I   N   P   S   V   A   K   G
TAATACGACAATTTAAAGCCCAATCCCAGGAACATATACGGATCATTCCGAAGACGTTACAACAGTGGCTACCT      2232
 L   I   R   Q   F   K   A   T   G   I   Y   T   D   H   S   V   Q   D   V   T   A   L   A   T
GGTCTCTTCCAATCCCAGAAAAGCAATGGTTACAACGTTCGGTTACAACAGTGGCTACCGGAA      2304
 W   S   S   S   N   P   R   K   A   M   V   N   N   V   T   G   S   V   T   T   V   A   T   G
```

*Fig. 8B*

```
ATACAAATATTAAAGCAACGATAGACTCCATATCCGGCTCTTCCGTTTTGAATGTCACTCCTGCACTTCTTA   2376
 N   T   N   I   K   A   T   I   D   S   I   S   G   S   S   V   L   N   V   T   P   A   L   L
CTTCTATCGAGATAACACCGACGATTAACTCTATCACTCACGGTCTTACAAAACAATTTAAAGCGACTGGTA   2448
 T   S   I   E   I   T   P   T   I   N   S   I   T   H   G   L   T   K   Q   F   K   A   T   G
TCTTTTCAGATAAATCTACTCAAATTGACTCAGCTTGTAACTTGGATTTCTTCCGATCCATCTAAGATTG    2520
 I   F   S   D   K   S   T   Q   N   L   T   Q   L   V   T   W   I   S   S   D   P   S   K   I
AGATCGAAAAACACTTCCGGTAAAAAAGGTATAGCGACAGCCTCTAAATTAGGAAGTTCGAATATTAAGCCG   2592
 E   I   E   N   T   S   G   K   K   G   I   A   T   A   S   K   L   G   S   S   N   I   K   A
TCTACAAATTCATCCAAAGCTCCCCCAATTCCAGATTACAGTGACTTAAAACTGAAAAGTATAACTATCA    2664
 V   Y   K   F   I   Q   S   S   P   I   P   I   T   V   T   D   L   K   L   K   S   I   T   I
GTCCTTCCTCAAGTTCAATAGCCAAGGATTGACCCAGCAATTTAAAGCGATCGGAACTTTTATAGATGGCT   2736
 S   P   S   S   S   I   A   K   G   L   T   Q   F   K   A   I   G   T   F   I   D   G
CTGAACAAGAAATTACGAATCTTGTGACCTGGTATTCTTCCAAATCCGACGTTGCCCTATCAATAACGCTG   2808
 S   E   Q   E   I   T   N   L   V   T   W   Y   S   S   K   S   D   V   A   P   I   N   N   A
CCAATGAAAAAGGTTAGCAACCGCACTTTCAATAGGTTCTTCCGACATCTATGCGATTTACAATTCTATAA   2880
 A   N   E   K   G   L   A   T   A   L   S   T   G   S   S   D   I   Y   A   I   Y   N   S   I
GCAGTAATAAATTTAATGTAAGTGCTGCCACGTTAGATTCCATTAAAATCAACCCGTCAATAACA         2952
 S   S   N   K   I   N   F   N   V   S   A   A   T   L   D   S   I   K   I   N   P   V   N   N
ACATTGCGAAAGGCTTACCTGGTCTAGCTCAATTCTTCCAATTAGTATTTCCAATTGACCGAAACCAGGAA   3024
 N   I   A   K   G   L   T   Q   Q   Y   T   A   L   G   V   Y   S   D   S   T   I   Q   D   I
GCGATTCAGTTACCTGGTCTAGCTCAATTCTTCCAATTCTTCCAATTCACTGCCGACTTACATCCATTTCCATTTCGGAAACATAGACA   3096
 S   D   S   V   T   W   S   S   N   S   S   I   S   I   S   N   S   T   E   T   K   G
AAGCGACCGCTTTACAGATTGGAAAACAGCAAATCACTGCCACTTACATTCCATTTCGGAAAACATAGACA   3168
 K   A   T   A   L   Q   I   G   N   S   K   I   T   A   T   Y   N   S   I   S   E   N   I   D
TAACCGTCAGCGCAGCAACCCTTTCTTCGATTTCAATATCCTATCCAAATCAATAACAAATATAAACAACGTAT   3240
 I   T   V   S   A   A   T   L   S   S   I   S   P   I   N   T   N   I   N   T   T   V
CAAAACAATTCTTCGCGATTGGGAACGTATTCGGGATGGAACCAAAGCCGATTTAACTTCTTCGGTTACATGGT   3312
 S   K   Q   F   F   A   V   G   T   Y   S   D   G   T   K   A   D   L   T   S   S   V   T   W
CCAGCTCAAATCAATCTCAAGCAAAGCTGAGTAACGCATCGAAACGAAAGGATTGGTTACAGGATTGCTT    3384
 S   S   S   N   Q   S   Q   A   K   V   S   N   A   S   E   T   K   G   L   V   T   G   I   A
CTGGAAATCCTACCATCATAGCGACCTACGGTTCAGTATCGGAAATACAATCCTCACAGTAAACAAACGG   3456
 S   G   N   P   T   I   A   T   Y   G   S   V   S   G   N   I   L   T   V   N   K   T
```

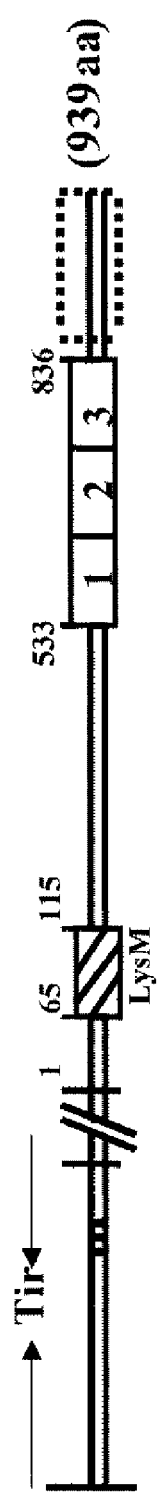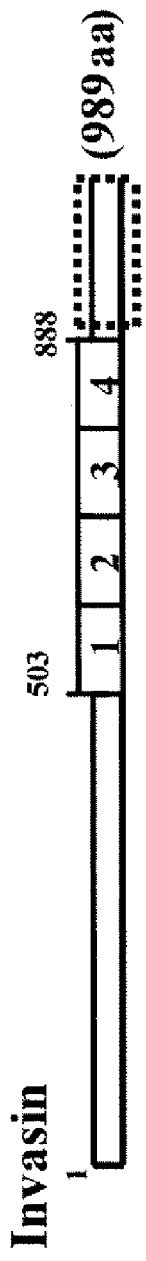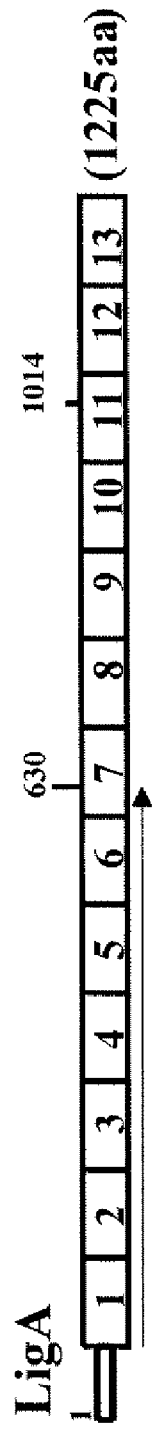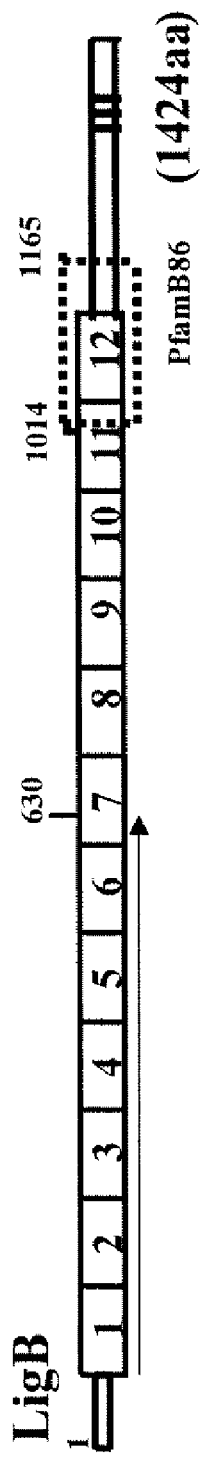
Fig. 9

Fig. 10

```
LigAvari  ltvsNTnakrGlgsTLkqGtvkvtasmGgTedS-VdftVTqAtLtSIeVsPtraSiAKGn  59
LigBvari  aeitNTsgskGitnTLtpGsseisaalgSIksSkVilkVTpAqLiSIaVtPinpSvAKGl  60

LigAvari  t-QkFtATGifTDHSkkniTeqvTWkSSskalSMlNapgeegTgkAiavgkhyyycnlrk  118
LigBvari  irQ-FkATGtyTDHSvqdvTlaTWsSS

```
LigAvari   agiekgytKQ-FsAiGTYSDqsTK-DLTedVTWfSSNpSsvvientpgkKGLafaselGe   473
LigBvari   ninttvs-KQfF-AvGTYSDg-TKaDLTssVTWsSSNgSgakvsnasetKGLvtgiasGn   470

LigAvari   PdItvfYdhhtqssytpvTVtesgivnifhslssisktkgsthgfkatgkfengaeidlt   533
LigBvari   PtIli

```
TAGAATATACTTTGTTTTTATAAATTTTAAAATGTTTTTATTTAAAAACTTTTTACATCCAATAAATCTCAA          72
GAGAACTTCTATAAAATTAATTTTTGTTGATAGTCGCCAAACAACGACTTGATGCAAAAATCTAATTGGATA         144
ATTATCCTTTTTAAATTTTGTAGAGGCTCTCAATAAATAAACACAGCAAATACACAAAATGAAAACTTCAAA         216
TAAAACAATTAGAGTGAGTGTTTATGAAGAAAATATTTTGTATTTCGATTTTTCTTTCGATGTTTTTTCAAA         288
                          M  K  K  I  F  C  I  S  I  F  L  S  M  F  F  Q
GTTGTATGTCTTGGCCACTTTTAACCAGTCTAGCGGGTTTAGCAGCTGGCAAAAGAGGCGGAGATTCATCTT         360
 S  C  M  S  W  P  L  L  T  S  L  A  G  L  A  A  G  K  R  G  G  D  S  S
TTTTCCACCTTCTGTTAGGTAACTTCAATCCGACTATTACAAGAATCGAACTCAGTTATCAAGATTCTTCTA         432
 F  F  H  L  L  G  N  F  N  P  T  I  T  R  I  E  L  S  Y  Q  D  S  S
TCGCAAACGGTACCAGTACAGCCCTAGAAGTTACCGCAATCTTTGATAACGGAACAAATCAGAATATTACGG         504
 I  A  N  G  T  S  T  A  L  E  V  T  A  I  F  D  N  G  T  N  Q  N  I  T
ATTCGACATACATCGTCCCCGATTCCCAATCCGTTGTAACCATCCAAGGTAACAGAGTCAGAGGAATCACTT         576
 D  S  T  Y  I  V  P  D  S  Q  S  V  V  T  I  Q  G  N  R  V  R  G  I  T
CTGGTTCTTCCATTATAAAAGCAGAATATAACGGCCTGTACTCTGAACAAAAAATTACAGTTACACCAGCCA         648
 S  G  S  S  I  I  K  A  E  Y  N  G  L  Y  S  E  Q  K  I  T  V  T  P  A
TTCTTAACTCAATTCAAGTTACGAGTTTAGAGTCAGGTATACTACCTAAAGGTACTAATCGTCAATTATCAG         720
 I  L  N  S  I  Q  V  T  S  L  E  S  G  I  L  P  K  G  T  N  R  Q  L  S
CCATCGGTATCTTTTCGGATGGTTCTCATCAGGATATTTCCAACGATCCATTGATCGTTTGGTCCTCCAGTA         792
 A  I  G  I  F  S  D  G  S  H  Q  D  I  S  N  D  P  L  I  V  W  S  S  S
ATCCTGATTTGGTTCAAGTAGATGATTCAGGGTTGGCATCAGGGATCAATTTAGGAACAGCTCATATTCGTG         864
 N  P  D  L  V  Q  V  D  D  S  G  L  A  S  G  I  N  L  G  T  A  H  I  R
CATCCTTTCAATCAAAACAAGGGGCTGAAGAAATGACCGTTGGAGATGCTGTTCTTTCTCAAATCCAAGTAA         936
 A  S  F  Q  S  K  Q  G  A  E  E  M  T  V  G  D  A  V  L  S  Q  I  Q  V
CTTCAAACAATCTGAATATTCCTCTCGGAAAAAAACAAAAACTAACAGCTACGGGAATCTATTCGGATAACT        1008
 T  S  N  N  L  N  I  P  L  G  K  K  Q  K  L  T  A  T  G  I  Y  S  D  N
CTAACAGGGATATTTCCTCTTCTGTTATCTGGAATTCTTCTAATTCCACTATCGCTAATATTCAAAACAACG        1080
 S  N  R  D  I  S  S  S  V  I  W  N  S  S  N  S  T  I  A  N  I  Q  N  N
GAATATTAGAAACAGCTGATACTGGTATTGTCACTGTTTCTGCTTCTACCGAGAATATAATAGGCTCCGTAA        1152
 G  I  L  E  T  A  D  T  G  I  V  T  V  S  A  S  T  E  N  I  I  G  S  V
AACTAATCGTTACTCCAGCAGCCTTAGTTTCTATTTCTGTTTCTCCGACAAATTCTACAGTTGCAAAAGGTT        1224
 K  L  I  V  T  P  A  A  L  V  S  I  S  V  S  P  T  N  S  T  V  A  K  G
TACAAGAAAACTTTAAAGCTACAGGGATCTTTACAGATAATTCAAACTCGGATATTACCGACCAAGTTACTT        1296
 L  Q  E  N  F  K  A  T  G  I  F  T  D  N  S  N  S  D  I  T  D  Q  V  T
GGGATTCTTCTAATACCGATATTCTCTCAATTTCCAATGCAAGTGATAGCCACGGATTAGCTTCCACACTCA        1368
 W  D  S  S  N  T  D  I  L  S  I  S  N  A  S  D  S  H  G  L  A  S  T  L
ACCAAGGAAATGTTAAAGTCACTGCTTCCATCGGTGGAATACAAGGATCCACTGATTTTAAAGTTACACAAG        1440
 N  Q  G  N  V  K  V  T  A  S  I  G  G  I  Q  G  S  T  D  F  K  V  T  Q
AGGTATTAACTTCCATCGAAGTTTCTCCAACTCGTACTTCCATTGCAAAAGGACTAACTCAAAAGTTTACTG        1512
 E  V  L  T  S  I  E  V  S  P  T  R  T  S  I  A  K  G  L  T  Q  K  F  T
CGATCGGGATTTTTACGGATAACTCTAAAAAGGATATTACGGATCAAGTCACTTGGAATTCTTCTTCAGCAA        1584
 A  I  G  I  F  T  D  N  S  K  K  D  I  T  D  Q  V  T  W  N  S  S  S  A
TCGTAAGCGTGTCTAACTTAGACGACAATAAAGGTCTGGGAAAAGCTCACGCTGTTGGAGACACTACGATTA        1656
 I  V  S  V  S  N  L  D  D  N  K  G  L  G  K  A  H  A  V  G  D  T  T  I
CCGCAACCTTAGGAAAAGTTGCAGGTAAAACTTGGCTTACTGTAGTTCCTGCGGTTCTCACTTCTATTCAAA        1728
 T  A  T  L  G  K  V  A  G  K  T  W  L  T  V  V  P  A  V  L  T  S  I  Q
TCAATCCTGTAAATCCTTCTCTTGCAAAAGGGTTAACTCAAAAATTTACGGCTACTGGGATCTACTCTGACA        1800
 I  N  P  V  N  P  S  L  A  K  G  L  T  Q  K  F  T  A  T  G  I  Y  S  D
ACTCTAACAAGGACATCACTTCCGCTGTTACGTGGTTCTCATCCGATTCTTCAATCGCGACGATTTCAAACG        1872
 N  S  N  K  D  I  T  S  A  V  T  W  F  S  S  D  S  S  I  A  T  I  S  N
CCCAAAAAAATCAAGGAAACGCTTACGGAGCAGCTACAGGAACAACGGATATTAAAGCCACATTCGGAAAGG        1944
 A  Q  K  N  Q  G  N  A  Y  G  A  A  T  G  T  T  D  I  K  A  T  F  G  K
TAAGTAGTCCGGTTTCTACGTTATCCGTTACAGCTGCAAAACTTGTTGAAATCCAAATCACACCGGCTGCTG        2016
 V  S  S  P  V  S  T  L  S  V  T  A  A  K  L  V  E  I  Q  I  T  P  A  A
CTTCCAAAGCAAAAGGACTCACAGAAAGATTCAAGGCTACTGGTATCTTTACGGACAACTCAAATTCCGATA        2088
 A  S  K  A  K  G  L  T  E  R  F  K  A  T  G  I  F  T  D  N  S  N  S  D
TTACAAATCAAGTTACTTGGAATTCCTCTAATACGGATATTGCTGAAATTAAAAAATACCAGTGGAAGTAAAG        2160
 I  T  N  Q  V  T  W  N  S  S  N  T  D  I  A  E  I  K  N  T  S  G  S  K
GTATTACAAATACACTCACTCCAGGATCGAGTGAAATATCCGCAGCCCTCGGTTCAATCAAAAGTTCTAAAG        2232
 G  I  T  N  L  T  P  G  S  S  E  I  S  A  A  L  G  S  I  K  S  S  K
TAATTTTAAAGGTAACTCCGGCACAATTGATTTCCATTGCCGTAACACCTATAAATCCGTCAGTTGCAAAAG        2304
 V  I  L  K  V  T  P  A  Q  L  I  S  I  A  V  T  P  I  N  P  S  V  A  K
GTCTAATACGACAATTTAAAGCCACCGGAACATATACGGATCATTCCGTACAAGACGTGACTGCCCTAGCTA        2376
 G  L  I  R  Q  F  K  A  T  G  T  Y  T  D  H  S  V  Q  D  V  T  A  L  A
CCTGGTCTTCTTCCAATCCCGGAAAAAGCAATGGTTAACAACGTTACAGGTTCGGTTACAACAGTGGCTACCG        2448
 T  W  S  S  S  N  P  G  K  A  M  V  N  N  V  T  G  S  V  T  T  V  A  T
GAAATACAAATATTAAAGCAACGATAGACTCCATATCCGGCTCTTCCGTTTTGAATGTCACTCCTGCACTTC        2520
 G  N  T  N  I  K  A  T  I  D  S  I  S  G  S  S  V  L  N  V  T  P  A  L
TTACTTCTATCGAGATAACACCGACGATTAACTCTATCACTCACGGTCTTACAAAACAATTTAAAGCGACTG        2592
```

Fig. 12A

```
L  T  S  I  E  I  T  P  T  I  N  S  I  T  H  G  L  T  K  Q  F  K  A  T
GTATCTTTTCAGATAAATCTACTCAAAATTTGACTCAGCTTGTAACTTGGATTTCTTCCGATCCATCTAAGA        2664
G  I  F  S  D  K  S  T  Q  N  L  T  Q  L  V  T  W  I  S  S  D  P  S  K
TTGAGATCGAAAACACTTCCGGTAAAAAAGGTATAGCGACAGCCTCTAAATTAGGAAGTTCGAATATTAAGG        2736
I  E  I  E  N  T  S  G  K  K  G  I  A  T  A  S  K  L  G  S  S  N  I  K
CCGTCTACAAATTTGTCCAAAGCTCCCCAATTCCGATTACAGTCACTGACTTAAAACTGAAAAGTATAACTA        2808
A  V  Y  K  F  V  Q  S  S  P  I  P  I  T  V  T  D  L  K  L  K  S  I  T
TCAGTCCTTCCTCAAGTTCAATAGCCAAAGGATTGACCCAGCAATTTAAAGCGATCGGAACTTTTATAGATG        2880
I  S  P  S  S  S  S  I  A  K  G  L  T  Q  Q  F  K  A  I  G  T  F  I  D
GCTCTGAACAAGAAATTACGAATCTTGTGACCTGGTATTCTTCCAAATCCGACGTTGCCCCTATCAATAACG        2952
G  S  E  Q  E  I  T  N  L  V  T  W  Y  S  S  K  S  D  V  A  P  I  N  N
CTGCCAATGCAAAAGGTTTAGCAACCGCACTTTCAATAGGTTCTTCCAACATCTCTGCGATTTACAATTCTA        3024
A  A  N  A  K  G  L  A  T  A  L  S  I  G  S  S  N  I  S  A  I  Y  N  S
TAAGCAGTAATAAAATAAATTTTAATGTAAGTGCTGCCACGTTAGATTCCATTAAAATCAACCCCGTCAATA        3096
I  S  S  N  K  I  N  F  N  V  S  A  A  T  L  D  S  I  K  I  N  P  V  N
ACAACATTGCGAAAGGGCTTACACAACAATATACTGCGCTCGGTGTTTATTCAGACTCCACCATTCAGGACA        3168
N  N  I  A  K  G  L  T  Q  Q  Y  T  A  L  G  V  Y  S  D  S  T  I  Q  D
TCAGCGATTCAGTTACCTGGTCTAGCTCCAATTCTTCCTCAATTAGTATTTCCAATTCGACCGAAACCAAGG        3240
I  S  D  S  V  T  W  S  S  S  N  S  S  I  S  P  T  T  I  S  T  E  T  K
GAAAAGCGACCGCTTTACAGATTGAAAGAGCAAAATCACTGCGACTTACAATTCCATCTCGGAAAACATAG        3312
G  K  A  T  A  L  Q  I  G  K  S  K  I  T  A  T  Y  N  S  I  S  E  N  I
ACATAACGGTCAGCGCAGCAACCCTTTCTTCGATTTCAATATCTCCTATCAATACAAATATAAACGCAACCG        3384
D  I  T  V  S  A  A  T  L  S  S  I  S  I  S  P  I  N  T  N  I  N  A  T
TATCAAAACAATTTTTCGCGATGGGAACGTATTCGGATGGGACCAAAGCGGATTTAACTTCTTCGGTTACAT        3456
V  S  K  Q  F  F  A  M  G  T  Y  S  D  G  T  K  A  D  L  T  S  S  V  T
GGTCCAGCTCAAATAAATCTCAGTCAAAGGTGAGTAACGCATCTAAAACGAAAGGATTGGTTACAGGGATTG        3528
W  S  S  S  N  K  S  Q  S  K  V  S  N  A  S  K  T  K  G  L  V  T  G  I
CTTCTGGAAACTCTATAATCACAGCGACCTACGGTTCAGTATCTGGAAATACAATTCTCACAGTAAACAAA        3600
A  S  G  N  S  I  I  T  A  T  Y  G  S  V  S  G  N  T  I  L  T  V  N  K
CGGACACGATAGCTCCAACGGTTCAATCGGTAGTTTCTTTATCACCTACTACCATCCAAGTTGTATATTCAG        3672
T  D  T  I  A  P  T  V  Q  S  V  V  S  L  S  P  T  T  I  Q  V  V  Y  S
AATCCATAAACAATAAGGAAGCCCCTTGATTTATCCAATTACAAAATAATTAATAGTTCCAATTTATAGGAC        3744
E  S  I  N  N  K  E  A  L  D  L  S  N  Y  K  I  I  N  S  S  N  F  I  G
ATTGTTCAGATAATACGGACTTCAATTCCAATTCTCAAACCGCAGATTTTTCTCTTAGTAGTATCAAAGGAA        3816
H  C  S  D  N  T  D  F  N  S  N  S  Q  T  A  D  F  S  L  S  S  I  K  G
GTAAAAATACTTTTACGATCACACTTTCACATTCACAAATCTTAAACAAATCATACACACTGTAGTCAACA        3888
S  K  N  T  F  T  I  T  L  S  H  S  Q  I  L  N  K  S  Y  T  L  V  V  N
AACAAGGAATTCACGATCTTTCTTCCATTCCAAATTCCTTAAGTTGTCCAAATAACTCTGATTTATAGGAA        3960
K  Q  G  I  H  D  L  S  S  I  P  N  S  L  S  C  P  N  S  D  F  I  G
AAGAACAACTCAAACTTACAAGTGCAGTTTGTAATTCCTTAAACCAAGTGATCGTTTCTTTTTCCAAACCTT        4032
K  E  Q  L  K  L  T  S  A  V  C  N  S  L  N  Q  V  I  V  S  F  S  K  P
TATATTCAGGAAAGGAAGCAACAAAATCCGTGGAATGTTCAAATCCGTCCCAGTGTGAATCCAGATATAAAT        4104
L  Y  S  G  K  E  A  T  K  S  V  E  C  S  N  P  S  Q  C  E  S  R  Y  K
TTGCAGGTGTGTCTTCATTGGAAGTATTACGAGCGTTAGAATTTTAGATGGAAAAGTATGCGGTGGAGCGC        4176
F  A  G  V  S  S  L  G  S  I  T  S  V  R  I  L  D  G  K  V  C  G  G  A
CGGCAGACTCCTCGAAAATATGTTTAACACACTCCCTTCTTCAATCAGGTGGTCAATATACGATCATCGCCG        4248
P  A  D  S  S  K  I  C  L  T  H  S  L  L  Q  S  G  G  Q  Y  T  I  I  A
CAAATGATTTGAACGGAGACGGCTTTGACAACAAATCCTGGGGAGCAATTCGAGATTCATTCGATCAAGAAA        4320
A  N  D  L  N  G  D  F  D  N  K  S  W  G  A  I  R  D  S  F  D  Q  E
ACCTACAATCTTCTCCGAAAGATAGAATCAACTTTATAGGTTGTGGAAATTCCCCTCTCAACTTTATGGATG        4392
N  L  Q  S  S  P  K  D  R  I  N  F  I  G  C  G  N  S  P  L  N  F  M  D
GCCCGATCGTGTCAGATCCTTTTGGAGACGGTTCCGATTTCGGCTTTCTTGTAGATTACAACAATCAAATCT        4464
G  P  I  V  S  D  P  F  G  D  G  S  D  F  G  F  L  V  D  Y  N  N  Q  I
ATCTAGGACCGAATGTAAAAGGAAACCAAGCAGCTCGATTCAATTACGACGGAACTTTTCCGGAATCTATTT        4536
Y  L  G  P  N  V  K  G  N  Q  A  A  R  F  N  Y  D  G  T  F  P  E  S  I
TCTTTTCTTTTACCCAAGATATAAATGCCACTAACCGTGCTTCCTCAAGAGATGGAGGTATCCCGGTTCCGA        4608
F  F  S  F  T  Q  D  I  N  A  T  N  R  A  S  S  R  D  G  G  I  P  V  P
ATTACGTTACGATCGGTCATACCGGTTGTACTCTCAATAGTGCAGACATCACTACTGGATGTGGTCCGGATA        4680
N  Y  V  T  I  G  H  T  G  C  T  L  N  S  A  D  I  T  T  G  C  G  P  D
ACGAAGATGGACGTGGGGTTTTTGCCACCGGATCATTAGATAAAAAATCTCATATTTTTATAGCAGGTTCAA        4752
N  E  D  G  R  G  V  F  A  T  G  S  L  D  K  K  S  H  I  F  I  A  G  S
AACCAAAGAGCTTCAACTATCTCTATTATTCCTCAGATACCGATACAAACCTTAATTTTAAATATATCAGTA        4824
K  P  K  S  F  N  Y  L  Y  Y  S  S  D  T  D  T  N  L  N  F  K  Y  I  S
TGGGAAAAATTACTGGATTGGCGACTGCAGGAACTTCATCTATCGCAGTTCTAGACGATCGGATCCATGTGG        4896
M  G  K  I  T  G  L  A  T  A  G  T  S  S  I  A  V  L  D  D  R  I  H  V
GTTTTGCAAAAAAAAATCAAAATCTAAACGCACCTGATTTCGGTAAAATCACCTTTAATACATCCGAGCACA        4968
G  F  A  K  K  N  Q  N  L  N  A  P  D  F  G  K  I  T  F  N  T  S  E  H
ATCGATGTGCAATTGTAAACAACTGTGAAGCCTCTGACGGATACCGCGGTAATCGTTTTAGAATCGATAGAA        5040
```

Fig. 12B

```
          N  R  C  A  I  V  N  N  C  E  A  S  D  G  Y  R  G  N  R  F  R  I  D  R
TGCCTTACTTTGGCGGCGGCTCCGTGGATGTAGTCAATTATAGATCTTATAAATCTGATAACTCCTCGATCA      5112
          M  P  Y  F  G  G  G  S  V  D  V  V  N  Y  R  S  Y  K  S  D  N  S  S  I
ACTGGGGTTATTATGTGGGAATAGATTCTCTATTCGTTTTTAAAGAAAAACTTTACGCCGCAAACGGAGGAT      5184
          N  W  G  Y  Y  V  G  I  D  S  L  F  V  F  K  E  K  L  Y  A  A  N  G  G
TTCCAAATTCACTACATAATGGAAGTATAATACACTCTACCAGTGCAAATCCTAGTCCTTGTGAGGGGATCA      5256
          F  P  N  S  L  H  N  G  S  I  I  H  S  T  S  A  N  P  S  P  C  E  G  I
ATCGTTGTTCCAGTTGGAAAGACACAGCACCTAGATCCAATCCAAAGTGGCATAACTCTCCTCATAACAATT      5328
          N  R  C  S  S  W  K  D  T  A  P  R  S  N  P  K  W  H  N  S  P  H  N  N
GGTTTTCACTGGAGCTTACAAAGTATCGGAATTTAATTCCGGCGGATAAAGCATTCTCTCAATTCGCAGAAT      5400
          W  F  S  L  E  L  T  K  Y  R  N  L  I  P  A  D  K  A  F  S  Q  F  A  E
TTAACGGAAGATTGTATGTAACAAGAACGATCTGCGTAACGAAAGAAGATCACTCCGGACTCAGACAAAGTT      5472
          F  N  G  R  L  Y  V  T  R  T  I  C  V  T  K  E  D  H  S  G  L  R  Q  S
TACAAACTGTGAAAGGTTGTACGGACGGAAGTTATACAAATCGAAGACCCCAACTTTGGAAATGTGATCCGA      5544
          L  Q  T  V  K  G  C  T  D  G  S  Y  T  N  R  R  P  Q  L  W  K  C  D  P
CTCTAACCGGCGATACAACAACCTGTGAAGCAGAAGATTGGTCTTTAGTAGGAGATAATGGAACCGGGTTTA      5616
          T  L  T  G  D  T  T  T  C  E  A  E  D  W  S  L  V  G  D  N  G  T  G  F
CAAACTTTGGAGACAATTCCAATCACAGTATGACGATGATGGTTGCAAGTGGATCTTATCTCTACATAGGTT      5688
          T  N  F  G  D  N  S  N  H  S  M  T  M  M  V  A  S  G  S  Y  L  Y  I  G
TTGATAACGAAAACGGAATTCAAATCTGGAGAACAAATCTTGAAAATCCGGGAAGTTCATCACACAACTGGG      5760
          F  D  N  E  N  G  I  Q  I  W  R  T  N  L  E  N  P  G  S  S  S  H  N  W
AGCCTATAGGAATAGGTGGATTAAGAGACGTTACCAATCGTCAAATTTATTCGGCTATATCCGGAATGAATT      5832
          E  P  I  G  I  G  G  L  R  D  V  T  N  R  Q  I  Y  S  A  I  S  G  M  N
TTGGTGTAAATTTCGTATATATAAGCGTAGGAAACAAAAATAAACCGGTCAAAATTTACAGACAACAGAATC      5904
          F  G  V  N  F  V  Y  I  S  V  G  N  K  N  K  P  V  K  I  Y  R  Q  Q  N
AATAATATGCAAAATTCATTAAGAATCATCGTGACGATAATGGCTTGTATGTTTACCGGATTAATCTCCTGT      5976
          Q  -
AAAATAAACGAAAATTCAGAAAGGCTTATATTCGATCA                                        6014
```

*Fig. 12C*

SEQUENCE LISTING

<160> NUMBER OF SEQ ID NOS: 53

<210> SEQ ID NO 1
<211> LENGTH: 3993
<212> TYPE: DNA
<213> ORGANISM: Leptospira interrogans

<400> SEQUENCE: 1
acagcaaata cacaaaatga aaacttcaaa taaataaaca cagcaaatac acaaaatgaa 60
aactttaaat aaaacaatta gagtgagtgt ttatgaagaa aatattttgt atttcgattt 120
ttctttcgat gttttttcaa agttgtatgt cttggccact tttaaccagt ctcgcgggtt 180
tagcagctgg caaaagaggc ggggattcat cttttttcca ccttctgtta ggtaactccg 240
atccgactat tacaagaatc gaactcagtt atcaagattc gtctatcgca aacggtacca 300
gtacaaccct agaagttacc gcaatctttg ataacggaac aaatcagaat attacggatt 360
cgacatccat cgtccccgat tcccaatccg ttgtaaccat ccaaggtaac agagtcagag 420
gaatcgcttc tggttcttcc attataaaag cagaatataa cggcctgtac tctgaacaaa 480
aaattacagt tacaccagcc actcttaact caattcaagt tacgagttta gagtcaggta 540
tactacctaa aggtactaat cgtcaattct cagccatcgg tatcttttcg gatggttctc 600
atcaggatat ttccaacgat ccattgatcg tttggtcctc cagtaatcct gatttggttc 660
aagtagatga ttcagggttg gcctcaggga tcaatttagg aacagctcat attcgtgcat 720
cctttcaatc aaaacaaggg gctgaagaaa tgaccgttgg agatgctgtt ctttctcaaa 780
tccaagtaac ttcaaacaat ccgaatattc ctctcggaaa aaaacaaaaa ctaatagcta 840
cgggaatcta ttcagataac tctaacaggg atatttcctc ttctgttatc tggaattctt 900
ctaattccac tatcgctaat attcaaaaca acggaatatt agaaacagct gatactggta 960
ttgtcactat ttctgcttct agcgagaata taataggctc cgtaaaacta atcgttactc 1020
cagcagcctt agtttctatt tctgtttctc caacaaattc tacagtagca aaaggtttac 1080
aagaaaactt taaggctaca gggatcttta cagataattc aaactcggat attaccgacc 1140
aagttacttg ggattcttct aataccgata ttctctcaat ttccaatgca agtgatagcc 1200

-continued

```
acgggttagc ttccacactc aaccaaggga atgttaaagt cactgcttcc atcggtggaa    1260
tacaaggatc cactgatttt acagttacac aagctgcttt gacttcgatc gaagtctctc    1320
cagttttacc ttccattgca aaaggactaa ctcaaaagtt tactgcgatc gggattttta    1380
cggataattc taaaaaggat attacggatc aagtcacttg gaattcttct tcagcaatcg    1440
taagcgtgtc taacttagac gacaataaag gtctgggaaa agctcacgct gttggagaca    1500
cgactattac cgcaacctta ggaaaagttt caggtaaaac ttggcttact gtagttcctg    1560
cggttctcac ttctattcaa atcaatcctg taaatccttc tcttgcaaaa gggttaactc    1620
aaaaattttc tgctacaggg atctactctg acaactctaa caaggacatc acttccgctg    1680
ttacgtggtt ctcatccgat tcttcaatcg cgacgatttc aaacgcccaa aaaaatcaag    1740
gaaacgctta cggagcagct acaggagcaa cggatattaa agccacattc ggaaaagtaa    1800
gtagtccggt ttctacgtta tctgttacag ctgcaaagct tgttgaaatc caaatcacac    1860
cggctgctgc ttccaaagca aaaggactca cagaaagatt caaggctact ggtatcttta    1920
cggacaactc aaattccgat attacaaatc aagttacttg gaattcctct aatacggata    1980
ttcttaccgt ttccaacaca aacgccaaac gcggattagg ttccacttta aaacaaggaa    2040
ctgttaaagt taccgcttct atgggtggaa tcgaagattc tgtagatttt accgtcacac    2100
aggcgacttt gacttcgatc gaagtctctc caactcgcgc ttcgattgca aaaggaatga    2160
ctcaaaaatt tacggctaca ggtatttttta cggatcattc taagaagaac attacagagc    2220
aagtcacctg gaagtcttct tcgaaagcat taagtatgtt gaatgcacct ggtgaagaag    2280
gaacaggtaa ggcgattgca gttggaaaac attactatta ctgcaacctt agaaaaactt    2340
tccgggaaaa cagatattac cgttactccc gcaattctta cttcaattca aatcagtcct    2400
gtaaaaacat tgttcttgtc aaagggttaa cagaaaaatt ttctgctaca ggtatctact    2460
ctgataattc cagcaaggac atcacttccg ctgttacgtg gcattcgtcc aacaactctg    2520
ttgcaacgat ctcaaacaca aaaggttacc aaggacaagc tcacggaacc ggtacaggaa    2580
cagtggatat taaagcgaca ttgggaaatg taagcagcca ggtttccaga ttatccgtta    2640
ccgcagcgga acttattgag attgtattag atcccacttc atctcacaaa gccaagggac    2700
ttactgaaaa tttttaaagcg accggcgtat ttacggataa ttcgacgaaa gatattaccg    2760
accaggttac ttggaaatct tccaaaacag cctacgcaaa aatttcaaat gcgactggaa    2820
gtaaacgggt tgttaatgca atctcgaagg gaacgagcca catctccgct accttaggtt    2880
caatttcaag tgcaaatgcg acattccaag ttactccggc taaagtagtt tcgatcgagg    2940
tcattccgaa taacatatct tttgcaaaag gaaacagtta tcaattcaaa gcaactggaa    3000
tctacacgga tcattcagaa gcagacatta ctgaacaggt aacctggtct tcctcgaatc    3060
cgaaaatcgc atcagtagaa aacaccttcg gatcagctgg tttggttaac acaaccaata    3120
ttggaagtac gaatatcact gcaaagttat ccgataccgt atcaggtgct tctgttttga    3180
atgtcactcc agcgcttctt cgttacatca tgataactcc gagttatgca ggtattgaga    3240
aaggttatac aaaacaattt tcagcgatag gcacttactc ggatcaatct accaaggatt    3300
tgactgagga tgtaacttgg ttctcctcca atccttctag tgttgtaatt gaaaacactc    3360
ccggcaaaaa aggtctcgcg ttcgcttctg aattaggaga acccgacatt acggtattct    3420
acgatcacca cactcagagt tcttatactc cagttacggt tacggaaagt ggtatagtaa    3480
atatcactat tagtctttct tccatttcga aaaccaaagg ttcaacccat caatttaaag    3540
ctaccggaaa gtttgagaat ggtgccgaaa tagatctcac tgaacttgta acttggagtt    3600
```

-continued

```
cttccaatcc tacggtggtt tctattagca atgttgatga cgaaagaggt ttggcaactg   3660
ctctttccgt aggttcctcc aaaatatctg tagattacaa ttctatcagt agctctatcg   3720
attttgaagt aactccagaa atattagcct ctattaaaac ggagccataa catgaaaaca   3780
ttaacaatgt ttacacattc gcaaaaaaca aacaatgagt tcgtgacctt tctttattac   3840
gaattcattg agttatttga ataacgccga ttttatggaa aaggagcaac tcaagtttat   3900
cggtatgatt tgtaacctat cgaccttgtg atcgtttctt ctttcctaac ttttgttcct   3960
aaaaacacgc cgcagattct gcggagtgtt ttt                                3993
```

<210> SEQ ID NO 2
<211> LENGTH: 1225
<212> TYPE: PRT
<213> ORGANISM: Leptospira interrogans

<400> SEQUENCE: 2

```
Met Lys Lys Ile Phe Cys Ile Ser Ile Phe Leu Ser Met Phe Phe Gln
 1               5                   10                  15

Ser Cys Met Ser Trp Pro Leu Leu Thr Ser Leu Ala Gly Leu Ala Ala
            20                  25                  30

Gly Lys Arg Gly Gly Asp Ser Ser Phe Phe His Leu Leu Leu Gly Asn
        35                  40                  45

Ser Asp Pro Thr Ile Thr Arg Ile Glu Leu Ser Tyr Gln Asp Ser Ser
    50                  55                  60

Ile Ala Asn Gly Thr Ser Thr Thr Leu Glu Val Thr Ala Ile Phe Asp
65                  70                  75                  80

Asn Gly Thr Asn Gln Asn Ile Thr Asp Ser Thr Ser Ile Val Pro Asp
                85                  90                  95

Ser Gln Ser Val Val Thr Ile Gln Gly Asn Arg Val Arg Gly Ile Ala
            100                 105                 110

Ser Gly Ser Ser Ile Ile Lys Ala Glu Tyr Asn Gly Leu Tyr Ser Glu
        115                 120                 125

Gln Lys Ile Thr Val Thr Pro Ala Thr Leu Asn Ser Ile Gln Val Thr
    130                 135                 140

Ser Leu Glu Ser Gly Ile Leu Pro Lys Gly Thr Asn Arg Gln Phe Ser
145                 150                 155                 160

Ala Ile Gly Ile Phe Ser Asp Gly Ser His Gln Asp Ile Ser Asn Asp
                165                 170                 175

Pro Leu Ile Val Trp Ser Ser Ser Asn Pro Asp Leu Val Gln Val Asp
            180                 185                 190

Asp Ser Gly Leu Ala Ser Gly Ile Asn Leu Gly Thr Ala His Ile Arg
        195                 200                 205

Ala Ser Phe Gln Ser Lys Gln Gly Ala Glu Glu Met Thr Val Gly Asp
    210                 215                 220

Ala Val Leu Ser Gln Ile Gln Val Thr Ser Asn Asn Pro Asn Ile Pro
225                 230                 235                 240

Leu Gly Lys Lys Gln Lys Leu Ile Ala Thr Gly Ile Tyr Ser Asp Asn
                245                 250                 255

Ser Asn Arg Asp Ile Ser Ser Ser Val Ile Trp Asn Ser Ser Asn Ser
            260                 265                 270

Thr Ile Ala Asn Ile Gln Asn Asn Gly Ile Leu Glu Thr Ala Asp Thr
        275                 280                 285

Gly Ile Val Thr Ile Ser Ala Ser Ser Glu Asn Ile Ile Gly Ser Val
    290                 295                 300
```

```
Lys Leu Ile Val Thr Pro Ala Ala Leu Val Ser Ile Ser Val Ser Pro
305                 310                 315                 320

Thr Asn Ser Thr Val Ala Lys Gly Leu Gln Glu Asn Phe Lys Ala Thr
                325                 330                 335

Gly Ile Phe Thr Asp Asn Ser Asn Ser Asp Ile Thr Asp Gln Val Thr
            340                 345                 350

Trp Asp Ser Ser Asn Thr Asp Ile Leu Ser Ile Ser Asn Ala Ser Asp
        355                 360                 365

Ser His Gly Leu Ala Ser Thr Leu Asn Gln Gly Asn Val Lys Val Thr
370                 375                 380

Ala Ser Ile Gly Gly Ile Gln Gly Ser Thr Asp Phe Thr Val Thr Gln
385                 390                 395                 400

Ala Ala Leu Thr Ser Ile Glu Val Ser Pro Val Leu Pro Ser Ile Ala
                405                 410                 415

Lys Gly Leu Thr Gln Lys Phe Thr Ala Ile Gly Ile Phe Thr Asp Asn
            420                 425                 430

Ser Lys Lys Asp Ile Thr Asp Gln Val Thr Trp Asn Ser Ser Ser Ala
        435                 440                 445

Ile Val Ser Val Ser Asn Leu Asp Asp Asn Lys Gly Leu Gly Lys Ala
450                 455                 460

His Ala Val Gly Asp Thr Thr Ile Thr Ala Thr Leu Gly Lys Val Ser
465                 470                 475                 480

Gly Lys Thr Trp Leu Thr Val Val Pro Ala Val Leu Thr Ser Ile Gln
                485                 490                 495

Ile Asn Pro Val Asn Pro Ser Leu Ala Lys Gly Leu Thr Gln Lys Phe
            500                 505                 510

Ser Ala Thr Gly Ile Tyr Ser Asp Asn Ser Asn Lys Asp Ile Thr Ser
        515                 520                 525

Ala Val Thr Trp Phe Ser Ser Asp Ser Ser Ile Ala Thr Ile Ser Asn
530                 535                 540

Ala Gln Lys Asn Gln Gly Asn Ala Tyr Gly Ala Ala Thr Gly Ala Thr
545                 550                 555                 560

Asp Ile Lys Ala Thr Phe Gly Lys Val Ser Ser Pro Val Ser Thr Leu
                565                 570                 575

Ser Val Thr Ala Ala Lys Leu Val Glu Ile Gln Ile Thr Pro Ala Ala
            580                 585                 590

Ala Ser Lys Ala Lys Gly Leu Thr Glu Arg Phe Lys Ala Thr Gly Ile
        595                 600                 605

Phe Thr Asp Asn Ser Asn Ser Asp Ile Thr Asn Gln Val Thr Trp Asn
610                 615                 620

Ser Ser Asn Thr Asp Ile Leu Thr Val Ser Asn Thr Asn Ala Lys Arg
625                 630                 635                 640

Gly Leu Gly Ser Thr Leu Lys Gln Gly Thr Val Lys Val Thr Ala Ser
                645                 650                 655

Met Gly Gly Ile Glu Asp Ser Val Asp Phe Thr Val Thr Gln Ala Thr
            660                 665                 670

Leu Thr Ser Ile Glu Val Ser Pro Thr Arg Ala Ser Ile Ala Lys Gly
        675                 680                 685

Met Thr Gln Lys Phe Thr Ala Thr Gly Ile Phe Thr Asp His Ser Lys
690                 695                 700

Lys Asn Ile Thr Glu Gln Val Thr Trp Lys Ser Ser Ser Lys Ala Leu
705                 710                 715                 720

Ser Met Leu Asn Ala Pro Gly Glu Glu Gly Thr Gly Lys Ala Ile Ala
                725                 730                 735
```

```
Val Gly Lys His Tyr Tyr Cys Asn Leu Arg Lys Thr Phe Arg Glu
            740             745                 750

Asn Arg Tyr Tyr Arg Tyr Ser Arg Asn Ser Tyr Phe Asn Ser Asn Gln
            755                 760                 765

Ser Cys Lys Asn Ile Val Leu Val Lys Gly Leu Thr Glu Lys Phe Ser
770             775                 780

Ala Thr Gly Ile Tyr Ser Asp Asn Ser Ser Lys Asp Ile Thr Ser Ala
785             790                 795                 800

Val Thr Trp His Ser Asn Asn Ser Val Ala Thr Ile Ser Asn Thr
            805                 810                 815

Lys Gly Tyr Gln Gly Gln Ala His Gly Thr Gly Thr Gly Thr Val Asp
            820                 825                 830

Ile Lys Ala Thr Leu Gly Asn Val Ser Ser Gln Val Ser Arg Leu Ser
            835                 840                 845

Val Thr Ala Ala Glu Leu Ile Glu Ile Val Leu Asp Pro Thr Ser Ser
850             855                 860

His Lys Ala Lys Gly Leu Thr Glu Asn Phe Lys Ala Thr Gly Val Phe
865             870                 875                 880

Thr Asp Asn Ser Thr Lys Asp Ile Thr Asp Gln Val Thr Trp Lys Ser
                885                 890                 895

Ser Lys Thr Ala Tyr Ala Lys Ile Ser Asn Ala Thr Gly Ser Lys Arg
            900                 905                 910

Val Val Asn Ala Ile Ser Lys Gly Thr Ser His Ile Ser Ala Thr Leu
            915                 920                 925

Gly Ser Ile Ser Ser Ala Asn Ala Thr Phe Gln Val Thr Pro Ala Lys
930             935                 940

Val Val Ser Ile Glu Val Ile Pro Asn Asn Ile Ser Phe Ala Lys Gly
945             950                 955                 960

Asn Ser Tyr Gln Phe Lys Ala Thr Gly Ile Tyr Thr Asp His Ser Glu
            965                 970                 975

Ala Asp Ile Thr Glu Gln Val Thr Trp Ser Ser Ser Asn Pro Lys Ile
            980                 985                 990

Ala Ser Val Glu Asn Thr Phe Gly Ser Ala Gly Leu Val Asn Thr Thr
            995                 1000                1005

Asn Ile Gly Ser Thr Asn Ile Thr Ala Lys Leu Ser Asp Thr Val Ser
    1010                1015                1020

Gly Ala Ser Val Leu Asn Val Thr Pro Ala Leu Leu Arg Tyr Ile Met
1025                1030                1035                1040

Ile Thr Pro Ser Tyr Ala Gly Ile Glu Lys Gly Tyr Thr Lys Gln Phe
            1045                1050                1055

Ser Ala Ile Gly Thr Tyr Ser Asp Gln Ser Thr Lys Asp Leu Thr Glu
            1060                1065                1070

Asp Val Thr Trp Phe Ser Ser Asn Pro Ser Val Val Ile Glu Asn
            1075                1080                1085

Thr Pro Gly Lys Lys Gly Leu Ala Phe Ala Ser Glu Leu Gly Glu Pro
    1090                1095                1100

Asp Ile Thr Val Phe Tyr Asp His His Thr Gln Ser Ser Tyr Thr Pro
1105                1110                1115                1120

Val Thr Val Thr Glu Ser Gly Ile Val Asn Ile Thr Ile Ser Leu Ser
            1125                1130                1135

Ser Ile Ser Lys Thr Lys Gly Ser Thr His Gln Phe Lys Ala Thr Gly
            1140                1145                1150

Lys Phe Glu Asn Gly Ala Glu Ile Asp Leu Thr Glu Leu Val Thr Trp
            1155                1160                1165
```

-continued

```
Ser Ser Ser Asn Pro Thr Val Val Ser Ile Ser Asn Val Asp Asp Glu
    1170                1175                1180

Arg Gly Leu Ala Thr Ala Leu Ser Val Gly Ser Ser Lys Ile Ser Val
1185                1190                1195                1200

Asp Tyr Asn Ser Ile Ser Ser Ser Ile Asp Phe Glu Val Thr Pro Glu
                1205                1210                1215

Ile Leu Ala Ser Ile Lys Thr Glu Pro
            1220                1225

<210> SEQ ID NO 3
<211> LENGTH: 4605
<212> TYPE: DNA
<213> ORGANISM: Leptospira interrogans
<220> FEATURE:
<221> NAME/KEY: misc_feature
<222> LOCATION: (1)...(4605)
<223> OTHER INFORMATION: n = A,T,C or G

<400> SEQUENCE: 3
acagcaaata cacaaaatga aaacttcaaa taaataaaca cagcaaatac acaaaatgaa     60
aactttaaat aaaacaatta gagtgagtgt ttatgaagaa aatattttgt atttcgattt    120
ttctttcgat gtttttttcaa ggttgtatgt cttggccact tttaaccggt ctggtaggat    180
taaccgctgg taaaaaaagt aatgggctgt ccttttttcca ccttctgtta ggtaactcta    240
atccgactat tacaagaatc gaactcagtt atcaagattc gtctatcgca aacggtacca    300
gtacaaccct agaagttacc gcaatctttg ataacggaac aaatcagaat attacggatt    360
cgacatccat cgtccccgat tcccaatccg ttgtaaccat ccaaggtaac agagtcagag    420
gaatcgcttc tggttcttcc attataaaag cagaatataa cggcctgtac tctgaacaaa    480
aaattacagt tacaccagcc actcttaact caattcaagt tacgagttta gagtcaggta    540
tactacctaa aggtactaat cgtcaattct cagccatcgg tatcttttcg gatggttctc    600
atcaggatat ttccaacgat ccattgatcg tttggtcctc cagtaatcct gatttggttc    660
aagtagatga ttcagggttg gcctcaggga tcaatttagg aacagctcat attcgtgcat    720
cctttcaatc aaaacaaggg gctgaagaaa tgaccgttgg agatgctgtt ctttctcaaa    780
tccaagtaac ttcaaacaat ccgaatattc ctctcggaaa aaaacaaaaa ctaatagcta    840
cgggaatcta ttcagataac tctaacaggg atatttcctc ttctgttatc tggaattctt    900
ctaattccac tatcgctaat attcaaaaca acggaatatt agaaacagct gatactggta    960
ttgtcactat ttctgcttct agcgagaata taataggctc cgtaaaacta atcgttactc   1020
cagcagcctt agtttctatt tctgtttctc caacaaattc tacagtagca aaaggtttac   1080
aagaaaactt taaggctaca gggatcttta cagataattc aaactcggat attaccgacc   1140
aagttacttg ggattcttct aataccgata ttctctcaat ttccaatgca agtgatagcc   1200
acgggttagc ttccacactc aaccaaggga atgttaaagt cactgcttcc atcggtggaa   1260
tacaaggatc cactgatttt acagttacac aagctgcttt gacttcgatc gaagtctctc   1320
cagttttacc ttccattgca aaaggactaa ctcaaaagtt tactgcgatc gggattttta   1380
cggataattc taaaaaggat attacggatc aagtcacttg gaattcttct tcagcaatcg   1440
taagcgtgtc taacttagac gacaataaag gtctgggaaa agctcacgct gttggagaca   1500
cgactattac cgcaacctta ggaaaagttt caggtaaaac ttggcttact gtagttcctg   1560
cggttctcac ttctattcaa atcaatcctg taaatccttc tcttgcaaaa gggttaactc   1620 aaaaatttc tgctacaggg atctactctg acaactctaa caaggacatc acttccgctg   1680
```

-continued

```
ttacgtggtt ctcatccgat tcttcaatcg cgacgatttc aaacgcccaa aaaaatcaag    1740
gaaacgctta cggagcagct acaggagcaa cggatattaa agccacattc ggaaaagtaa    1800
gtagtccggt ttctacgtta tctgttacag ctgcaaagct tgttgaaatc caaatcacac    1860
cggctgctgc ttccaaagca aaaggactca cagaaagatt caaggctact ggtatcttta    1920
cggacaactc aaattccgat attacaaatc aggttacttg gaattcctct aatacggata    1980
ttgctgaaat tacaaatacc agtggaagta aggtattac aaacacactc accccaggat    2040
cgagtgaaat atccgcggcc ctcggttcaa tcaaagttc taagtaatt ttaaaggtaa    2100 ctccggcaca attgatttcc attgccgtaa cacctataaa tccgtcagtt gcaaaaggtc    2160
taatacgaca atttaaagcc accggaacat atacggatca ttccgtacaa gacgtgactg    2220
ccctagctac ctggtcttct tccaatccca gaaaagcaat ggttaacaac gttacaggtt    2280
cggttacaac agtggctacc ggaaatacaa atattaaagc aacgatagac tccatatccg    2340
gctcttccgt tttgaatgtc actcctgcac ttcttacttc tatcgagata acaccgacga    2400
ttaactctat cactcacggt cttacaaaac aatttaaagc gactggtatc ttttcagata    2460
aatctactca aaatttgact cagcttgtaa cttggatttc ttccgatcca tctaagattg    2520
agatcgaaaa cacttccggt aaaaaaggta tagcgacagc ctctaaatta ggaagttcga    2580
atattaaggc cgtctacaaa ttcatccaaa gctccccaat tccgattaca gtcactgact    2640
taaaactgaa aagtataact atcagtcctt cctcaagttc aatagccaaa ggattgaccc    2700
agcaatttaa agcgatcgga acttttatag atggctctga acaagaaatt acgaatcttg    2760
tgacctggta ttcttccaaa tccgacgttg cccctatcaa taacgctgcc aatgaaaaag    2820
gtttagcaac cgcactttca ataggttctt ccgacatcta tgcgatttac aattctataa    2880
gcagtaataa aataaatttt aatgtaagtg ctgccacgtt agattccatt aaaatcaacc    2940
ccgtcaataa caacattgcg aaagggctta cacaacaata tactgcgctc ggtgtttatt    3000
cagattccac tattcaggac atcagcgatt cagttacctg gtctagctcc aattcttcct    3060
caattagtat ttccaattcg accgaaacca agggaaaagc gaccgcttta cagattggaa    3120
acagcaaaat cactgcgact tacaattcca tttcggaaaa catagacata accgtcagcg    3180
cagcaaccct ttcttcgatt tcaatatctc ctatcaatac aaatataaac acaaccgtat    3240
caaaacaatt cttcgcggtg ggaacgtatt cggatgaac caaagcggat ttaacttctt    3300
cggttacatg gtccagctca aatcaatctc aagcaaaggt gagtaacgca tctgaaacga    3360
aaggattggt tacagggatt gcttctggaa atcctaccat catagcgacc tacggttcag    3420
tatctggaaa tacaatcctc acagtaaaca aaacggacac gatagctccg acggttcaat    3480
ccgtagtttc cttatcacct actaccatcc aagttgtata ttcagaatcc ataaataata    3540
aggaagccct tgatttatcc aattacaaaa taattaatag ttccaatttt ataggacatt    3600
gttcagataa tacggacttc aattccaatt ctcaaaccgc agattttct cttagtagta    3660 tcaaaggaag taaaaatact tttacgatca cactttcaca ttcacaaatt ttaaacaaat    3720
catacacact cgtagtcaac aaacaaggaa ttcacgatct ttcttccatt ccaaattctt    3780
taagttgtcc aaataactct gattttatgg gaaaagaaca actcaaactt acaagtgcag    3840
tttgtaattc cttaaaccaa gtgatcgttt cttttccaa acctttatat tctggaaagg    3900
aagtaacaaa atccgtggaa tgttcaaatc cgtcccagtg tgaatccaga tataaatttg    3960
caggtgtgtc ttcattggga agtattacga gcgttagaat tttagatgga aaggtatgcg    4020
gtggagcgcc ggcagactcc tcgaaaatat gtttaactca ctcccttctt caatcaggtg    4080
```

-continued

```
gtcaatatac gatcatcgcc gcaaatgatt taaacggaga cggctttgac aacaaatcct    4140
ggggagcaat tcgagattca ttcgatcaag aaaacctaca accttctcca aaagatagaa    4200
tcaactttat aggttgcgga aattcccctc tcaactttat ggatggccca atcgtgtcag    4260
atccttttgg agacggttcc gacttcggct ctcttgtaga ttacaacaat caaatctatc    4320
taggaccgaa cgtaaaagga accaagcca actcgattcc attatgacgg aacttttccg     4380
gaatctattt tcttttcttt taccaaagat ataatgcccc taaccgtgct tcctcaaaag    4440
atggagnatc ccggtccgaa ttacgtacga tgggcatacg gttgtactct caatactgca    4500
gacatactac tggatgtggt ccggataacg aaatggacgg ggggttttgg ccaccggatc    4560
nttaacaaaa atccctattt tttagcaggt caaaccaaga aatca                    4605
```

<210> SEQ ID NO 4
<211> LENGTH: 1424
<212> TYPE: PRT
<213> ORGANISM: Leptospira interrogans

<400> SEQUENCE: 4

```
Met Lys Lys Ile Phe Cys Ile Ser Ile Phe Leu Ser Met Phe Phe Gln
 1               5                  10                  15

Gly Cys Met Ser Trp Pro Leu Leu Thr Gly Leu Val Gly Leu Thr Ala
            20                  25                  30

Gly Lys Lys Ser Asn Gly Leu Ser Phe Phe His Leu Leu Leu Gly Asn
        35                  40                  45

Ser Asn Pro Thr Ile Thr Arg Ile Glu Leu Ser Tyr Gln Asp Ser Ser
    50                  55                  60

Ile Ala Asn Gly Thr Ser Thr Thr Leu Glu Val Thr Ala Ile Phe Asp
65                  70                  75                  80

Asn Gly Thr Asn Gln Asn Ile Thr Asp Ser Thr Ser Ile Val Pro Asp
                85                  90                  95

Ser Gln Ser Val Val Thr Ile Gln Gly Asn Arg Val Arg Gly Ile Ala
            100                 105                 110

Ser Gly Ser Ser Ile Ile Lys Ala Glu Tyr Asn Gly Leu Tyr Ser Glu
        115                 120                 125

Gln Lys Ile Thr Val Thr Pro Ala Thr Leu Asn Ser Ile Gln Val Thr
    130                 135                 140

Ser Leu Glu Ser Gly Ile Leu Pro Lys Gly Thr Asn Arg Gln Phe Ser
145                 150                 155                 160

Ala Ile Gly Ile Phe Ser Asp Gly Ser His Gln Asp Ile Ser Asn Asp
                165                 170                 175

Pro Leu Ile Val Trp Ser Ser Asn Pro Asp Leu Val Gln Val Asp
            180                 185                 190

Asp Ser Gly Leu Ala Ser Gly Ile Asn Leu Gly Thr Ala His Ile Arg
        195                 200                 205

Ala Ser Phe Gln Ser Lys Gln Gly Ala Glu Glu Met Thr Val Gly Asp
    210                 215                 220

Ala Val Leu Ser Gln Ile Gln Val Thr Ser Asn Asn Pro Asn Ile Pro
225                 230                 235                 240

Leu Gly Lys Lys Gln Lys Leu Ile Ala Thr Gly Ile Tyr Ser Asp Asn
                245                 250                 255

Ser Asn Arg Asp Ile Ser Ser Ser Val Ile Trp Asn Ser Ser Asn Ser
            260                 265                 270

Thr Ile Ala Asn Ile Gln Asn Asn Gly Ile Leu Glu Thr Ala Asp Thr
        275                 280                 285
```

```
Gly Ile Val Thr Ile Ser Ala Ser Ser Glu Asn Ile Ile Gly Ser Val
            290                 295                 300
Lys Leu Ile Val Thr Pro Ala Ala Leu Val Ser Ile Ser Val Ser Pro
305                 310                 315                 320
Thr Asn Ser Thr Val Ala Lys Gly Leu Gln Glu Asn Phe Lys Ala Thr
                325                 330                 335
Gly Ile Phe Thr Asp Asn Ser Asn Ser Asp Ile Thr Asp Gln Val Thr
            340                 345                 350
Trp Asp Ser Ser Asn Thr Asp Ile Leu Ser Ile Ser Asn Ala Ser Asp
                355                 360                 365
Ser His Gly Leu Ala Ser Thr Leu Asn Gln Gly Asn Val Lys Val Thr
370                 375                 380
Ala Ser Ile Gly Gly Ile Gln Gly Ser Thr Asp Phe Thr Val Thr Gln
385                 390                 395                 400
Ala Ala Leu Thr Ser Ile Glu Val Ser Pro Val Leu Pro Ser Ile Ala
                405                 410                 415
Lys Gly Leu Thr Gln Lys Phe Thr Ala Ile Gly Ile Phe Thr Asp Asn
            420                 425                 430
Ser Lys Lys Asp Ile Thr Asp Gln Val Thr Trp Asn Ser Ser Ser Ala
                435                 440                 445
Ile Val Ser Val Ser Asn Leu Asp Asp Asn Lys Gly Leu Gly Lys Ala
450                 455                 460
His Ala Val Gly Asp Thr Thr Ile Thr Ala Thr Leu Gly Lys Val Ser
465                 470                 475                 480
Gly Lys Thr Trp Leu Thr Val Val Pro Ala Val Leu Thr Ser Ile Gln
                485                 490                 495
Ile Asn Pro Val Asn Pro Ser Leu Ala Lys Gly Leu Thr Gln Lys Phe
            500                 505                 510
Ser Ala Thr Gly Ile Tyr Ser Asp Asn Ser Asn Lys Asp Ile Thr Ser
                515                 520                 525
Ala Val Thr Trp Phe Ser Ser Asp Ser Ser Ile Ala Thr Ile Ser Asn
530                 535                 540
Ala Gln Lys Asn Gln Gly Asn Ala Tyr Gly Ala Ala Thr Gly Ala Thr
545                 550                 555                 560
Asp Ile Lys Ala Thr Phe Gly Lys Val Ser Pro Val Ser Thr Leu
                565                 570                 575
Ser Val Thr Ala Ala Lys Leu Val Glu Ile Gln Ile Thr Pro Ala Ala
            580                 585                 590
Ala Ser Lys Ala Lys Gly Leu Thr Glu Arg Phe Lys Ala Thr Gly Ile
                595                 600                 605
Phe Thr Asp Asn Ser Asn Ser Asp Ile Thr Asn Gln Val Thr Trp Asn
610                 615                 620
Ser Ser Asn Thr Asp Ile Ala Glu Ile Thr Asn Thr Ser Gly Ser Lys
625                 630                 635                 640
Gly Ile Thr Asn Thr Leu Thr Pro Gly Ser Ser Glu Ile Ser Ala Ala
                645                 650                 655
Leu Gly Ser Ile Lys Ser Ser Lys Val Ile Leu Lys Val Thr Pro Ala
            660                 665                 670
Gln Leu Ile Ser Ile Ala Val Thr Pro Ile Asn Pro Ser Val Ala Lys
                675                 680                 685
Gly Leu Ile Arg Gln Phe Lys Ala Thr Gly Thr Tyr Thr Asp His Ser
            690                 695                 700
Val Gln Asp Val Thr Ala Leu Ala Thr Trp Ser Ser Ser Asn Pro Arg
705                 710                 715                 720
```

-continued

Lys Ala Met Val Asn Val Thr Gly Ser Val Thr Val Ala Thr
                725                 730                 735

Gly Asn Thr Asn Ile Lys Ala Thr Ile Asp Ser Ile Ser Gly Ser Ser
            740                 745                 750

Val Leu Asn Val Thr Pro Ala Leu Leu Thr Ser Ile Glu Ile Thr Pro
            755                 760                 765

Thr Ile Asn Ser Ile Thr His Gly Leu Thr Lys Gln Phe Lys Ala Thr
            770                 775                 780

Gly Ile Phe Ser Asp Lys Ser Thr Gln Asn Leu Thr Gln Leu Val Thr
785                 790                 795                 800

Trp Ile Ser Ser Asp Pro Ser Lys Ile Glu Ile Glu Asn Thr Ser Gly
                805                 810                 815

Lys Lys Gly Ile Ala Thr Ala Ser Lys Leu Gly Ser Ser Asn Ile Lys
            820                 825                 830

Ala Val Tyr Lys Phe Ile Gln Ser Ser Pro Ile Pro Ile Thr Val Thr
            835                 840                 845

Asp Leu Lys Leu Lys Ser Ile Thr Ile Ser Pro Ser Ser Ser Ser Ile
850                 855                 860

Ala Lys Gly Leu Thr Gln Gln Phe Lys Ala Ile Gly Thr Phe Ile Asp
865                 870                 875                 880

Gly Ser Glu Gln Glu Ile Thr Asn Leu Val Thr Trp Tyr Ser Ser Lys
                885                 890                 895

Ser Asp Val Ala Pro Ile Asn Asn Ala Ala Asn Glu Lys Gly Leu Ala
            900                 905                 910

Thr Ala Leu Ser Ile Gly Ser Ser Asp Ile Tyr Ala Ile Tyr Asn Ser
            915                 920                 925

Ile Ser Ser Asn Lys Ile Asn Phe Asn Val Ser Ala Ala Thr Leu Asp
            930                 935                 940

Ser Ile Lys Ile Asn Pro Val Asn Asn Ile Ala Lys Gly Leu Thr
945                 950                 955                 960

Gln Gln Tyr Thr Ala Leu Gly Val Tyr Ser Asp Ser Thr Ile Gln Asp
                965                 970                 975

Ile Ser Asp Ser Val Thr Trp Ser Ser Ser Asn Ser Ser Ser Ile Ser
            980                 985                 990

Ile Ser Asn Ser Thr Glu Thr Lys Gly Lys Ala Thr Ala Leu Gln Ile
            995                 1000                1005

Gly Asn Ser Lys Ile Thr Ala Thr Tyr Asn Ser Ile Ser Glu Asn Ile
        1010                1015                1020

Asp Ile Thr Val Ser Ala Ala Thr Leu Ser Ile Ser Ile Ser Pro
1025                1030                1035                1040

Ile Asn Thr Asn Ile Asn Thr Thr Val Ser Lys Gln Phe Phe Ala Val
                1045                1050                1055

Gly Thr Tyr Ser Asp Gly Thr Lys Ala Asp Leu Thr Ser Ser Val Thr
            1060                1065                1070

Trp Ser Ser Ser Asn Gln Ser Gln Ala Lys Val Ser Asn Ala Ser Glu
        1075                1080                1085

Thr Lys Gly Leu Val Thr Gly Ile Ala Ser Gly Asn Pro Thr Ile Ile
        1090                1095                1100

Ala Thr Tyr Gly Ser Val Ser Gly Asn Thr Ile Leu Thr Val Asn Lys
1105                1110                1115                1120

Thr Asp Thr Ile Ala Pro Thr Val Gln Ser Val Val Ser Leu Ser Pro
            1125                1130                1135

Thr Thr Ile Gln Val Val Tyr Ser Glu Ser Ile Asn Asn Lys Glu Ala
            1140                1145                1150

Leu Asp Leu Ser Asn Tyr Lys Ile Ile Asn Ser Ser Asn Phe Ile Gly
    1155                1160                1165

His Cys Ser Asp Asn Thr Asp Phe Asn Ser Asn Ser Gln Thr Ala Asp
    1170                1175                1180

Phe Ser Leu Ser Ser Ile Lys Gly Ser Lys Asn Thr Phe Thr Ile Thr
1185                1190                1195                1200

Leu Ser His Ser Gln Ile Leu Asn Lys Ser Tyr Thr Leu Val Val Asn
                1205                1210                1215

Lys Gln Gly Ile His Asp Leu Ser Ser Ile Pro Asn Ser Leu Ser Cys
                1220                1225                1230

Pro Asn Asn Ser Asp Phe Met Gly Lys Glu Gln Leu Lys Leu Thr Ser
                1235                1240                1245

Ala Val Cys Asn Ser Leu Asn Gln Val Ile Val Ser Phe Ser Lys Pro
                1250                1255                1260

Leu Tyr Ser Gly Lys Glu Val Thr Lys Ser Val Glu Cys Ser Asn Pro
1265                1270                1275                1280

Ser Gln Cys Glu Ser Arg Tyr Lys Phe Ala Gly Val Ser Ser Leu Gly
                1285                1290                1295

Ser Ile Thr Ser Val Arg Ile Leu Asp Gly Lys Val Cys Gly Gly Ala
                1300                1305                1310

Pro Ala Asp Ser Ser Lys Ile Cys Leu Thr His Ser Leu Leu Gln Ser
                1315                1320                1325

Gly Gly Gln Tyr Thr Ile Ile Ala Ala Asn Asp Leu Asn Gly Asp Gly
                1330                1335                1340

Phe Asp Asn Lys Ser Trp Gly Ala Ile Arg Asp Ser Phe Asp Gln Glu
1345                1350                1355                1360

Asn Leu Gln Pro Ser Pro Lys Asp Arg Ile Asn Phe Ile Gly Cys Gly
                1365                1370                1375

Asn Ser Pro Leu Asn Phe Met Asp Gly Pro Ile Val Ser Asp Pro Phe
                1380                1385                1390

Gly Asp Gly Ser Asp Phe Gly Ser Leu Val Asp Tyr Asn Asn Gln Ile
                1395                1400                1405

Tyr Leu Gly Pro Asn Val Lys Gly Asn Gln Ala Asn Ser Ile Pro Leu
                1410                1415                1420

<210> SEQ ID NO 5
<211> LENGTH: 83
<212> TYPE: PRT
<213> ORGANISM: Leptospira interrogans

<400> SEQUENCE: 5

Ala Thr Leu Asn Ser Ile Gln Val Thr Ser Leu Glu Ser Gly Ile Leu
1               5                   10                  15

Pro Lys Gly Thr Asn Arg Gln Phe Ser Ala Ile Gly Ile Phe Ser Asp
                20                  25                  30

Gly Ser His Gly Asp Ile Ser Asn Asp Pro Leu Ile Val Trp Ser Ser
            35                  40                  45

Ser Asn Pro Asp Leu Val Gln Val Asp Ser Gly Leu Ala Ser Gly
        50                  55                  60

Ile Asn Leu Gly Thr Ala His Ile Arg Ala Ser Phe Gln Ser Lys Gln
65                  70                  75                  80

Gly Ala Glu

<210> SEQ ID NO 6
<211> LENGTH: 86
<212> TYPE: PRT

-continued

<213> ORGANISM: Leptospira interrogans

<400> SEQUENCE: 6

Ala Val Leu Ser Gln Ile Gln Val Thr Ser Asn Asn Pro Asn Ile Pro
1               5                   10                  15

Leu Gly Lys Lys Gln Lys Leu Ile Ala Thr Gly Ile Tyr Ser Asp Asn
            20                  25                  30

Ser Asn Arg Asp Ile Ser Ser Val Ile Trp Asn Ser Ser Asn Ser
        35                  40                  45

Thr Ile Ala Asn Ile Gln Asn Asn Gly Ile Leu Glu Thr Ala Asp Thr
    50                  55                  60

Gly Ile Val Thr Ile Ser Ala Ser Ser Glu Asn Ile Ile Gly Ser Val
65                  70                  75                  80

Lys Leu Ile Val Thr Pro
                85

<210> SEQ ID NO 7
<211> LENGTH: 90
<212> TYPE: PRT
<213> ORGANISM: Leptospira interrogans

<400> SEQUENCE: 7

Ala Ala Leu Val Ser Ile Ser Val Ser Pro Thr Asn Ser Thr Val Ala
1               5                   10                  15

Lys Gly Leu Gln Glu Asn Phe Lys Ala Thr Gly Ile Phe Thr Asp Asn
            20                  25                  30

Ser Asn Ser Asp Ile Thr Asp Gln Val Thr Trp Asp Ser Ser Asn Thr
        35                  40                  45

Asp Ile Leu Ser Ile Ser Asn Ala Ser Asp Ser His Gly Leu Ala Ser
    50                  55                  60

Thr Leu Asn Gln Gly Asn Val Lys Val Thr Ser Ile Gly Gly Ile
65                  70                  75                  80

Gln Gly Ser Thr Asp Phe Thr Val Thr Gln
                85                  90

<210> SEQ ID NO 8
<211> LENGTH: 89
<212> TYPE: PRT
<213> ORGANISM: Leptospira interrogans

<400> SEQUENCE: 8

Ala Ala Leu Thr Ser Ile Glu Val Ser Pro Val Leu Pro Ser Ile Ala
1               5                   10                  15

Lys Gly Leu Thr Gln Lys Phe Thr Ala Ile Gly Ile Phe Thr Asp Asn
20 25 30

Ser Lys Lys Asp Ile Thr Asp Gln Val Thr Trp Asn Ser Ser Ser Ala
35 40 45

Ile Val Ser Val Ser Asn Leu Asp Asp Asn Lys Gly Leu Gly Lys Ala
50 55 60

His Ala Val Gly Asp Thr Thr Ile Thr Ala Thr Leu Gly Lys Val Ser
65 70 75 80

Gly Lys Thr Trp Leu Thr Val Val Pro
85

<210> SEQ ID NO 9
<211> LENGTH: 91
<212> TYPE: PRT
<213> ORGANISM: Leptospira interrogans

```
<400> SEQUENCE: 9

Ala Val Leu Thr Ser Ile Gln Ile Asn Pro Val Asn Pro Ser Leu Ala
1               5                   10                  15

Lys Gly Leu Thr Gln Lys Phe Ser Ala Thr Gly Ile Tyr Ser Asp Asn
            20                  25                  30

Ser Asn Lys Asp Ile Thr Ser Ala Val Thr Trp Phe Ser Ser Asp Ser
        35                  40                  45

Ser Ile Ala Thr Ile Ser Asn Ala Gln Lys Asn Gln Gly Asn Ala Tyr
    50                  55                  60

Gly Ala Ala Thr Gly Ala Thr Asp Ile Lys Ala Thr Phe Gly Lys Val
65                  70                  75                  80

Ser Ser Pro Val Ser Thr Leu Ser Val Thr Ala
                85                  90

<210> SEQ ID NO 10
<211> LENGTH: 90
<212> TYPE: PRT
<213> ORGANISM: Leptospira interrogans

<400> SEQUENCE: 10

Ala Lys Leu Val Glu Ile Gln Ile Thr Pro Ala Ala Ser Lys Ala
1               5                   10                  15

Lys Gly Leu Thr Glu Arg Phe Lys Ala Thr Gly Ile Phe Thr Asp Asn
            20                  25                  30

Ser Asn Ser Asp Ile Thr Asn Gln Val Thr Trp Asn Ser Ser Asn Thr
        35                  40                  45

Asp Ile Leu Thr Val Ser Asn Thr Asn Ala Lys Arg Gly Leu Gly Ser
    50                  55                  60

Thr Leu Lys Gln Gly Thr Val Lys Val Thr Ala Ser Met Gly Gly Ile
65                  70                  75                  80

Glu Asp Ser Val Asp Phe Thr Val Thr Gln
                85                  90

<210> SEQ ID NO 11
<211> LENGTH: 90
<212> TYPE: PRT
<213> ORGANISM: Leptospira interrogans

<400> SEQUENCE: 11

Ala Thr Leu Thr Ser Ile Glu Val Ser Pro Thr Arg Ala Ser Ile Ala
1               5                   10                  15

Lys Gly Met Thr Gln Lys Phe Thr Ala Thr Gly Ile Phe Thr Asp His
            20                  25                  30

Ser Lys Lys Asn Ile Thr Glu Gln Val Thr Trp Lys Ser Ser Ser Lys
        35                  40                  45

Ala Leu Ser Met Leu Asn Ala Pro Gly Glu Glu Gly Thr Gly Lys Ala
    50                  55                  60

Ile Ala Val Gly Lys His Tyr Tyr Tyr Cys Asn Leu Arg Lys Thr Phe
65                  70                  75                  80

Arg Glu Asn Arg Tyr Tyr Arg Tyr Ser Arg
                85                  90

<210> SEQ ID NO 12
<211> LENGTH: 91
<212> TYPE: PRT
<213> ORGANISM: Leptospira interrogans

<400> SEQUENCE: 12
```

```
Asn Ser Tyr Phe Asn Ser Asn Gln Ser Cys Lys Asn Ile Val Leu Val
1               5                   10                  15

Lys Gly Leu Thr Glu Lys Phe Ser Ala Thr Gly Ile Tyr Ser Asp Asn
            20                  25                  30

Ser Ser Lys Asp Ile Thr Ser Ala Val Thr Trp His Ser Ser Asn Asn
        35                  40                  45

Ser Val Ala Thr Ile Ser Asn Thr Lys Gly Tyr Gln Gly Gln Ala His
    50                  55                  60

Gly Thr Gly Thr Gly Thr Val Asp Ile Lys Ala Thr Leu Gly Asn Val
65                  70                  75                  80

Ser Ser Gln Val Ser Arg Leu Ser Val Thr Ala
                85                  90
```

<210> SEQ ID NO 13
<211> LENGTH: 91
<212> TYPE: PRT
<213> ORGANISM: Leptospira interrogans

<400> SEQUENCE: 13

```
Ala Glu Leu Ile Glu Ile Val Leu Asp Pro Thr Ser Ser His Lys Ala
1               5                   10                  15

Lys Gly Leu Thr Glu Asn Phe Lys Ala Thr Gly Val Phe Thr Asp Asn
            20                  25                  30

Ser Thr Lys Asp Ile Thr Asp Gln Val Thr Trp Lys Ser Ser Lys Thr
        35                  40                  45

Ala Tyr Ala Lys Ile Ser Asn Ala Thr Gly Ser Lys Arg Val Val Asn
    50                  55                  60

Ala Ile Ser Lys Gly Thr Ser His Ile Ser Ala Thr Leu Gly Ser Ile
65                  70                  75                  80

Ser Ser Ala Asn Ala Thr Phe Gln Val Thr Pro
                85                  90
```

<210> SEQ ID NO 14
<211> LENGTH: 91
<212> TYPE: PRT
<213> ORGANISM: Leptospira interrogans

<400> SEQUENCE: 14

```
Ala Lys Val Val Ser Ile Glu Val Ile Pro Asn Asn Ile Ser Phe Ala
1               5                   10                  15

Lys Gly Asn Ser Tyr Gln Phe Lys Ala Thr Gly Ile Tyr Thr Asp His
            20                  25                  30

Ser Glu Ala Asp Ile Thr Glu Gln Val Thr Trp Ser Ser Ser Asn Pro
        35                  40                  45

Lys Ile Ala Ser Val Glu Asn Thr Phe Gly Ser Ala Gly Leu Val Asn
    50                  55                  60

Thr Thr Asn Ile Gly Ser Thr Asn Ile Thr Ala Lys Leu Ser Asp Thr
65                  70                  75                  80

Val Ser Gly Ala Ser Val Leu Asn Val Thr Pro
                85                  90
```

<210> SEQ ID NO 15
<211> LENGTH: 92
<212> TYPE: PRT
<213> ORGANISM: Leptospira interrogans

<400> SEQUENCE: 15

```
Ala Leu Leu Arg Tyr Ile Met Ile Thr Pro Ser Tyr Ala Gly Ile Glu
1               5                   10                  15
```

Lys Gly Tyr Thr Lys Gln Phe Ser Ala Ile Gly Thr Tyr Ser Asp Gln
            20                  25                  30

Ser Thr Lys Asp Leu Thr Glu Asp Val Thr Trp Phe Ser Ser Asn Pro
        35                  40                  45

Ser Ser Val Val Ile Glu Asn Thr Pro Gly Lys Lys Gly Leu Ala Phe
    50                  55                  60

Ala Ser Glu Leu Gly Glu Pro Asp Ile Thr Val Phe Tyr Asp His His
65                  70                  75                  80

Thr Gln Ser Ser Tyr Thr Pro Val Thr Val Thr Glu
                85                  90

<210> SEQ ID NO 16
<211> LENGTH: 91
<212> TYPE: PRT
<213> ORGANISM: Leptospira interrogans

<400> SEQUENCE: 16

Ser Gly Ile Val Asn Ile Thr Ile Ser Leu Ser Ser Ile Ser Lys Thr
1               5                   10                  15

Lys Gly Ser Thr His Gln Phe Lys Ala Thr Gly Lys Phe Glu Asn Gly
            20                  25                  30

Ala Glu Ile Asp Leu Thr Glu Leu Val Thr Trp Ser Ser Ser Asn Pro
        35                  40                  45

Thr Val Val Ser Ile Ser Asn Val Asp Asp Glu Arg Gly Leu Ala Thr
    50                  55                  60

Ala Leu Ser Val Gly Ser Ser Lys Ile Ser Val Asp Tyr Asn Ser Ile
65                  70                  75                  80

Ser Ser Ser Ile Asp Phe Glu Val Thr Pro Glu
                85                  90

<210> SEQ ID NO 17
<211> LENGTH: 80
<212> TYPE: PRT
<213> ORGANISM: Unknown
<220> FEATURE:
<223> OTHER INFORMATION: Region_name = "pfam02368, Big_2, Bacterial
      Ig-like domain (group 2). This family consists of bacterial
      domains with an Ig-like fold. Members of this family are found in
      bacterial and phage surface proteins such as intimins.

<400> SEQUENCE: 17

Ala Val Thr Ser Val Thr Val Ser Pro Thr Val Ala Ser Leu Leu Lys
1               5                   10                  15

Gly Ala Thr Leu Gln Leu Thr Ala Thr Gly Thr Pro Ala Asp Ala Ser
            20                  25                  30

Asn Gly Lys Val Thr Trp Ser Ser Ser Asn Thr Ser Val Ala Thr Val
        35                  40                  45

Ser Asn Ser Thr Gly Leu Val Thr Ala Leu Ala Lys Gly Thr Ala Thr
    50                  55                  60

Ile Thr Ala Thr Ser Gly Asp Gly Asn Ser Ser Ala Thr Val Thr Val
65                  70                  75                  80

<210> SEQ ID NO 18
<211> LENGTH: 81
<212> TYPE: PRT
<213> ORGANISM: Unknown
<220> FEATURE:
<223> OTHER INFORMATION: Region_name= "smart00635, BID_2, Bacterial
      Ig-like domain 2."

<400> SEQUENCE: 18

```
Val Val Thr Ser Val Thr Val Thr Pro Thr Thr Ala Ser Val Ala Lys
 1               5                  10                  15

Gly Ala Thr Leu Gln Leu Thr Ala Thr Val Thr Pro Ser Ser Ala Lys
                20                  25                  30

Val Thr Gly Lys Val Thr Trp Thr Ser Ser Asn Pro Ser Val Ala Thr
                35                  40                  45

Val Val Asn Ala Ser Gly Leu Thr Cys Thr Ala Val Ala Ala Gly Thr
 50                  55                  60

Ala Thr Ile Thr Ala Thr Ser Gly Asp Gly Ser Ser Ala Thr Gly Val
 65                  70                  75                  80

Thr
```

<210> SEQ ID NO 19
<211> LENGTH: 82
<212> TYPE: PRT
<213> ORGANISM: Leptospira interrogans

<400> SEQUENCE: 19

```
Thr Ile Thr Arg Ile Glu Leu Ser Tyr Gln Asp Ser Ser Ile Ala Asn
 1               5                  10                  15

Gly Thr Ser Thr Thr Leu Glu Val Thr Ala Ile Phe Asp Asn Gly Thr
                20                  25                  30

Asn Gln Asn Ile Thr Asp Ser Thr Ser Ile Val Pro Asp Ser Gln Ser
                35                  40                  45

Val Val Thr Ile Gln Gly Asn Arg Val Arg Gly Ile Ala Ser Gly Ser
 50                  55                  60

Ser Ile Ile Lys Ala Glu Tyr Asn Gly Leu Tyr Ser Glu Gln Lys Ile
 65                  70                  75                  80

Thr Val
```

<210> SEQ ID NO 20
<211> LENGTH: 86
<212> TYPE: PRT
<213> ORGANISM: Leptospira interrogans

<400> SEQUENCE: 20

```
Thr Leu Asn Ser Ile Gln Val Thr Ser Leu Glu Ser Gly Ile Leu Pro
 1               5                  10                  15

Lys Gly Thr Asn Arg Gln Phe Ser Ala Ile Gly Ile Phe Ser Asp Gly
                20                  25                  30

Ser His Gln Asp Ile Ser Asn Asp Pro Leu Ile Val Trp Ser Ser Ser
                35                  40                  45

Asn Pro Asp Leu Val Gln Val Asp Asp Ser Gly Leu Ala Ser Gly Ile
 50                  55                  60

Asn Leu Gly Thr Ala His Ile Arg Ala Ser Phe Gln Ser Lys Gln Gly
 65                  70                  75                  80

Ala Glu Glu Met Thr Val
                85
```

<210> SEQ ID NO 21
<211> LENGTH: 83
<212> TYPE: PRT
<213> ORGANISM: Leptospira interrogans

<400> SEQUENCE: 21

```
Val Leu Ser Gln Ile Gln Val Thr Ser Asn Asn Pro Asn Ile Pro Leu
 1               5                  10                  15
```

```
Gly Lys Lys Gln Lys Leu Ile Ala Thr Gly Ile Tyr Ser Asp Asn Ser
                20                  25                  30

Asn Arg Asp Ile Ser Ser Val Ile Trp Asn Ser Asn Ser Thr
            35                  40                  45

Ile Ala Asn Ile Gln Asn Asn Gly Ile Leu Glu Thr Ala Asp Thr Gly
 50                  55                  60

Ile Val Thr Ile Ser Ala Ser Ser Glu Asn Ile Ile Gly Ser Val Lys
 65                  70                  75                  80

Leu Ile Val
```

<210> SEQ ID NO 22
<211> LENGTH: 87
<212> TYPE: PRT
<213> ORGANISM: Leptospira interrogans

<400> SEQUENCE: 22

```
Ala Leu Val Ser Ile Ser Val Ser Pro Thr Asn Ser Thr Val Ala Lys
  1               5                  10                  15

Gly Leu Gln Glu Asn Phe Lys Ala Thr Gly Ile Phe Thr Asp Asn Ser
                20                  25                  30

Asn Ser Asp Ile Thr Asp Gln Val Thr Trp Asp Ser Ser Asn Thr Asp
            35                  40                  45

Ile Leu Ser Ile Ser Asn Ala Ser Asp Ser His Gly Leu Ala Ser Thr
 50                  55                  60

Leu Asn Gln Gly Asn Val Lys Val Thr Ala Ser Ile Gly Gly Ile Gln
 65                  70                  75                  80

Gly Ser Thr Asp Phe Thr Val
                85
```

<210> SEQ ID NO 23
<211> LENGTH: 86
<212> TYPE: PRT
<213> ORGANISM: Leptospira interrogans

<400> SEQUENCE: 23

```
Ala Leu Thr Ser Ile Glu Val Ser Pro Val Leu Pro Ser Ile Ala Lys
  1               5                  10                  15

Gly Leu Thr Gln Lys Phe Thr Ala Ile Gly Ile Phe Thr Asp Asn Ser
                20                  25                  30

Lys Lys Asp Ile Thr Asp Gln Val Thr Trp Asn Ser Ser Ala Ile
            35                  40                  45

Val Ser Val Ser Asn Leu Asp Asp Asn Lys Gly Leu Gly Lys Ala His
 50                  55                  60

Ala Val Gly Asp Thr Thr Ile Thr Ala Thr Leu Gly Lys Val Ser Gly
 65                  70                  75                  80

Lys Thr Trp Leu Thr Val
                85
```

<210> SEQ ID NO 24
<211> LENGTH: 86
<212> TYPE: PRT
<213> ORGANISM: Leptospira interrogans

<400> SEQUENCE: 24

```
Val Leu Thr Ser Ile Gln Ile Asn Pro Val Asn Pro Ser Leu Ala Lys
  1               5                  10                  15

Gly Leu Thr Gln Lys Phe Ser Ala Thr Gly Ile Tyr Ser Asp Asn Ser
                20                  25                  30
```

-continued

Asn Lys Asp Ile Thr Ser Ala Val Thr Trp Phe Ser Ser Asp Ser Ser
    35                  40                  45

Ile Ala Thr Ile Ser Asn Ala Gln Lys Asn Gln Gly Asn Ala Tyr Gly
 50                55                  60

Ala Ala Thr Gly Ala Thr Asp Ile Lys Ala Thr Phe Gly Lys Val Ser
65                70                  75                  80

Ser Pro Val Ser Thr Leu
              85

<210> SEQ ID NO 25
<211> LENGTH: 88
<212> TYPE: PRT
<213> ORGANISM: Leptospira interrogans

<400> SEQUENCE: 25

Lys Leu Val Glu Ile Gln Ile Thr Pro Ala Ala Ser Lys Ala Lys
1            5                  10                15

Gly Leu Thr Glu Arg Phe Lys Ala Thr Gly Ile Phe Thr Asp Asn Ser
              20                  25                30

Asn Ser Asp Ile Thr Asn Gln Val Thr Trp Asn Ser Ser Asn Thr Asp
            35                  40                45

Ile Ala Glu Ile Thr Asn Thr Ser Gly Ser Lys Gly Ile Thr Asn Thr
 50                55                  60

Leu Thr Pro Gly Ser Ser Glu Ile Ser Ala Ala Leu Gly Ser Ile Lys
65                70                  75                  80

Ser Ser Lys Val Ile Leu Lys Val
              85

<210> SEQ ID NO 26
<211> LENGTH: 84
<212> TYPE: PRT
<213> ORGANISM: Leptospira interrogans

<400> SEQUENCE: 26

Gln Leu Ile Ser Ile Ala Val Thr Pro Ile Asn Pro Ser Val Ala Lys
1            5                  10                15

Gly Leu Ile Arg Gln Phe Lys Ala Thr Gly Thr Tyr Thr Asp His Ser
              20                  25                30

Val Gln Asp Val Thr Ala Leu Ala Thr Trp Ser Ser Ser Asn Pro Arg
            35                  40                45

Lys Ala Met Val Asn Asn Val Thr Gly Ser Val Thr Thr Val Ala Thr
 50                55                  60

Gly Asn Thr Asn Ile Lys Ala Thr Ile Asp Ser Ile Ser Gly Ser Ser
65                70                  75                  80

Val Leu Asn Val

<210> SEQ ID NO 27
<211> LENGTH: 86
<212> TYPE: PRT
<213> ORGANISM: Leptospira interrogans

<400> SEQUENCE: 27

Leu Leu Thr Ser Ile Glu Ile Thr Pro Thr Ile Asn Ser Ile Thr His
1            5                  10                15

Gly Leu Thr Lys Gln Phe Lys Ala Thr Gly Ile Phe Ser Asp Lys Ser
              20                  25                30

Thr Gln Asn Leu Thr Gln Leu Val Thr Trp Ile Ser Ser Asp Pro Ser
            35                  40                45

```
Lys Ile Glu Ile Glu Asn Thr Ser Gly Lys Lys Gly Ile Ala Thr Ala
 50                  55                  60

Ser Lys Leu Gly Ser Ser Asn Ile Lys Ala Val Tyr Lys Phe Ile Gln
 65                  70                  75                  80

Ser Ser Pro Ile Pro Ile
                 85

<210> SEQ ID NO 28
<211> LENGTH: 86
<212> TYPE: PRT
<213> ORGANISM: Leptospira interrogans

<400> SEQUENCE: 28

Lys Leu Lys Ser Ile Thr Ile Ser Pro Ser Ser Ser Ile Ala Lys
 1               5                  10                  15

Gly Leu Thr Gln Gln Phe Lys Ala Ile Gly Thr Phe Ile Asp Gly Ser
                 20                  25                  30

Glu Gln Glu Ile Thr Asn Leu Val Thr Trp Tyr Ser Ser Lys Ser Asp
             35                  40                  45

Val Ala Pro Ile Asn Asn Ala Ala Asn Glu Lys Gly Leu Ala Thr Ala
 50                  55                  60

Leu Ser Ile Gly Ser Ser Asp Ile Tyr Ala Ile Tyr Asn Ser Ile Ser
 65                  70                  75                  80

Ser Asn Lys Ile Asn Phe
                 85

<210> SEQ ID NO 29
<211> LENGTH: 87
<212> TYPE: PRT
<213> ORGANISM: Leptospira interrogans

<400> SEQUENCE: 29

Thr Leu Asp Ser Ile Lys Ile Asn Pro Val Asn Asn Ile Ala Lys
 1               5                  10                  15

Gly Leu Thr Gln Gln Tyr Thr Ala Leu Gly Val Tyr Ser Asp Ser Thr
                 20                  25                  30

Ile Gln Asp Ile Ser Asp Ser Val Thr Trp Ser Ser Ser Asn Ser Ser
             35                  40                  45

Ser Ile Ser Ile Ser Asn Ser Thr Glu Thr Lys Gly Lys Ala Thr Ala
 50                  55                  60

Leu Gln Ile Gly Asn Ser Lys Ile Thr Ala Thr Tyr Asn Ser Ile Ser
 65                  70                  75                  80

Glu Asn Ile Asp Ile Thr Val
                 85

<210> SEQ ID NO 30
<211> LENGTH: 87
<212> TYPE: PRT
<213> ORGANISM: Leptospira interrogans

<400> SEQUENCE: 30

Thr Leu Ser Ser Ile Ser Ile Ser Pro Ile Asn Thr Asn Ile Asn Thr
 1               5                  10                  15

Thr Val Ser Lys Gln Phe Phe Ala Val Gly Thr Tyr Ser Asp Gly Thr
                 20                  25                  30

Lys Ala Asp Leu Thr Ser Ser Val Thr Trp Ser Ser Ser Asn Gln Ser
             35                  40                  45

Gln Ala Lys Val Ser Asn Ala Ser Glu Thr Lys Gly Leu Val Thr Gly
 50                  55                  60
```

Ile Ala Ser Gly Asn Pro Thr Ile Ile Ala Thr Tyr Gly Ser Val Ser
65                  70                  75                  80

Gly Asn Thr Ile Leu Thr Val
                85

<210> SEQ ID NO 31
<211> LENGTH: 80
<212> TYPE: PRT
<213> ORGANISM: Unknown
<220> FEATURE:
<223> OTHER INFORMATION: Region_name = "pfam02368, Big_2, Bacterial
      Ig-like domain (group 2). This family consists of bacterial
      domains with an Ig-like fold. Members of this family are found in
      bacterial and phage surface proteins such as intimins.

<400> SEQUENCE: 31

Ala Val Thr Ser Val Thr Val Ser Pro Thr Val Ala Ser Leu Leu Lys
1               5                   10                  15

Gly Ala Thr Leu Gln Leu Thr Ala Thr Gly Thr Pro Ala Asp Ala Ser
                20                  25                  30

Asn Gly Lys Val Thr Trp Ser Ser Ser Asn Thr Ser Val Ala Thr Val
            35                  40                  45

Ser Asn Ser Thr Gly Leu Val Thr Ala Leu Ala Lys Gly Thr Ala Thr
    50                  55                  60

Ile Thr Ala Thr Ser Gly Asp Gly Asn Ser Ser Ala Thr Val Thr Val
65                  70                  75                  80

<210> SEQ ID NO 32
<211> LENGTH: 81
<212> TYPE: PRT
<213> ORGANISM: Unknown
<220> FEATURE:
<223> OTHER INFORMATION: Region_name= "smart00635, BID_2, Bacterial
      Ig-like domain 2."

<400> SEQUENCE: 32

Val Val Thr Ser Val Thr Val Thr Pro Thr Thr Ala Ser Val Ala Lys
1               5                   10                  15

Gly Ala Thr Leu Gln Leu Thr Ala Thr Val Thr Pro Ser Ser Ala Lys
                20                  25                  30

Val Thr Gly Lys Val Thr Trp Thr Ser Ser Asn Pro Ser Val Ala Thr
            35                  40                  45

Val Val Asn Ala Ser Gly Leu Thr Cys Thr Val Ala Ala Gly Thr
    50                  55                  60

Ala Thr Ile Thr Ala Thr Ser Gly Asp Gly Ser Ser Ala Thr Gly Val
65                  70                  75                  80

Thr

<210> SEQ ID NO 33
<211> LENGTH: 595
<212> TYPE: PRT
<213> ORGANISM: Leptospira interrogans

<400> SEQUENCE: 33

Leu Thr Val Ser Asn Thr Asn Ala Lys Arg Gly Leu Gly Ser Thr Leu
1               5                   10                  15

Lys Gln Gly Thr Val Lys Val Thr Ala Ser Met Gly Gly Ile Glu Asp
                20                  25                  30

Ser Val Asp Phe Thr Val Thr Gln Ala Thr Leu Thr Ser Ile Glu Val
            35                  40                  45

```
Ser Pro Thr Arg Ala Ser Ile Ala Lys Gly Met Thr Gln Lys Phe Thr
 50                  55                  60
Ala Thr Gly Ile Phe Thr Asp His Ser Lys Lys Asn Ile Thr Glu Gln
 65                  70                  75                  80
Val Thr Trp Lys Ser Ser Lys Ala Leu Ser Met Leu Asn Ala Pro
                 85                  90                  95
Gly Glu Glu Gly Thr Gly Lys Ala Ile Ala Val Gly Lys His Tyr Tyr
                100                 105                 110
Tyr Cys Asn Leu Arg Lys Thr Phe Arg Glu Asn Arg Tyr Tyr Arg Tyr
         115                 120                 125
Ser Arg Asn Ser Tyr Phe Asn Ser Asn Gln Ser Cys Lys Asn Ile Val
         130                 135                 140
Leu Val Lys Gly Leu Thr Glu Lys Phe Ser Ala Thr Gly Ile Tyr Ser
145                 150                 155                 160
Asp Asn Ser Ser Lys Asp Ile Thr Ser Ala Val Thr Trp His Ser Ser
                165                 170                 175
Asn Asn Ser Val Ala Thr Ile Ser Asn Thr Lys Gly Tyr Gln Gly Gln
                180                 185                 190
Ala His Gly Thr Gly Thr Gly Thr Val Asp Ile Lys Ala Thr Leu Gly
         195                 200                 205
Asn Val Ser Ser Gln Val Ser Arg Leu Ser Val Thr Ala Ala Glu Leu
         210                 215                 220
Ile Glu Ile Val Leu Asp Pro Thr Ser Ser His Lys Ala Lys Gly Leu
225                 230                 235                 240
Thr Glu Asn Phe Lys Ala Thr Gly Val Phe Thr Asp Asn Ser Thr Lys
                245                 250                 255
Asp Ile Thr Asp Gln Val Thr Trp Lys Ser Ser Lys Thr Ala Tyr Ala
                260                 265                 270
Lys Ile Ser Asn Ala Thr Gly Ser Lys Arg Val Val Asn Ala Ile Ser
         275                 280                 285
Lys Gly Thr Ser His Ile Ser Ala Thr Leu Gly Ser Ile Ser Ser Ala
         290                 295                 300
Asn Ala Thr Phe Gln Val Thr Pro Ala Lys Val Val Ser Ile Glu Val
305                 310                 315                 320
Ile Pro Asn Asn Ile Ser Phe Ala Lys Gly Asn Ser Tyr Gln Phe Lys
                325                 330                 335
Ala Thr Gly Ile Tyr Thr Asp His Ser Glu Ala Asp Ile Thr Glu Gln
                340                 345                 350
Val Thr Trp Ser Ser Ser Asn Pro Lys Ile Ala Ser Val Glu Asn Thr
         355                 360                 365
Phe Gly Ser Ala Gly Leu Val Asn Thr Thr Asn Ile Gly Ser Thr Asn
         370                 375                 380
Ile Thr Ala Lys Leu Ser Asp Thr Val Ser Gly Ala Ser Val Leu Asn
385                 390                 395                 400
Val Thr Pro Ala Leu Leu Arg Tyr Ile Met Ile Thr Pro Ser Tyr Ala
                405                 410                 415
Gly Ile Glu Lys Gly Tyr Thr Lys Gln Phe Ser Ala Ile Gly Thr Tyr
                420                 425                 430
Ser Asp Gln Ser Thr Lys Asp Leu Thr Glu Asp Val Thr Trp Phe Ser
         435                 440                 445
Ser Asn Pro Ser Ser Val Val Ile Glu Asn Thr Pro Gly Lys Lys Gly
         450                 455                 460
Leu Ala Phe Ala Ser Glu Leu Gly Glu Pro Asp Ile Thr Val Phe Tyr
465                 470                 475                 480
```

-continued

```
Asp His His Thr Gln Ser Ser Tyr Thr Pro Val Thr Val Thr Glu Ser
            485                 490                 495

Gly Ile Val Asn Ile Thr Ile Ser Leu Ser Ser Ile Ser Lys Thr Lys
        500                 505                 510

Gly Ser Thr His Gln Phe Lys Ala Thr Gly Lys Phe Glu Asn Gly Ala
    515                 520                 525

Glu Ile Asp Leu Thr Glu Leu Val Thr Trp Ser Ser Ser Asn Pro Thr
530                 535                 540

Val Val Ser Ile Ser Asn Val Asp Asp Glu Arg Gly Leu Ala Thr Ala
545                 550                 555                 560

Leu Ser Val Gly Ser Ser Lys Ile Ser Val Asp Tyr Asn Ser Ile Ser
                565                 570                 575

Ser Ser Ile Asp Phe Glu Val Thr Pro Glu Ile Leu Ala Ser Ile Lys
            580                 585                 590

Thr Glu Pro
        595

<210> SEQ ID NO 34
<211> LENGTH: 794
<212> TYPE: PRT
<213> ORGANISM: Leptospira interrogans

<400> SEQUENCE: 34

Ala Glu Ile Thr Asn Thr Ser Gly Ser Lys Gly Ile Thr Asn Thr Leu
1               5                   10                  15

Thr Pro Gly Ser Ser Glu Ile Ser Ala Ala Leu Gly Ser Ile Lys Ser
            20                  25                  30

Ser Lys Val Ile Leu Lys Val Thr Pro Ala Gln Leu Ile Ser Ile Ala
        35                  40                  45

Val Thr Pro Ile Asn Pro Ser Val Ala Lys Gly Leu Ile Arg Gln Phe
    50                  55                  60

Lys Ala Thr Gly Thr Tyr Thr Asp His Ser Val Gln Asp Val Thr Ala
65                  70                  75                  80

Leu Ala Thr Trp Ser Ser Ser Asn Pro Arg Lys Ala Met Val Asn Asn
                85                  90                  95

Val Thr Gly Ser Val Thr Thr Val Ala Thr Gly Asn Thr Asn Ile Lys
            100                 105                 110

Ala Thr Ile Asp Ser Ile Ser Gly Ser Ser Val Leu Asn Val Thr Pro
        115                 120                 125

Ala Leu Leu Thr Ser Ile Glu Ile Thr Pro Thr Asn Ser Ile Thr
    130                 135                 140

His Gly Leu Thr Lys Gln Phe Lys Ala Thr Gly Ile Phe Ser Asp Lys
145                 150                 155                 160

Ser Thr Gln Asn Leu Thr Gln Leu Val Thr Trp Ile Ser Ser Asp Pro
                165                 170                 175

Ser Lys Ile Glu Ile Glu Asn Thr Ser Gly Lys Lys Gly Ile Ala Thr
            180                 185                 190

Ala Ser Lys Leu Gly Ser Ser Asn Ile Lys Ala Val Tyr Lys Phe Ile
        195                 200                 205

Gln Ser Ser Pro Ile Pro Ile Thr Val Thr Asp Leu Lys Leu Lys Ser
    210                 215                 220

Ile Thr Ile Ser Pro Ser Ser Ser Ile Ala Lys Gly Leu Thr Gln
225                 230                 235                 240

Gln Phe Lys Ala Ile Gly Thr Phe Ile Asp Gly Ser Glu Gln Glu Ile
                245                 250                 255
```

```
Thr Asn Leu Val Thr Trp Tyr Ser Ser Lys Ser Asp Val Ala Pro Ile
            260                 265                 270

Asn Asn Ala Ala Asn Glu Lys Gly Leu Ala Thr Ala Leu Ser Ile Gly
            275                 280                 285

Ser Ser Asp Ile Tyr Ala Ile Tyr Asn Ser Ile Ser Ser Asn Lys Ile
            290                 295                 300

Asn Phe Asn Val Ser Ala Ala Thr Leu Asp Ser Ile Lys Ile Asn Pro
305                 310                 315                 320

Val Asn Asn Ile Ala Lys Gly Leu Thr Gln Gln Tyr Thr Ala Leu
            325                 330                 335

Gly Val Tyr Ser Asp Ser Thr Ile Gln Asp Ile Ser Asp Ser Val Thr
            340                 345                 350

Trp Ser Ser Ser Asn Ser Ser Ser Ile Ser Ile Ser Asn Ser Thr Glu
            355                 360                 365

Thr Lys Gly Lys Ala Thr Ala Leu Gln Ile Gly Asn Ser Lys Ile Thr
            370                 375                 380

Ala Thr Tyr Asn Ser Ile Ser Glu Asn Ile Asp Ile Thr Val Ser Ala
385                 390                 395                 400

Ala Thr Ile Ser Ser Ile Ser Ile Ser Pro Ile Asn Thr Asn Ile Asn
            405                 410                 415

Thr Thr Val Ser Lys Gln Phe Phe Ala Val Gly Thr Tyr Ser Asp Gly
            420                 425                 430

Thr Lys Ala Asp Leu Thr Ser Ser Val Thr Trp Ser Ser Ser Asn Gln
            435                 440                 445

Ser Gln Ala Lys Val Ser Asn Ala Ser Glu Thr Lys Gly Leu Val Thr
            450                 455                 460

Gly Ile Ala Ser Gly Asn Pro Thr Ile Ile Ala Thr Tyr Gly Ser Val
465                 470                 475                 480

Ser Gly Asn Thr Ile Leu Thr Val Asn Lys Thr Asp Thr Ile Ala Pro
            485                 490                 495

Thr Val Gln Ser Val Val Ser Leu Ser Pro Thr Thr Ile Gln Val Val
            500                 505                 510

Tyr Ser Glu Ser Ile Asn Asn Lys Glu Ala Leu Asp Leu Ser Asn Tyr
            515                 520                 525

Lys Ile Ile Asn Ser Ser Asn Phe Ile Gly His Cys Ser Asp Asn Thr
530                 535                 540

Asp Phe Asn Ser Asn Ser Gln Thr Ala Asp Phe Ser Leu Ser Ser Ile
545                 550                 555                 560

Lys Gly Ser Lys Asn Thr Phe Thr Ile Thr Leu Ser His Ser Gln Ile
            565                 570                 575

Leu Asn Lys Ser Tyr Thr Leu Val Val Asn Lys Gln Gly Ile His Asp
            580                 585                 590

Leu Ser Ser Ile Pro Asn Ser Leu Ser Cys Pro Asn Asn Ser Asp Phe
            595                 600                 605

Met Gly Lys Glu Gln Leu Lys Leu Thr Ser Ala Val Cys Asn Ser Leu
            610                 615                 620

Asn Gln Val Ile Val Ser Phe Ser Lys Pro Leu Tyr Ser Gly Lys Glu
625                 630                 635                 640

Val Thr Lys Ser Val Glu Cys Ser Asn Pro Ser Gln Cys Glu Ser Arg
            645                 650                 655

Tyr Lys Phe Ala Gly Val Ser Ser Leu Gly Ser Ile Thr Ser Val Arg
            660                 665                 670

Ile Leu Asp Gly Lys Val Cys Gly Gly Ala Pro Ala Asp Ser Ser Lys
```

```
                 675                 680                 685
Ile Cys Leu Thr His Ser Leu Leu Gln Ser Gly Gln Tyr Thr Ile
    690                 695                 700

Ile Ala Ala Asn Asp Leu Asn Gly Asp Gly Phe Asp Asn Lys Ser Trp
705                 710                 715                 720

Gly Ala Ile Arg Asp Ser Phe Asp Gln Glu Asn Leu Gln Pro Ser Pro
                725                 730                 735

Lys Asp Arg Ile Asn Phe Ile Gly Cys Gly Asn Ser Pro Leu Asn Phe
            740                 745                 750

Met Asp Gly Pro Ile Val Ser Asp Pro Phe Gly Asp Gly Ser Asp Phe
        755                 760                 765

Gly Ser Leu Val Asp Tyr Asn Asn Gln Ile Tyr Leu Gly Pro Asn Val
    770                 775                 780

Lys Gly Asn Gln Ala Asn Ser Ile Pro Leu
785                 790
```

```
<210> SEQ ID NO 35
<211> LENGTH: 27
<212> TYPE: DNA
<213> ORGANISM: Artificial Sequence
<220> FEATURE:
<223> OTHER INFORMATION: A synthetic primer

<400> SEQUENCE: 35
gggtttcata tggctggcaa aagaggc                                        27

<210> SEQ ID NO 36
<211> LENGTH: 23
<212> TYPE: DNA
<213> ORGANISM: Artificial Sequence
<220> FEATURE:
<223> OTHER INFORMATION: A synthetic primer

<400> SEQUENCE: 36
ccctcgagtg gctccgtttt aat                                           23

<210> SEQ ID NO 37
<211> LENGTH: 22
<212> TYPE: DNA
<213> ORGANISM: Artificial Sequence
<220> FEATURE:
<223> OTHER INFORMATION: A synthetic primer

<400> SEQUENCE: 37
tcgaggtctc tccagtttta cc                                            22

<210> SEQ ID NO 38
<211> LENGTH: 28
<212> TYPE: DNA
<213> ORGANISM: Artificial Sequence
<220> FEATURE:
<223> OTHER INFORMATION: A synthetic primer

<400> SEQUENCE: 38
gcggatcctg ttttcatgtt atggctcc                                      28

<210> SEQ ID NO 39
<211> LENGTH: 24
<212> TYPE: DNA
<213> ORGANISM: Artificial Sequence
<220> FEATURE:
<223> OTHER INFORMATION: A synthetic primer

<400> SEQUENCE: 39
```

-continued

```
ggaattcatg ttaaagtcac tgct                                            24
```

<210> SEQ ID NO 40
<211> LENGTH: 23
<212> TYPE: DNA
<213> ORGANISM: Artificial Sequence
<220> FEATURE:
<223> OTHER INFORMATION: A synthetic primer

<400> SEQUENCE: 40

```
ccgctcgagg ttttaataga ggc                                             23
```

<210> SEQ ID NO 41
<211> LENGTH: 5
<212> TYPE: PRT
<213> ORGANISM: Leptospira interrogans

<400> SEQUENCE: 41

Ala Lys Glu Leu Thr
 1               5

<210> SEQ ID NO 42
<211> LENGTH: 9
<212> TYPE: PRT
<213> ORGANISM: Leptospira interrogans

<400> SEQUENCE: 42

Lys Glu Ala Leu Asp Leu Ser Asn Tyr
 1               5

<210> SEQ ID NO 43
<211> LENGTH: 17
<212> TYPE: PRT
<213> ORGANISM: Leptospira interrogans

<400> SEQUENCE: 43

Ile Ile Gly Ser Val Lys Leu Ile Val Thr Pro Ala Ala Leu Val Ser
 1               5                  10                  15

Ile

<210> SEQ ID NO 44
<211> LENGTH: 4
<212> TYPE: PRT
<213> ORGANISM: Leptospira interrogans

<400> SEQUENCE: 44

Trp Ile Gly Leu
 1

<210> SEQ ID NO 45
<211> LENGTH: 6014
<212> TYPE: DNA
<213> ORGANISM: Leptospira interrogans

<400> SEQUENCE: 45

```
tagaatatac tttgttttta taaattttaa aatgttttta tttaaaaact ttttacatcc      60
aataaatctc aagagaactt ctataaaatt aattttgtt gatagtcgcc aaacaacgac     120
ttgatgcaaa atctaattg dataattatc cttttaaat tttgtagagg ctctcaataa     180
ataaacacag caaatacaca aaatgaaaac ttcaaataaa acaattagag tgagtgttta     240
tgaagaaaat atttgtatt tcgattttc tttcgatgtt ttttcaaagt tgtatgtctt      300
ggccactttt aaccagtcta gcgggtttag cagctggcaa aagaggcgga gattcatctt     360
```

```
ttttccacct tctgttaggt aacttcaatc cgactattac aagaatcgaa ctcagttatc    420
aagattcttc tatcgcaaac ggtaccagta cagccctaga agttaccgca atctttgata    480
acggaacaaa tcagaatatt acggattcga catacatcgt ccccgattcc caatccgttg    540
taaccatcca aggtaacaga gtcagaggaa tcacttctgg ttcttccatt ataaaagcag    600
aatataacgg cctgtactct gaacaaaaaa ttacagttac accagccatt cttaactcaa    660
ttcaagttac gagtttagag tcaggtatac tacctaaagg tactaatcgt caattatcag    720
ccatcggtat cttttcggat ggttctcatc aggatatttc caacgatcca ttgatcgttt    780
ggtcctccag taatcctgat ttggttcaag tagatgattc agggttggca tcagggatca    840
atttaggaac agctcatatt cgtgcatcct ttcaatcaaa acaaggggct gaagaaatga    900
ccgttggaga tgctgttctt tctcaaatcc aagtaacttc aaacaatctg aatattcctc    960
tcggaaaaaa acaaaaacta acagctacgg aatctattc ggataactct aacagggata   1020
tttcctcttc tgttatctgg aattcttcta attccactat cgctaatatt caaaacaacg   1080
gaatattaga aacagctgat actggtattg tcactgtttc tgcttctacc gagaatataa   1140
taggctccgt aaaactaatc gttactccag cagccttagt ttctatttct gtttctccga   1200
caaattctac agttgcaaaa ggtttacaag aaaactttaa agctacaggg atctttacag   1260
ataattcaaa ctcggatatt accgaccaag ttacttggga ttcttctaat accgatattc   1320
tctcaatttc caatgcaagt gatagccacg gattagcttc cacactcaac caaggaaatg   1380
ttaaagtcac tgcttccatc ggtggaatac aaggatccac tgattttaaa gttacacaag   1440
aggtattaac ttccatcgaa gtttctccaa ctcgtacttc cattgcaaaa ggactaactc   1500
aaaagtttac tgcgatcggg atttttacgg ataactctaa aaaggatatt acggatcaag   1560
tcacttggaa ttcttcttca gcaatcgtaa gcgtgtctaa cttagacgac aataaaggtc   1620
tgggaaaagc tcacgctgtt ggagacacta cgattaccgc aaccttagga aaagttgcag   1680
gtaaaacttg gcttactgta gttcctgcgg ttctcacttc tattcaaatc aatcctgtaa   1740
atccttctct tgcaaaaggg ttaactcaaa aatttacggc tactgggatc tactctgaca   1800
actctaacaa ggacatcact tccgctgtta cgtggttctc atccgattct tcaatcgcga   1860
cgatttcaaa cgcccaaaaa aatcaaggaa acgcttacgg agcagctaca ggaacaacgg   1920
atattaaagc cacattcgga aaggtaagta gtccggtttc tacgttatcc gttacagctg   1980
caaaacttgt tgaaatccaa atcacaccgg ctgctgcttc caaagcaaaa ggactcacag   2040
aaagattcaa ggctactggt atctttacgg acaactcaaa ttccgatatt acaaatcaag   2100
ttacttggaa ttcctctaat acggatattg ctgaaattaa aaataccagt ggaagtaaag   2160
gtattacaaa tacactcact ccaggatcga gtgaaatatc cgcagccctc ggttcaatca   2220
aaagttctaa agtaatttta aaggtaactc cggcacaatt gatttccatt gccgtaacac   2280
ctataaatcc gtcagttgca aaaggtctaa tacgacaatt taaagccacc ggaacatata   2340
cggatcattc cgtacaagac gtgactgccc tagctacctg gtcttcttcc aatcccggaa   2400
aagcaatggt taacaacgtt acaggttcgg ttacaacagt ggctaccgga aatacaaata   2460
ttaaagcaac gatagactcc atatccggct cttccgtttt gaatgtcact cctgcacttc   2520
ttacttctat cgagataaca ccgacgatta actctatcac tcacggtctt acaaaacaat   2580
ttaaagcgac tggtatcttt tcagataaat ctactcaaaa tttgactcag cttgtaactt   2640
ggatttcttc cgatccatct aagattgaga tcgaaaacac ttccggtaaa aaaggtatag   2700
cgacagcctc taaattagga agttcgaata ttaaggccgt ctacaaattt gtccaaagct   2760
```

```
ccccaattcc gattacagtc actgacttaa aactgaaaag tataactatc agtccttcct    2820
caagttcaat agccaaagga ttgacccagc aatttaaagc gatcggaact tttatagatg    2880
gctctgaaca agaaattacg aatcttgtga cctggtattc ttccaaatcc gacgttgccc    2940
ctatcaataa cgctgccaat gcaaaaggtt tagcaaccgc actttcaata ggttcttcca    3000
acatctctgc gatttacaat tctataagca gtaataaaat aaattttaat gtaagtgctg    3060
ccacgttaga ttccattaaa atcaaccccg tcaataacaa cattgcgaaa gggcttacac    3120
aacaatatac tgcgctcggt gtttattcag actccaccat tcaggacatc agcgattcag    3180
ttacctggtc tagctccaat tcttcctcaa ttagtatttc caattcgacc gaaaccaagg    3240
gaaaagcgac cgctttacag attggaagga gcaaaatcac tgcgacttac aattccatct    3300
cggaaaacat agacataacg gtcagcgcag caacccttc ttcgatttca atatctccta    3360
tcaatacaaa tataaacgca accgtatcaa aacaattttt cgcgatggga acgtattcgg    3420
atgggaccaa agcggattta acttcttcgg ttacatggtc cagctcaaat aaatctcagt    3480
caaaggtgag taacgcatct aaaacgaaag gattggttac agggattgct tctggaaact    3540
ctataatcac agcgacctac ggttcagtat ctggaaatac aattctcaca gtaaacaaaa    3600
cggacacgat agctccaacg gttcaatcgg tagtttcttt atcacctact accatccaag    3660
ttgtatattc agaatccata aacaataagg aagcccttga tttatccaat tacaaaataa    3720
ttaatagttc caattttata ggacattgtt cagataatac ggacttcaat tccaattctc    3780
aaaccgcaga ttttctctt agtagtatca aaggaagtaa aaatacttttt acgatcacac    3840
tttcacattc acaaatctta aacaaatcat acacacttgt agtcaacaaa caaggaattc    3900
acgatctttc ttccattcca aattccttaa gttgtccaaa taactctgat tttataggaa    3960
aagaacaact caaacttaca agtgcagttt gtaattcctt aaaccaagtg atcgtttctt    4020
tttccaaacc tttatattca ggaaaggaag caacaaaatc cgtggaatgt tcaaatccgt    4080
cccagtgtga atccagatat aaatttgcag gtgtgtcttc attgggaagt attacgagcg    4140
ttagaatttt agatggaaaa gtatgcggtg gagcgccggc agactcctcg aaaatatgtt    4200
taacacactc ccttcttcaa tcaggtggtc aatatacgat catcgccgca aatgatttga    4260
acggagacgg ctttgacaac aaatcctggg gagcaattcg agattcattc gatcaagaaa    4320
acctacaatc ttctccgaaa gatagaatca actttatagg ttgtggaaat tcccctctca    4380
actttatgga tggcccgatc gtgtcagatc cttttggaga cggttccgat ttcggctttc    4440
ttgtagatta caacaatcaa atctatctag gaccgaatgt aaaaggaaac caagcagctc    4500
gattcaatta cgacggaact tttccggaat ctattttctt ttcttttacc caagatataa    4560
atgccactaa ccgtgcttcc tcaagagatg gaggtatccc ggttccgaat tacgttacga    4620
tcggtcatac cggttgtact ctcaatagtc cagacatcac tactggatgt ggtccggata    4680
acgaagatgg acgtggggtt tttgccaccg gatcattaga taaaaaatct catattttta    4740
tagcaggttc aaaaccaaag agcttcaact atctctatta ttcctcagat accgatacaa    4800
accttaattt taaatatatc agtatgggaa aaattactgg attggcgact gcaggaactt    4860
catctatcgc agttctagac gatcggatcc atgtgggttt tgcaaaaaaa aatcaaaatc    4920
taaacgcacc tgatttcggt aaaatcaccct ttaatacatc cgagcacaat cgatgtgcaa    4980
ttgtaaacaa ctgtgaagcc tctgacggat accgcggtaa tcgtttttaga atcgatagaa    5040
tgccttactt tggcggcggc tccgtggatg tagtcaatta tagatcttat aaatctgata    5100
actcctcgat catgccttac tttggcggcg gctccgtgga tgtagtcaat tatagatctt    5160
```

```
ataaatctga taactcctcg atcattccaa attcactaca taatggaagt ataatacact    5220
ctaccagtgc aaatcctagt ccttgtgagg ggatcaatcg ttgttccagt tggaaagaca    5280
cagcacctag atccaatcca aagtggcata actctcctca taacaattgg ttttcactgg    5340
agcttacaaa gtatcggaat ttaattccgg cggataaagc attctctcaa ttcgcagaat    5400
ttaacggaag attgtatgta acaagaacga tctgcgtaac gaaagaagat cactccggac    5460
tcagacaaag tttacaaact gtgaaaggtt gtacggacgg aagttataca aatcgaagac    5520
cccaactttg gaaatgtgat ccgactctaa ccggcgatac aacaacctgt gaagcagaag    5580
attggtcttt agtaggagat aatggaaccg ggtttacaaa ctttggagac aattccaatc    5640
acagtatgac gatgatggtt gcaagtggat cttatctcta cataggtttt gataacgaaa    5700
acggaattca atctggaga acaaatcttg aaaatccggg aagttcatca cacaactggg    5760
agcctatagg aataggtgga ttaagagacg ttaccaatcg tcaaatttat tcggctatat    5820
ccggaatgaa ttttggtgta aatttcgtat atataagcgt aggaaacaaa aataaaccgg    5880
tcaaaattta cagacaacag aatcaataat atgcaaaatt cattaagaat catcgtgacg    5940
ataatggctt gtatgtttac cggattaatc tcctgtaaaa taaacgaaaa ttcagaaagg    6000
cttatattcg atca                                                     6014
```

<210> SEQ ID NO 46
<211> LENGTH: 1889
<212> TYPE: PRT
<213> ORGANISM: Leptospira interrogans

<400> SEQUENCE: 46

```
Met Lys Lys Ile Phe Cys Ile Ser Ile Phe Leu Ser Met Phe Phe Gln
  1               5                  10                  15

Ser Cys Met Ser Trp Pro Leu Leu Thr Ser Leu Ala Gly Leu Ala Ala
             20                  25                  30

Gly Lys Arg Gly Gly Asp Ser Ser Phe Phe His Leu Leu Leu Gly Asn
         35                  40                  45

Phe Asn Pro Thr Ile Thr Arg Ile Glu Leu Ser Tyr Gln Asp Ser Ser
     50                  55                  60

Ile Ala Asn Gly Thr Ser Thr Ala Leu Glu Val Thr Ala Ile Phe Asp
 65                  70                  75                  80

Asn Gly Thr Asn Gln Asn Ile Thr Asp Ser Thr Tyr Ile Val Pro Asp
                 85                  90                  95

Ser Gln Ser Val Val Thr Ile Gln Gly Asn Arg Val Arg Gly Ile Thr
            100                 105                 110

Ser Gly Ser Ser Ile Ile Lys Ala Glu Tyr Asn Gly Leu Tyr Ser Glu
        115                 120                 125

Gln Lys Ile Thr Val Thr Pro Ala Ile Leu Asn Ser Ile Gln Val Thr
    130                 135                 140

Ser Leu Glu Ser Gly Ile Leu Pro Lys Gly Thr Asn Arg Gln Leu Ser
145                 150                 155                 160

Ala Ile Gly Ile Phe Ser Asp Gly Ser His Gln Asp Ile Ser Asn Asp
                165                 170                 175

Pro Leu Ile Val Trp Ser Ser Asn Pro Asp Leu Val Gln Val Asp
            180                 185                 190

Asp Ser Gly Leu Ala Ser Gly Ile Asn Leu Gly Thr Ala His Ile Arg
        195                 200                 205

Ala Ser Phe Gln Ser Lys Gln Gly Ala Glu Glu Met Thr Val Gly Asp
    210                 215                 220
```

```
Ala Val Leu Ser Gln Ile Gln Val Thr Ser Asn Asn Leu Asn Ile Pro
225                 230                 235                 240

Leu Gly Lys Lys Gln Lys Leu Thr Ala Thr Gly Ile Tyr Ser Asp Asn
            245                 250                 255

Ser Asn Arg Asp Ile Ser Ser Val Ile Trp Asn Ser Asn Ser
        260                 265                 270

Thr Ile Ala Asn Ile Gln Asn Asn Gly Ile Leu Glu Thr Ala Asp Thr
        275                 280                 285

Gly Ile Val Thr Val Ser Ala Ser Thr Glu Asn Ile Ile Gly Ser Val
    290                 295                 300

Lys Leu Ile Val Thr Pro Ala Ala Leu Val Ser Ile Ser Val Ser Pro
305                 310                 315                 320

Thr Asn Ser Thr Val Ala Lys Gly Leu Gln Glu Asn Phe Lys Ala Thr
                325                 330                 335

Gly Ile Phe Thr Asp Asn Ser Asn Ser Asp Ile Thr Asp Gln Val Thr
            340                 345                 350

Trp Asp Ser Ser Asn Thr Asp Ile Leu Ser Ile Ser Asn Ala Ser Asp
        355                 360                 365

Ser His Gly Leu Ala Ser Thr Leu Asn Gln Gly Asn Val Lys Val Thr
    370                 375                 380

Ala Ser Ile Gly Gly Ile Gln Gly Ser Thr Asp Phe Lys Val Thr Gln
385                 390                 395                 400

Glu Val Leu Thr Ser Ile Glu Val Ser Pro Thr Arg Thr Ser Ile Ala
                405                 410                 415

Lys Gly Leu Thr Gln Lys Phe Thr Ala Ile Gly Ile Phe Thr Asp Asn
            420                 425                 430

Ser Lys Lys Asp Ile Thr Asp Gln Val Thr Trp Asn Ser Ser Ser Ala
        435                 440                 445

Ile Val Ser Val Ser Asn Leu Asp Asp Asn Lys Gly Leu Gly Lys Ala
    450                 455                 460

His Ala Val Gly Asp Thr Thr Ile Thr Ala Thr Leu Gly Lys Val Ala
465                 470                 475                 480

Gly Lys Thr Trp Leu Thr Val Val Pro Ala Val Leu Thr Ser Ile Gln
                485                 490                 495

Ile Asn Pro Val Asn Pro Ser Leu Ala Lys Gly Leu Thr Gln Lys Phe
            500                 505                 510

Thr Ala Thr Gly Ile Tyr Ser Asp Asn Ser Asn Lys Asp Ile Thr Ser
        515                 520                 525

Ala Val Thr Trp Phe Ser Ser Asp Ser Ser Ile Ala Thr Ile Ser Asn
    530                 535                 540

Ala Gln Lys Asn Gln Gly Asn Ala Tyr Gly Ala Ala Thr Gly Thr Thr
545                 550                 555                 560

Asp Ile Lys Ala Thr Phe Gly Lys Val Ser Ser Pro Val Ser Thr Leu
                565                 570                 575

Ser Val Thr Ala Ala Lys Leu Val Glu Ile Gln Ile Thr Pro Ala Ala
            580                 585                 590

Ala Ser Lys Ala Lys Gly Leu Thr Glu Arg Phe Lys Ala Thr Gly Ile
        595                 600                 605

Phe Thr Asp Asn Ser Asn Ser Asp Ile Thr Asn Gln Val Thr Trp Asn
    610                 615                 620

Ser Ser Asn Thr Asp Ile Ala Glu Ile Lys Asn Thr Ser Gly Ser Lys
625                 630                 635                 640

Gly Ile Thr Asn Thr Leu Thr Pro Gly Ser Ser Glu Ile Ser Ala Ala
```

```
                    645                 650                 655
Leu Gly Ser Ile Lys Ser Ser Lys Val Ile Leu Lys Val Thr Pro Ala
                660                 665                 670

Gln Leu Ile Ser Ile Ala Val Thr Pro Ile Asn Pro Ser Val Ala Lys
                675                 680                 685

Gly Leu Ile Arg Gln Phe Lys Ala Thr Gly Thr Tyr Thr Asp His Ser
                690                 695                 700

Val Gln Asp Val Thr Ala Leu Ala Thr Trp Ser Ser Asn Pro Gly
705                 710                 715                 720

Lys Ala Met Val Asn Asn Val Thr Gly Ser Val Thr Thr Val Ala Thr
                725                 730                 735

Gly Asn Thr Asn Ile Lys Ala Thr Ile Asp Ser Ile Ser Gly Ser Ser
                740                 745                 750

Val Leu Asn Val Thr Pro Ala Leu Leu Thr Ser Ile Glu Ile Thr Pro
                755                 760                 765

Thr Ile Asn Ser Ile Thr His Gly Leu Thr Lys Gln Phe Lys Ala Thr
                770                 775                 780

Gly Ile Phe Ser Asp Lys Ser Thr Gln Asn Leu Thr Gln Leu Val Thr
785                 790                 795                 800

Trp Ile Ser Ser Asp Pro Ser Lys Ile Glu Ile Glu Asn Thr Ser Gly
                805                 810                 815

Lys Lys Gly Ile Ala Thr Ala Ser Lys Leu Gly Ser Ser Asn Ile Lys
                820                 825                 830

Ala Val Tyr Lys Phe Val Gln Ser Ser Pro Ile Pro Ile Thr Val Thr
                835                 840                 845

Asp Leu Lys Leu Lys Ser Ile Thr Ile Ser Pro Ser Ser Ser Ile
                850                 855                 860

Ala Lys Gly Leu Thr Gln Gln Phe Lys Ala Ile Gly Thr Phe Ile Asp
865                 870                 875                 880

Gly Ser Glu Gln Glu Ile Thr Asn Leu Val Thr Trp Tyr Ser Ser Lys
                885                 890                 895

Ser Asp Val Ala Pro Ile Asn Asn Ala Ala Asn Ala Lys Gly Leu Ala
                900                 905                 910

Thr Ala Leu Ser Ile Gly Ser Ser Asn Ile Ser Ala Ile Tyr Asn Ser
                915                 920                 925

Ile Ser Ser Asn Lys Ile Asn Phe Asn Val Ser Ala Ala Thr Leu Asp
                930                 935                 940

Ser Ile Lys Ile Asn Pro Val Asn Asn Asn Ile Ala Lys Gly Leu Thr
945                 950                 955                 960

Gln Gln Tyr Thr Ala Leu Gly Val Tyr Ser Asp Ser Thr Ile Gln Asp
                965                 970                 975

Ile Ser Asp Ser Val Thr Trp Ser Ser Ser Asn Ser Ser Ser Ile Ser
                980                 985                 990

Ile Ser Asn Ser Thr Glu Thr Lys Gly Lys Ala Thr Ala Leu Gln Ile
                995                1000                1005

Gly Lys Ser Lys Ile Thr Ala Thr Tyr Asn Ser Ile Ser Glu Asn Ile
                1010                1015                1020

Asp Ile Thr Val Ser Ala Ala Thr Leu Ser Ser Ile Ser Ile Ser Pro
1025                1030                1035                1040

Ile Asn Thr Asn Ile Asn Ala Thr Val Ser Lys Gln Phe Phe Ala Met
                1045                1050                1055

Gly Thr Tyr Ser Asp Gly Thr Lys Ala Asp Leu Thr Ser Ser Val Thr
                1060                1065                1070
```

-continued

```
Trp Ser Ser Ser Asn Lys Ser Gln Ser Lys Val Ser Asn Ala Ser Lys
    1075                1080                1085

Thr Lys Gly Leu Val Thr Gly Ile Ala Ser Gly Asn Ser Ile Ile Thr
    1090                1095                1100

Ala Thr Tyr Gly Ser Val Ser Gly Asn Thr Ile Leu Thr Val Asn Lys
1105                1110                1115                1120

Thr Asp Thr Ile Ala Pro Thr Val Gln Ser Val Val Ser Leu Ser Pro
            1125                1130                1135

Thr Thr Ile Gln Val Val Tyr Ser Glu Ser Ile Asn Asn Lys Glu Ala
            1140                1145                1150

Leu Asp Leu Ser Asn Tyr Lys Ile Ile Asn Ser Ser Asn Phe Ile Gly
            1155                1160                1165

His Cys Ser Asp Asn Thr Asp Phe Asn Ser Asn Ser Gln Thr Ala Asp
            1170                1175                1180

Phe Ser Leu Ser Ser Ile Lys Gly Ser Lys Asn Thr Phe Thr Ile Thr
1185                1190                1195                1200

Leu Ser His Ser Gln Ile Leu Asn Lys Ser Tyr Thr Leu Val Val Asn
            1205                1210                1215

Lys Gln Gly Ile His Asp Leu Ser Ile Pro Asn Ser Leu Ser Cys
            1220                1225                1230

Pro Asn Asn Ser Asp Phe Ile Gly Lys Glu Gln Leu Lys Leu Thr Ser
            1235                1240                1245

Ala Val Cys Asn Ser Leu Asn Gln Val Ile Val Ser Phe Ser Lys Pro
            1250                1255                1260

Leu Tyr Ser Gly Lys Glu Ala Thr Lys Ser Val Glu Cys Ser Asn Pro
1265                1270                1275                1280

Ser Gln Cys Glu Ser Arg Tyr Lys Phe Ala Gly Val Ser Ser Leu Gly
            1285                1290                1295

Ser Ile Thr Ser Val Arg Ile Leu Asp Gly Lys Val Cys Gly Gly Ala
            1300                1305                1310

Pro Ala Asp Ser Ser Lys Ile Cys Leu Thr His Ser Leu Leu Gln Ser
            1315                1320                1325

Gly Gly Gln Tyr Thr Ile Ile Ala Ala Asn Asp Leu Asn Gly Asp Gly
            1330                1335                1340

Phe Asp Asn Lys Ser Trp Gly Ala Ile Arg Asp Ser Phe Asp Gln Glu
1345                1350                1355                1360

Asn Leu Gln Ser Ser Pro Lys Asp Arg Ile Asn Phe Ile Gly Cys Gly
            1365                1370                1375

Asn Ser Pro Leu Asn Phe Met Asp Gly Pro Ile Val Ser Asp Pro Phe
            1380                1385                1390

Gly Asp Gly Ser Asp Phe Gly Phe Leu Val Asp Tyr Asn Asn Gln Ile
            1395                1400                1405

Tyr Leu Gly Pro Asn Val Lys Gly Asn Gln Ala Ala Arg Phe Asn Tyr
            1410                1415                1420

Asp Gly Thr Phe Pro Glu Ser Ile Phe Phe Ser Phe Thr Gln Asp Ile
1425                1430                1435                1440

Asn Ala Thr Asn Arg Ala Ser Ser Arg Asp Gly Gly Ile Pro Val Pro
            1445                1450                1455

Asn Tyr Val Thr Ile Gly His Thr Gly Cys Thr Leu Asn Ser Ala Asp
            1460                1465                1470

Ile Thr Thr Gly Cys Gly Pro Asp Asn Glu Asp Gly Arg Gly Val Phe
            1475                1480                1485

Ala Thr Gly Ser Leu Asp Lys Lys Ser His Ile Phe Ile Ala Gly Ser
            1490                1495                1500
```

Lys Pro Lys Ser Phe Asn Tyr Leu Tyr Tyr Ser Ser Asp Thr Asp Thr
1505                1510                1515                1520

Asn Leu Asn Phe Lys Tyr Ile Ser Met Gly Lys Ile Thr Gly Leu Ala
            1525                1530                1535

Thr Ala Gly Thr Ser Ser Ile Ala Val Leu Asp Asp Arg Ile His Val
        1540                1545                1550

Gly Phe Ala Lys Lys Asn Gln Asn Leu Asn Ala Pro Asp Phe Gly Lys
    1555                1560                1565

Ile Thr Phe Asn Thr Ser Glu His Asn Arg Cys Ala Ile Val Asn Asn
1570                1575                1580

Cys Glu Ala Ser Asp Gly Tyr Arg Gly Asn Arg Phe Arg Ile Asp Arg
1585                1590                1595                1600

Met Pro Tyr Phe Gly Gly Ser Val Asp Val Val Asn Tyr Arg Ser
                1605                1610                1615

Tyr Lys Ser Asp Asn Ser Ser Ile Asn Trp Gly Tyr Tyr Val Gly Ile
            1620                1625                1630

Asp Ser Leu Phe Val Phe Lys Glu Lys Leu Tyr Ala Ala Asn Gly Gly
        1635                1640                1645

Phe Pro Asn Ser Leu His Asn Gly Ser Ile Ile His Ser Thr Ser Ala
    1650                1655                1660

Asn Pro Ser Pro Cys Glu Gly Ile Asn Arg Cys Ser Ser Trp Lys Asp
1665                1670                1675                1680

Thr Ala Pro Arg Ser Asn Pro Lys Trp His Asn Ser Pro His Asn Asn
            1685                1690                1695

Trp Phe Ser Leu Glu Leu Thr Lys Tyr Arg Asn Leu Ile Pro Ala Asp
        1700                1705                1710

Lys Ala Phe Ser Gln Phe Ala Glu Phe Asn Gly Arg Leu Tyr Val Thr
    1715                1720                1725

Arg Thr Ile Cys Val Thr Lys Glu Asp His Ser Gly Leu Arg Gln Ser
1730                1735                1740

Leu Gln Thr Val Lys Gly Cys Thr Asp Gly Ser Tyr Thr Asn Arg Arg
1745                1750                1755                1760

Pro Gln Leu Trp Lys Cys Asp Pro Thr Leu Thr Gly Asp Thr Thr Thr
            1765                1770                1775

Cys Glu Ala Glu Asp Trp Ser Leu Val Gly Asp Asn Gly Thr Gly Phe
        1780                1785                1790

Thr Asn Phe Gly Asp Asn Ser Asn His Ser Met Thr Met Met Val Ala
    1795                1800                1805

Ser Gly Ser Tyr Leu Tyr Ile Gly Phe Asp Asn Glu Asn Gly Ile Gln
1810                1815                1820

Ile Trp Arg Thr Asn Leu Glu Asn Pro Gly Ser Ser His Asn Trp
1825                1830                1835                1840

Glu Pro Ile Gly Ile Gly Gly Leu Arg Asp Val Thr Asn Arg Gln Ile
            1845                1850                1855

Tyr Ser Ala Ile Ser Gly Met Asn Phe Gly Val Asn Phe Val Tyr Ile
        1860                1865                1870

Ser Val Gly Asn Lys Asn Lys Pro Val Lys Ile Tyr Arg Gln Gln Asn
    1875                1880                1885

Gln

<210> SEQ ID NO 47
<211> LENGTH: 21
<212> TYPE: DNA
<213> ORGANISM: Artificial Sequence

```
<220> FEATURE:
<223> OTHER INFORMATION: A synthetic primer

<400> SEQUENCE: 47
tcccccgggg ctggcaaaag a                                              21

<210> SEQ ID NO 48
<211> LENGTH: 23
<212> TYPE: DNA
<213> ORGANISM: Artificial Sequence
<220> FEATURE:
<223> OTHER INFORMATION: A synthetic primer

<400> SEQUENCE: 48
ccctcgagaa tatccgtatt aga                                            23

<210> SEQ ID NO 49
<211> LENGTH: 19
<212> TYPE: DNA
<213> ORGANISM: Artificial Sequence
<220> FEATURE:
<223> OTHER INFORMATION: A synthetic primer

<400> SEQUENCE: 49
cccccgggct taccgttcc                                                 19

<210> SEQ ID NO 50
<211> LENGTH: 24
<212> TYPE: DNA
<213> ORGANISM: Artificial Sequence
<220> FEATURE:
<223> OTHER INFORMATION: A synthetic primer

<400> SEQUENCE: 50
tcccccgggg ctgaaattac aaat                                           24

<210> SEQ ID NO 51
<211> LENGTH: 27
<212> TYPE: DNA
<213> ORGANISM: Artificial Sequence
<220> FEATURE:
<223> OTHER INFORMATION: A synthetic primer

<400> SEQUENCE: 51
ccgctcgagt tggtttcctt ttacgtt                                        27

<210> SEQ ID NO 52
<211> LENGTH: 22
<212> TYPE: DNA
<213> ORGANISM: Artificial Sequence
<220> FEATURE:
<223> OTHER INFORMATION: A synthetic primer

<400> SEQUENCE: 52
gaaaatcgca tcagtagaaa ac                                             22

<210> SEQ ID NO 53
<211> LENGTH: 22
<212> TYPE: DNA
<213> ORGANISM: Artificial Sequence
<220> FEATURE:
<223> OTHER INFORMATION: A synthetic primer

<400> SEQUENCE: 53
taaacaaaac ggacacgata gc                                             22
```

IMMUNOGENIC PROTEINS OF *LEPTOSPIRA*

RELATED APPLICATION

This application is a divisional of U.S. patent application Ser. No. 11/102,476, filed Apr. 8, 2005, which is a continuation under 35 U.S.C. 111(a) of International Application No. PCT/US03/32385 filed Oct. 10, 2003 and published in English as WO 2004/032599 A3 on Apr. 22, 2004, which claims priority under 35 USC119(e) from U.S. Provisional Application Ser. No. 60/417,721, filed Oct. 10, 2002, which applications and publication are incorporated herein by reference.

BACKGROUND OF THE INVENTION

Leptospirosis is a worldwide zoonotic disease caused by gram-negative spirochetes belonging to the genus *Leptospira*. Leptospirosis is prevalent in humans, horses, cattle and wild animals. The disease occurs widely in developing countries, such as Brazil and India, and is re-emerging in developed countries. Although the incidence of leptospirosis in humans in the United States is relatively low, disease incidence in domestic animals has increased in recent years.

Manifestations and routes of *Leptospira* infection vary depending on the host. Humans, who contract leptospirosis either directly or indirectly through contact with infected animals or a contaminated environment, often develop kidney and liver failure (Schubert, G. E. et al., *Munch Med Wochenschr*, 113:80-86 (1971); Bain, B. J. et al., *Arch. Intern. Med.*, 131:740-745 (1973); Garcia, M. et al., *Med. Clin. (Barc)*, 73:362-366 (1979); San Segundo, D., *Med. Clin. (Barc)*, 78:28-31 (1982); Winearls, C. G. et al., *Q J Med.*, 53:487-495 (1984); Menzies, D. G. et al., *Scott Med. J.*, 34:410 (1989); Divers, T. J. et al., *J. Am. Vet. Med. Assoc.*, 201:1391-1392 (1992); Petros, S. et al., *Scand. J. Infect. Dis.*, 32:104-105 (2000); Kager, P. A. et al., *Ned Tijdschr Geneeskd*, 145:184-186 (2001)). *Leptospira* infection in humans can range in severity from an inapparent infection to death from renal or hepatic failure (Feigin, R. D. and D. C. Anderson, *CRC Crit. Rev. Clin. Lab. Sci.*, 5:413-467 (1975)). In addition to hepatic and renal failure, uveitis is sometimes a sequela to *Leptospira* infection (Rathinam, S. R. et al., *Am. J. Ophthalmol.*, 124:71-79 (1997)).

In animals such as horses, cattle, dogs and swine, infection causes abortion, still birth, renal failure, and uveitis (Akkermans, J. P., *Bull. Off. Int. Epizoot.*, 66:849-866 (1966); Ellis, W. A. et al., *Vet. Rec.*, 99:458-459 (1976); Ryan, T. J. et al., *NZ Vet. J.*, 25:352 (1977); Ellis, W. A. et al., *Vet. Rec.*, 103:237-239 (1978); Andreani, E. et al., *Br. Vet. J.*, 139:165-170 (1983); Ellis, W. A. et al., *Vet. Rec.*, 112:291-293 (1983); Elder, J. K. et al., *Aust. Vet. J.*, 62:258-262 (1985); Ellis, W. A. et al., *Vet. Rec.*, 118:294-295 (1986); Rocha, T., *Vet. Rec.*, 126:602 (1990); Bolin, C. A. et al., *J. Vet. Diagn. Invest.*, 3:152-154 (1991); Donahue, J. M. et al., *J. Vet. Diagn. Invest.*, 3:148-151 (1991); Christianson, W. T., *Vet. Clin. North Am. Food Anim. Pract.*, 8:623-639 (1992); Donahue, J. M. et al., *J. Vet. Diagn. Invest.*, 4:279-284 (1992); Bernard, W. V. et al., *J. Am. Vet. Med. Assoc.*, 202:1285-1286 (1993); Broll, S. et al., *Zentralbl Veterinarmed [B]*, 40:641-653 (1993); Donahue, J. M. et al., *J. Vet. Diagn. Invest.*, 7:87-91 (1995); Donahue, J. M. and Williams, N. M., *Vet. Clin. North Am. Equine Pract.*, 16:443-456 (2000)) and can result in multi-organ failure. In horses, the most common manifestations of infection are abortion and uveitis (Poonacha, K. B. et al., *Vet. Pathol.*, 30:362-369 (1993)). The association of leptospires with equine recurrent uveitis (ERU) (Halliwell, R. E. et al., *Curr. Eye Res.*, 4:1033-1040 (1985)) has been well documented and the organism has been detected in ocular fluids by culture and PCR (Roberts, S. J., *J. Amer. Vet. Med. Assoc.*, 175:803-808 (1958)). In addition, Parma et al. demonstrated reactivity of several bands in extracts of equine cornea and lens with anti-leptospiral sera by western blotting (Parma, A. E. et al., *Vet. Immunol. Immunopathol.*, 14:181-185 (1987); Parma, A. E. et al., *Vet. Immunol. Immunopathol.*, 10:215-224 (1985)). Although there is a strong association between leptospiral infection and uveitis, the immunopathogenesis of *Leptospira*-associated uveitis remains obscure.

Currently available leptospiral vaccines have low efficacy, are serovar specific and generally produce only short-term immunity in domestic livestock. In fact, these vaccines do not provide cross protection against the 250 known serovars of pathogenic *Leptospira*. Efforts to identify immunogenic components of value in vaccines have resulted in characterization of 31, 32, 36 and 41 kDa outer membrane proteins (Haake, D. A. et al., *J. Bacteriol.*, 175:4225-4234 (1993); Haake, D. A. et al., *Infect. Immun.*, 68:2276-2285 (2000); Haake, D. A. et al., *Infect. Immun.*, 66:1579-1587 (1998); Haake, D. A. et al., *Infect. Immun.*, 67:6572-6582 (1999); Shang, E. S. et al., *Infect. Immun.*, 65:3174-3181 (1995); Shang, E. S. et al., *Infect. Immun.*, 64:2322-2330 (1996)). Two of these proteins (31 and 41 kDa) function synergistically in immunoprotection of hamsters suggesting that an effective protein based vaccine would contain several components (Haake, D. A. et al., *Infect. Immun.*, 68:2276-2285 (2000)). The search for protective immunogens is complicated by the possibility that important components may be produced only during infection. Supporting this possibility are recent studies that indicate that some immunogenic proteins of *L. interrogans* serovar pomona are upregulated at 37° C. (Nally, J. E. et al., *Infect. Immun.*, 69:400-404 (2001)).

Thus, there is an ongoing need for novel immunogenic proteins of *Leptospira* to aid in the development of effective vaccines and antibodies, as well as improved diagnostic methods and kits.

SUMMARY OF THE INVENTION

The present invention provides an isolated and purified polynucleotide comprising a nucleic acid sequence encoding ligA from *Leptospira interrogans*. Also provided by the present invention is the polynucleotide comprising SEQ ID NO: 1.

The invention further provides an isolated and purified polynucleotide comprising a nucleic acid sequence encoding ligB from *Leptospira interrogans*. Also provided by the present invention is the polynucleotide comprising SEQ ID NO: 3 and SEQ ID NO: 45.

An isolated and purified polypeptide comprising a LigA polypeptide from *Leptospira interrogans* is provided by the present invention. The polypeptide comprising SEQ ID NO: 2 is also provided by the present invention.

The present invention provides an isolated and purified polypeptide comprising a LigB polypeptide from *Leptospira interrogans*. Further, the invention provides the polypeptide comprising SEQ ID NO: 4 and SEQ ID NO: 46.

The present invention provides a pharmaceutical composition comprising a purified polypeptide from *Leptospira*, and a pharmaceutically acceptable carrier, wherein the composition is capable of eliciting an immune response against *Leptospira interrogans*. The polypeptide in the pharmaceutical composition of the present invention may comprise the polypeptides LigA or LigB. The pharmaceutical composition of the present invention may also optionally comprise an effective amount of an immunological adjuvant.

The present invention provides a vaccine comprising an immunogenic amount of a purified polypeptide from *Leptospira*, wherein the polypeptide is present in an amount that is effective to immunize a susceptible mammal against *Leptospira* infection in combination with a physiologically acceptable, non-toxic vehicle.

The polypeptide in the vaccine of the present invention may be LigA or LigB. The vaccine may also comprise an effective amount of an immunological adjuvant, and may be administered orally, mucosally, or by subcutaneous or intramuscular injection.

Further provided by the present invention is a method of eliciting an immune response in a subject against *Leptospira interrogans*, comprising administering to a subject the pharmaceutical composition described hereinabove. Another method provided by the present invention is a method of preventing *Leptospira interrogans* infections comprising administering to a subject the pharmaceutical composition described hereinabove.

The present invention additionally provides a method of protecting a susceptible mammal against *Leptospira* infection or colonization comprising administering to the mammal an effective amount of a vaccine comprising an immunogenic amount of *Leptospira* protein LigA or LigB wherein the amount of LigA or LigB is effective to immunize the susceptible mammal against *Leptospira* in combination with a physiologically-acceptable, non-toxic vehicle.

The present invention provides a composition comprising an amount of an immunologically active protein comprising SEQ ID NO:2, SEQ ID NO: 4, at least 9 amino acids of SEQ ID NO: 2, or at least 9 amino acids of SEQ ID NO: 4, and a pharmaceutically acceptable carrier, which amount is effective to stimulate the formation of antibodies against *Leptospira interrogans* in a mammal, e.g., a human. Further provided by the present invention is a composition comprising an amount of an immunologically active protein comprising SEQ ID NO: 2, SEQ ID NO: 4, SEQ ID NO: 46, at least 9 amino acids of SEQ ID NO: 2, at least 9 amino acids of SEQ ID NO: 4, or at least 9 amino acids of SEQ ID NO: 46, which amount is effective to immunize a susceptible mammal against infection caused by *Leptospira*. The invention also provides that a composition as described in this paragraph is effective as a vaccine. The invention additionally provides that a composition as described in this paragraph further comprises an effective amount of an immune stimulating agent.

The present invention provides a method of stimulating the formation of antibodies against *Leptospira*, comprising administering to a mammal a composition comprising an effective amount of an immunologically active protein having SEQ ID NO: 2, SEQ ID NO: 4, SEQ ID NO: 46, at least 9 amino acids of SEQ ID NO: 2, at least 9 amino acids of SEQ ID NO: 4, or at least 9 amino acids of SEQ ID NO: 46. The composition as described in this paragraph may further comprise an effective amount of an immune stimulating agent. The present invention also provides that the composition as described in this paragraph is effective as a vaccine.

Further provided by the present invention is an assay kit for detecting antibodies against *Leptospira* strains which contains at least one immunologically active purified protein derived from *Leptospira interrogans* wherein such protein is characterized in that it elicits an immunological response from a mammal, has been prepared by expression in a bacterium other than *Leptospira interrogans*, is free of other *Leptospira interrogans* proteins; and is a protein having SEQ ID NO: 2, SEQ ID NO: 4, SEQ ID NO: 46, at least 9 amino acids of SEQ ID NO: 2, at least 9 amino acids of SEQ ID NO: 4, or at least 9 amino acids of SEQ ID NO: 46, which protein reacts with the antibodies present in a test fluid, and wherein said kit has at least one indicator component which detects complexes of immunologically active protein and antibody. The indicator component of the assay kit of the present invention is an antibody which is directed against the antibody to be detected and which has a label. The assay kit of the present invention contains a label, which comprises a radioactive isotope, or an enzyme, such as peroxidase, which is able to catalyze a color or light reaction.

The present invention further provides that the immunologically active protein in the assay kit is biotinylated, and the indicator component is avidin or streptavidin having an enzyme covalently bonded thereto. The present invention provides an ELISA assay kit. The present invention provides an assay kit as described hereinabove, wherein the at least one immunologically active protein is coupled to microtiter plates, and the indicator component comprises anti-human immunoglobulin to which an enzyme catalyzing a color reaction is coupled. The present invention also provides an assay kit as described hereinabove, wherein the indicator component comprises IgG antibodies, IgM antibodies or a mixture thereof.

Provided by the present invention is a method for the detection of *Leptospira* infection, comprising the steps of contacting LigA protein from *Leptospira interrogans* with a biological sample from a mammal suspected of having *Leptospira* infection, wherein the LigA protein is characterized in that it is a protein having SEQ ID NO: 2, or at least 9 amino acids of SEQ ID NO: 2, and detecting the presence or absence of a complex formed between LigA and antibodies in the biological sample.

Further provided by the present invention is a method for the detection of *Leptospira* infection, comprising the steps of contacting LigB protein from *Leptospira interrogans* with a biological sample from a mammal suspected of having *Leptospira* infection, wherein the LigB protein is characterized in that it is a protein having SEQ ID NO: 4, SEQ ID NO: 46, at least 9 amino acids of SEQ ID NO: 4, or at least 9 amino acids of SEQ ID NO: 46, and detecting the presence or absence of a complex formed between LigB and antibodies in the biological sample.

Additionally provided by the present invention is an antibody specific for the purified LigA polypeptide and the purified LigB polypeptide, as described hereinabove. The present invention further provides for monoclonal or polyclonal antibodies, and the methods of making monoclonal or polyclonal antibodies.

BRIEF DESCRIPTION OF THE DRAWINGS

FIG. 1. Nucleotide sequence of ligA (SEQ ID NO: 1) and its deduced amino acid sequence (SEQ ID NO: 2). Bold regions are the three possible translation start codons. Underlined nucleotides indicate primer annealing sites for FIGS. 3 and 7, respectively. Arrows show the potential transcription termination sequence.

FIG. 2. Alignment of the predicted amino acid sequences for the twelve tandem repeats (SEQ ID NOs: 5-16) and the immunoglobulin-like domain of *E. coli* intimin binding (receptor) protein (Igl1, CD: pfam02368 (SEQ ID NO: 17); Igl2, CD: smart00635 (SEQ ID NO: 18)). Twelve repeat sequences of a 90 amino acid sequence are from 136-218, 224-310, 311-400, 401-489, 490-580, 581-670, 671-760, 761-851, 852-942, 943-1033, 1034-1125 and 1126-1216, respectively.

FIG. 8. Nucleotide sequences of the ligB (SEQ ID NO:3) and its deduced amino acid sequence (SEQ ID NO:4). Bold represents three possible start codons and Italics indicate the potential ribosome-binding site. The predicted signal sequence of LigB is underlined. Serine rich region and a possible tyrosine kinase phosphorylation are earmarked in dotted lines and double underlined. Waveline indicates the homology region with IBD of Tirintimin complex. The Genbank accession number for the nucleotide sequence of ligB is AF368236.

FIG. 9. Comparison of the structural domains of LigB with LigA from *L. interrogans* serovar pomona invasin from *Yersinia* and intimin from *E. coli*. Dark and dotted boxes represent the Ig-like domain and C type lectin like domain. LysM represents lysing motif in *E. coli*. ORFU shows the open reading frame present in Tir and Intimin of *E. coli*.

FIG. 10. Alignment of twelve repeats of 90 amino acid sequence of LigB (SEQ ID NOs:19-30) and its homology with the bacterial Ig-like domain from Pfam ((Ig1 (SEQ ID NO:31) and Ig2 (SEQ ID NO:32)). Gaps have been introduced to optimize alignment among the polypeptides.

FIG. 11. (A) Alignment of C-terminal variation regions of LigA (SEQ ID NO: 33) and LigB (SEQ ID NO: 34).

FIG. 12. Nucleotide sequence of ligB (SEQ ID NO: 45) and its deduced amino acid sequence (SEQ ID NO: 46).

DETAILED DESCRIPTION OF THE INVENTION

I. *Leptospira*

Figure 3:
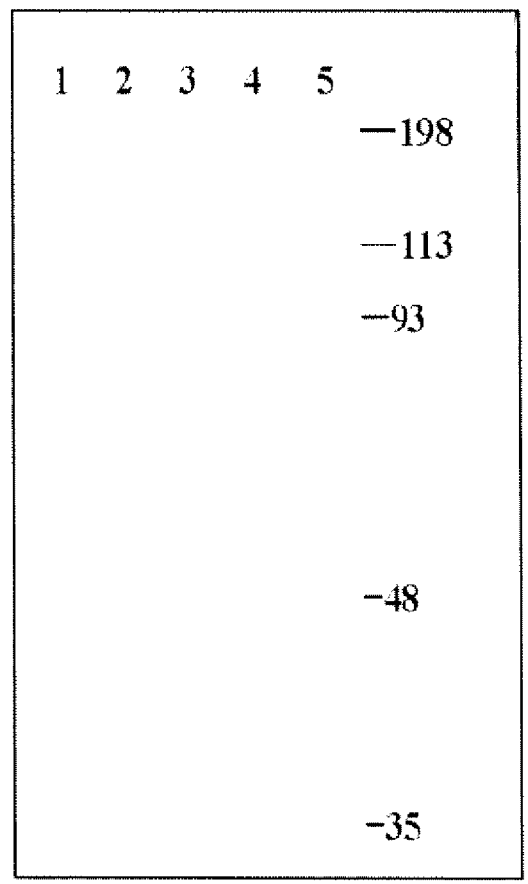
FIG. 3. Expression of LigA in *E. coli*. Whole cell lysates of *E. coli* were subjected to SDS-PAGE, transferred to nitrocellulose and blotted with a 1:100 dilution of rabbit antiserum to the 90 kDa truncated LigA. Lanes 1 & 2. *E. coli* with vector, pET22b only. Lanes 3 & 4. *E. coli* harboring pET22b plus ligA construct. Lanes 2 & 4. *E. coli* was induced with 0.4 mM IPTG. Lane 5. Pre-stained molecular size markers (Bio-Rad, CA).

*Leptospira* organisms are very thin, tightly coiled, obligate aerobic spirochetes characterized by a unique flexuous type of motility. *Leptospira* is a gram-negative spirochete with internal flagella. The genus is divided into two species: the pathogenic leptospires *L. interrogans* and the free-living leptospire *L. biflexa*. Serotypes of *L. interrogans* are the agents of leptospirosis, a zoonotic disease.

*Leptospira* enters the host through mucosa and broken skin, resulting in bacteremia. The spirochetes multiply in organs, most commonly the central nervous system, kidneys, and liver. They are cleared by the immune response from the blood and most tissues but persist and multiply for some time in the kidney tubules. Infective bacteria are shed in the urine. The mechanism of tissue damage is not known.

The primary hosts for this disease are wild and domestic animals, and the disease is a major cause of economic loss in the meat and dairy industry. Humans are accidental hosts in whom this disseminated disease varies in severity from subclinical to fatal. Humans acquire the infection by contact with the urine of infected animals. Human-to-human transmission is very rare. The first human case of leptospirosis was described in 1886 as a severe icteric illness and was referred to as Weil's disease; however, most human cases of leptospirosis are nonicteric and are not life-threatening. Recovery usually follows the appearance of a specific antibody.

Clinical diagnosis is usually confirmed by serology. Isolation of spirochetes is possible, but it is time-consuming and requires special media. Serum antibodies are responsible for host resistance.

Clinical manifestations of leptospirosis are associated with a general febrile disease and are not sufficiently characteristic for diagnosis. As a result, leptospirosis often is initially misdiagnosed as meningitis or hepatitis. Typically, the disease is biphasic, which an acute leptospiremic phase followed by the immune leptospiruric phase. The three organ systems most frequently involved are the central nervous system, kidneys, and liver. After an average incubation period of 7 to 14 days, the leptospiremic acute phase is evidenced by abrupt onset of fever, severe headache, muscle pain, and nausea; these symptoms persist for approximately 7 days. Jaundice occurs during this phase in more severe infections. With the appearance of antileptospiral antibodies, the acute phase of the disease subsides and leptospires can no longer be isolated from the blood. The immune leptospiruric phase occurs after an asymptomatic period of several days. It is manifested by a fever of shorter duration and central nervous system involvement (meningitis). Leptospires appear in the urine during this phase and are shed for various periods depending on the host.

*Leptospira* has the general structural characteristics that distinguish spirochetes from other bacteria. The cell is encased in a three- to five-layer outer membrane or envelope. Beneath this outer membrane are the flexible, helical peptidoglycan layer and the cytoplasmic membrane; these encompass the cytoplasmic contents of the cell. The structures surrounded by the outer membrane are collectively called the protoplasmic cylinder. An unusual feature of the spirochetes is the location of the flagella, which lie between the outer membrane and the peptidoglycan layer. They are referred to as periplasmic flagella. The periplasmic flagella are attached to the protoplasmic cylinder subterminally at each end and extend toward the center of the cell. The number of periplasmic flagella per cell varies among the spirochetes. The motility of bacteria with external flagella is impeded in viscous environments, but that of spirochetes is enhanced. The slender (0.1 µm by 8 to 20 µm) leptospires are tightly coiled, flexible cells. In liquid media, one or both ends are usually hooked. Leptospires are too slender to be visualized with the bright-field microscope, but are clearly seen by dark-field or phase microscopy. They do not stain well with aniline dyes.

The leptospires have two periplasmic flagella, one originating at each end of the cell. The free ends of the periplasmic flagella extend toward the center of the cell, but do not overlap as they do in other spirochetes. The basal bodies of *Leptospira* periplasmic flagella resemble those of Gram-negative bacteria, whereas those of other spirochetes are similar to the basal bodies of Gram-positive bacteria. *Leptospira* differs from other spirochetes in that they are lacking lycolipids and having diaminopimelic acid rather than ornithine in its peptidoglycan.

The leptospires are the most readily cultivated of the pathogenic spirochetes. They have relatively simple nutritional requirements; long-chain fatty acids and vitamins B1 and B12 are the only organic compounds known to be necessary for growth. When cultivated in media of pH 7.4 at 30° C., their average generation time is about 12 hours. Aeration is required for maximal growth. They can be cultivated in plates containing soft (1 percent) agar medium, in which they form primarily subsurface colonies.

The two species, *L. interrogans* and *L. biflexa*, are further divided into serotypes based on their antigenic composition. More than 200 serotypes have been identified in *L. interrogans*. The most prevalent serotypes in the United States are canicola, grippotyphosa, hardjo, icterohaemorrhagiae, and pomona. Genetic studies have demonstrated that serologically diverse serotypes may be present in the same genetic group. At least seven species of pathogenic leptospires have been identified by nucleotide analysis.

The mucosa and broken skin are the most likely sites of entry for the pathogenic leptospires. A generalized infection ensues, but no lesion develops at the site of entry. Bacteremia occurs during the acute, leptospiremic phase of the disease. The host responds by producing antibodies that, in combination with complement, are leptospiricidal. The leptospires are rapidly eliminated from all host tissues except the brain, eyes, and kidneys. Leptospires surviving in the brain and eyes multiply slowly if at all; however, in the kidneys they multiply in the convoluted tubules and are shed in the urine (the leptospiruric phase). The leptospires may persist in the host for weeks to months; in rodents they may be shed in the urine for the lifetime of the animal. Leptospiruric urine is the vehicle of transmission of this disease.

The mechanism by which leptospires cause disease remains unresolved, as neither endotoxins nor exotoxins have been associated with them. The marked contrast between the extent of functional impairment in leptospirosis and the scarcity of histologic lesions suggests that most damage occurs at the subcellular level. Damage to the endothelial lining of the capillaries and subsequent interference with blood flow appear responsible for the lesions associated with leptospirosis. The most notable feature of severe leptospirosis is the progressive impairment of hepatic and renal function. Renal failure is the most common cause of death. The lack of substantial cell destruction in leptospirosis is reflected in the complete recovery of hepatic and renal function in survivors. Although spontaneous abortion is common in infected cattle and swine, only recently has a human case of fatal congenital leptospirosis been documented.

The host's immunologic response to leptospirosis is thought to be responsible for lesions associated with the late phase of this disease; this helps to explain the ineffectiveness of antibiotics once symptoms of the disease have been present for 4 days or more.

Nonspecific host defenses appear ineffective against the virulent leptospires, which are rapidly killed in vitro by the antibody-complement system; virulent strains are more resistant to this leptospiricidal activity than are avirulent strains.

Immunity to leptospirosis is primarily humoral; cell-mediated immunity does not appear to be important, but may be responsible for some of the late manifestations of the disease. Immunity to leptospirosis is serotype specific and may persist for years. Immune serum has been used to treat human leptospirosis and passively protects experimental animals from the disease. The survival of leptospires with in the convoluted tubules of the kidneys may be related to the ineffectiveness of the antibody-complement system at this site. Previously infected animals can become seronegative and continue to shed leptospires in their urine, possibly because of the lack of antigenic stimulation by leptospires in the kidneys.

Because clinical manifestations of leptospirosis are too variable and nonspecific to be diagnostically useful, microscopic demonstration of the organisms, serologic tests, or both are used in diagnosis. The microscopic agglutination test is most frequently used for serodiagnosis. The organisms can be isolated from blood or urine on commercially available media, but the test must be requested specifically because special media is needed. Isolation of the organisms confirms the diagnosis.

Reducing its prevalence in wild and domestic animals can control human leptospirosis. Although little can be done about controlling the disease in wild animals, leptospirosis in domestic animals can be controlled through vaccination with inactivated whole cells or an outer membrane preparation. If vaccines do not contain a sufficient immunogenic mass, the resulting immune response protects the host against clinical disease, but not against development of the renal shedder state. Because a multiplicity of serotypes may exist in a given geographic region and the protection afforded by the inactivated vaccines is serotype specific, the use of polyvalent vaccines is usually recommended.

Although the leptospires are susceptible to antibiotics such as penicillin and tetracycline in vitro, use of these drugs in the treatment of leptospirosis is somewhat controversial. Treatment is most effective if initiated within a week of disease onset. At later times, immunologic damage may already have begun, rendering antimicrobial therapy less effective. Doxycycline has been used successfully as a chemoprophylactic agent for military personnel training in tropical areas.

II. LigA and LigB

The ligA (SEQ ID NO: 1) and ligB (SEQ ID NO:3, SEQ ID NO:45) encode Leptospiral immunoglobin (Ig)-like protein A and B (LigA and LigB) from *Leptospira interrogans* serovar pomona type kennewicki and have molecular masses of approximately 130 and 140 kDa, respectively.

LigA has twelve or more repeats of a 90 amino acid motif homologous with bacterial Ig-like domains such as intimins of *E. coli*, invasin of *Yersinia* and a cell surface protein of *C. acetobutylicum* (Palaniappan, R. U. M. et al., *Infect. Immun.*, 70:5924-5930 (2002)).

The complete nucleotide sequence of a novel ligB is homologous with ligA of *Leptospira*, and cell adhesion proteins such as intimin of *E. coli* and a cell adhesion protein of *C. acetobutylicum.*

III. Definitions

The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

"Expression" refers to the transcription and/or translation of an endogenous gene or a transgene in a host cell. For example, in the case of antisense constructs, expression may refer to the transcription of the antisense DNA only. In addition, expression refers to the transcription and stable accumulation of sense (mRNA) or functional RNA. Expression may also refer to the production of protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" or "exogenous" gene refers to a gene not normally found in the host organism but that is introduced by gene transfer.

The invention encompasses isolated or substantially purified nucleic acid compositions. In the context of the present invention, for example, an "isolated" or "purified" DNA molecule is a DNA molecule that exists apart from its native environment and is therefore not a product of nature. An isolated DNA molecule may exist in a purified form or may exist in a non-native environment such as, for example, a transgenic host cell. For example, an "isolated" or "purified" nucleic acid molecule, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences and proteins or partial-length proteins encoded thereby are also encompassed by the present invention. By "fragment" or "portion" is meant a full length, or less than full length, of the nucleotide sequence encoding, or the amino acid sequence of, a polypeptide or protein.

A "mutation" refers to an insertion, deletion or substitution of one or more nucleotide bases of a nucleic acid sequence, so that the nucleic acid sequence differs from the wild-type sequence. For example, a "point" mutation refers to an alteration in the sequence of a nucleotide at a single base position from the wild type sequence.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucl. Acids Res.,* 19:508 (1991); Ohtsuka et al., *JBC,* 260:2605 (1985); Rossolini et al., *Mol. Cell. Probes,* 8:91 (1994). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence," or "polynucleotide" may also be used interchangeably with gene, cDNA, DNA and RNA encoded by a gene (Batzer et al., 1991; Ohtsuka et al., 1985; Rossolini et al., 1999).

"Operably linked" when used with respect to nucleic acid, means joined as part of the same nucleic acid molecule, suitably positioned and oriented for transcription to be initiated from the promoter. DNA operably linked to a promoter is under transcriptional initiation regulation of the promoter. Coding sequences can be operably-linked to regulatory sequences in sense or antisense orientation.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of, for example, a TATA-box, a −35, −10 polymerase binding site and/or a ribosome binding site (Shine-Dolgarno sequence), and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, a −35, −10 polymerase binding site and/or a ribosome binding site (Shine-Dolgarno sequence), that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box, a −35, −10 polymerase binding site, a ribosome binding site (Shine-Dolgarno sequence), and/or an initiator.

"Constitutive expression" refers to expression using a constitutive or regulated promoter. "Conditional" and "regulated expression" refer to expression controlled by a regulated promoter. An "inducible promoter" is a regulated promoter that can be turned on in a cell by an external stimulus, such as a chemical, light, hormone, stress, or a pathogen.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS,* 4:11 (1988); the local homology algorithm of Smith et al., *Adv. Appl. Math.,* 2:482 (1981); the homology alignment algorithm of Needleman and Wunsch, *JMB,* 48:443 (1970); the search-for-similarity-method of Pearson and Lipman, *Proc. Natl. Acad. Sci. USA,* 85:2444 (1988); the algorithm of Karlin and Altschul, *Proc. Natl. Acad. Sci. USA,* 87:2264 (1990), modified as in Karlin and Altschul, *Proc. Natl. Acad. Sci. USA,* 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988); Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994). The ALIGN program is based on the algorithm of Myers and Miller, supra. The BLAST programs of Altschul et al., *JMB*, 215:403 (1990); *Nucl. Acids Res.*, 25:3389 (1990), are based on the algorithm of Karlin and Altschul supra.

Software for performing BLAST analyses is publicly available through the National Center for Biotechnology Information, which is available on the world wide web at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%. Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, N.Y. (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The terms "protein," "peptide" and "polypeptide" are used interchangeably herein. The term protein, as used herein, generally refers to a long, linear polymer of amino acids joined head to tail by a peptide bond between the carboxylic acid group of one amino acid and the amino group of the next.

As used herein, the term "immunogenic protein" refers to a protein that is capable of inducing a humoral and/or a cell-mediated immune response. A substance that induces a specific immune response may also be referred to as an "antigen," an "immunogen," or an "immunologically active protein."

As used herein, the term "leptospiral protein" includes variants or biologically active or inactive fragments of LigA or LigB from *Leptospira interrogans*. A "variant" of the polypeptide is a leptospiral protein that is not completely identical to a native leptospiral protein. A variant leptospiral protein can be obtained by altering the amino acid sequence by insertion, deletion, or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. Stryer, L. *Biochemistry* (2d edition) W. H. Freeman and Co. San Francisco (1981), p. 14-15; Lehninger, A. *Biochemistry* (2d ed., 1975), p. 73-75.

It is known that variant polypeptides can be obtained based on substituting certain amino acids for other amino acids in the polypeptide structure in order to modify or improve biological activity. For example, through substitution of alternative amino acids, small conformational changes may be conferred upon a polypeptide that result in increased bioactivity. Alternatively, amino acid substitutions in certain polypeptides may be used to provide residues that may then be linked to other molecules to provide peptide-molecule conjugates that retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a protein, as governed by the hydrophilicity of its adjacent amino acids, correlates with its immunogenicity. U.S. Pat. No. 4,554,101. Accordingly, it is noted that substitutions can be made based on the hydrophilicity assigned to each amino acid. In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant leptospiral protein comprises at least seven amino acid residues, preferably about 20 to about 2000 residues, and more preferably about 50 to about 1000 residues, and even more preferably about 80 to about 200 residues, wherein the variant leptospiral protein has at least 50%, preferably at least about 80%, and more preferably at least about 90% but less than 100%, contiguous amino acid sequence homology or identity to the amino acid sequence of a corresponding native leptospiral protein.

The amino acid sequence of the variant leptospiral protein corresponds essentially to the native leptospiral protein amino acid sequence. As used herein "correspond essentially to" refers to a polypeptide sequence that will elicit a protective immunological response substantially the same as the response generated by native leptospiral protein. Such a response may be at least 60% of the level generated by native leptospiral protein, and may even be at least 80% of the level generated by native leptospiral protein. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest.

A variant of the invention may include amino acid residues not present in the corresponding native leptospiral protein, or may include deletions relative to the corresponding native leptospiral protein. A variant may also be a truncated "fragment" as compared to the corresponding native leptospiral protein, i.e., only a portion of a full-length protein. Leptospiral protein variants also include peptides having at least one D-amino acid.

The immunologically active proteins of the present invention are leptospiral proteins, as well as proteins, polypeptides, variants or fragments of LigA or LigB from *Leptospira interrogans*. The immunologically active proteins of the present invention may be of variable length, with the minimum fragment length comprising between 9-15 amino acids.

As used herein, a "transgenic," "transformed," or "recombinant" cell refers to a genetically modified or genetically altered cell, the genome of which comprises a recombinant DNA molecule or sequence ("transgene"). For example, a "transgenic cell" can be a cell transformed with a "vector." A "transgenic," "transformed," or "recombinant" cell thus refers to a host cell such as a bacterial or yeast cell into which a heterologous nucleic acid molecule has been introduced. The nucleic acid molecule can be stably integrated into the genome by methods generally known in the art (e.g., disclosed in Sambrook and Russell, 2001). For example, "transformed," "transformant," and "transgenic" cells have been through the transformation process and contain a foreign or exogenous gene. The term "untransformed" refers to cells that have not been through the transformation process.

The term "transformation" refers to the transfer of a nucleic acid fragment into the genome of a host cell, or the transfer into a host cell of a nucleic acid fragment that is maintained extrachromosomally.

"Vector" is defined to include, inter alia, any plasmid, cosmid, phage or other construct in double or single stranded linear or circular form that may or may not be self transmissible or mobilizable, and that can transform prokaryotic or eukaryotic host either by integration into the cellular genome or exist extrachromosomally, e.g., autonomous replicating plasmid with an origin of replication. A vector can comprise a construct such as an expression cassette having a DNA sequence capable of directing expression of a particular nucleotide sequence in an appropriate host cell, comprising a promoter operably linked to the nucleotide sequence of interest that also is operably linked to termination signals. An expression cassette also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus.

The term "wild type" refers to an untransformed cell, i.e., one where the genome has not been altered by the presence of the recombinant DNA molecule or sequence or by other means of mutagenesis. A "corresponding" untransformed cell is a typical control cell, i.e., one that has been subjected to transformation conditions, but has not been exposed to exogenous DNA.

A "vaccine" is a compound or composition that will elicit a protective immunological response in an animal to which the vaccine has been administered. An immunological response to a vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest.

As used herein, the term "therapeutic agent" refers to any agent or material that has a beneficial effect on the mammalian recipient. Thus, "therapeutic agent" embraces both therapeutic and prophylactic molecules having nucleic acid or protein components.

IV. Vaccine Preparations

The present invention provides a vaccine for use to protect mammals against *Leptospira* colonization or infection. For example, the vaccine may contain an immunogenic amount of isolated and purified *Leptospira* protein or cell in combination with a physiologically-acceptable, non-toxic vehicle. Vaccines of the present invention can also include effective amounts of immunological adjuvants, known to enhance an immune response.

To immunize a subject, the immunogenic protein from *Leptospira* is administered parenterally, usually by intramuscular or subcutaneous injection in an appropriate vehicle. Other modes of administration, however, are also acceptable. For example, the vaccine may be administered orally, or via a mucosal route, such as a nasal, gastrointestinal or genital site. Vaccine formulations will contain an effective amount of the active ingredient in a vehicle. The effective amount is sufficient to prevent, ameliorate or reduce the incidence of *Leptospira* infection in the target mammal. The effective amount is readily determined by one skilled in the art. The active ingredient may typically range from about 1% to about 95% (w/w) of the composition, or even higher or lower if appropriate. The quantity to be administered depends upon factors such as the age, weight and physical condition of the animal considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the leptospiral vaccine in one or more doses. Multiple doses may be administered as is required to maintain a state of immunity to *Leptospira*.

To prepare a vaccine, the immunogenic *Leptospira* protein or proteins can be isolated, lyophilized and stabilized. The vaccine may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. (McGhee et al., 1993). Finally, the immunogenic product may be incorporated into liposomes for use in a vaccine formulation, or may be conjugated to proteins such as keyhole limpet hemocyanin (KLH) or human serum albumin (HSA) or other polymers.

V. Antibodies

The antibodies of the invention are prepared by using standard techniques. To prepare polyclonal antibodies or "antisera," an animal is inoculated with an antigen, i.e., a purified immunogenic protein from *Leptospira*, and then immunoglobulins are recovered from a fluid, such as blood serum, that contains the immunoglobulins, after the animal has had an immune response.

For inoculation, the antigen is preferably bound to a carrier peptide and emulsified using a biologically suitable emulsifying agent, such as Freund's incomplete adjuvant. A variety of mammalian or avian host organisms may be used to prepare polyclonal antibodies against *Leptospira*.

Following immunization, immunoglobulin is purified from the immunized bird or mammal, e.g., goat, rabbit, mouse, rat, or donkey and the like. For certain applications, particularly certain pharmaceutical applications, it is preferable to obtain a composition in which the antibodies are essentially free of antibodies that do not react with the immunogen. This composition is composed virtually entirely of the high titer, monospecific, purified polyclonal antibodies to the *Leptospira* protein.

Antibodies can be purified by affinity chromatography, using purified *Leptospira* protein. Purification of antibodies by affinity chromatography is generally known to those skilled in the art (see, for example, U.S. Pat. No. 4,533,630). Briefly, the purified antibody is bound to a solid support for a sufficient time and under appropriate conditions for the antibody to bind to the polypeptide or peptide. Such time and conditions are readily determinable by those skilled in the art. The unbound, unreacted antibody is then removed, such as by washing. The bound antibody is then recovered from the column by eluting the antibodies, so as to yield purified, monospecific polyclonal antibodies.

Monoclonal antibodies can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the $F_{(ab)}$ fragment scFv antibodies, as are partially humanized monoclonal antibodies.

Thus, it will be understood by those skilled in the art that the hybridomas herein referred to may be subject to genetic mutation or other changes while still retaining the ability to produce monoclonal antibody of the same desired specificity. The present invention encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules or antibody fragments that retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

VI. Formulations of Vaccine Compounds and Methods of Administration

The vaccine compounds may be formulated as pharmaceutical compositions and administered to a mammalian host, such as a human patient, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent, e.g., an adjuvant, with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 10 ug/kg, e.g., from about 0.5 to about 10 ug/kg of body weight per day, such as 3 to about 5 ug per kilogram body weight of the recipient per day, preferably in the range of 6 to 90 ug/kg/day, most preferably in the range of 15 to 60 mg/kg/day.

The compound is conveniently administered in unit dosage form; for example, containing 10 to 50 ug, conveniently 15 to 50 ug, most conveniently, about 50 ug of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

VII. Assay Kits

The present invention also includes a diagnostic kit for detecting or determining the presence of a *Leptospira* infection. The diagnostic kit may also provide for the detection of the presence of LigA or LigB, or a combination thereof, in a physiological sample.

The kit comprises packaging, containing, separately packaged: (a) an amount of at least a first antibody which binds to a leptospiral protein or polypeptide; and (b) instruction means. Preferably, the antibody is labeled or is bound by a detectable label or a second antibody that is labeled.

The immobilized antibodies to LigA or LigB, and labeled antibodies to LigA and LigB, may be conveniently packaged in kit form, wherein two or more of the various immunoreagents will be separately packaged in preselected amounts, within the outer packaging of the kit, which may be a box, envelope, or the like. The packaging also preferably comprises instruction means, such as a printed insert, a label, a tag, a cassette tape and the like, instructing the user in the practice of the assay format.

For example, one such diagnostic kit for detecting or determining the presence of LigA or LigB comprises packaging containing, separately packaged: (a) a solid surface, such as a fibrous test strip, a multi-well microliter plate, a test tube, or beads, having bound thereto antibodies to LigA or LigB; and (b) a known amount of antibodies specific to LigA or LigB, wherein said antibodies comprise a detectable label, or a binding site for a detectable label.

The kit may comprise a mixture of antibodies, each of which binds to a different epitope on the same leptospiral protein or polypeptide, e.g., a mixture of antibodies comprising antibodies that bind to SEQ ID NO:2 and antibodies that bind to SEQ ID NO:4, and/or SEQ ID NO:46.

The kit may also comprise a blocking agent, e.g., BSA, which may be contacted with a sample to be tested before contacting the sample with the antibody, or may be contacted concurrently with the antibody. In one embodiment of the invention, the kit further comprises a known amount of a second antibody, which is detectably labeled or binds to a detectable label. The second antibody may bind to the same polypeptide as the first antibody, or may bind to the first antibody. Preferably, the kit is a diagnostic kit.

Also provided is a kit useful to detect a leptospiral protein or polypeptide in a sample. The kit comprises a solid substrate on which the sample to be tested is placed and a preparation of antibodies. Preferably, the antibodies are labeled or bind to a detectable label.

The invention will now be described by the following non-limiting examples.

EXAMPLES

Example I

Identification of LigA

Characterization of bacterial antigens expressed only during infection is essential in gaining a deeper understanding of infectious diseases such as leptospirosis. Immunoscreening of gene libraries with convalescent serum is a powerful tool in the discovery of these in vivo expressed immunogens, which would otherwise be difficult or impossible to identify. It has been previously shown that sera from horses that aborted as a result of naturally acquired *L. interrogans* serovar pomona type kennewicki infection recognize numerous periplasmic and outer membrane proteins, some of which are regulated by temperature (Nally, J. E. et al., *Infect. Immun.*, 69:400-404 (2001)). In this study, immunoscreening of a genomic library of *L. interrogans* serovar pomona type kennewicki was performed, and a novel, highly immunogenic protein expressed during equine infection (LigA) was identified.

Materials and Methods

Bacterial strains and culture conditions. *L. interrogans* serovar pomona type kennewicki was provided by Dr. M. Donahue (Diagnostic Laboratory, Department of Veterinary Science, University of Kentucky) who isolated this strain from a case of ERU. Other serovars were obtained from the American Type Culture Collection (ATCC) and maintained in the Diagnostic Laboratory at Cornell University. Leptospires were grown on PLM-5 medium (Intergen, NJ) at 30° C. Growth was monitored by dark field microscopy. Temperature regulation was carried out as previously described (Nally, J. E. et al., *Infect. Immun.*, 69:400-404 (2001)).

Sera. Sera were obtained from mares that had recently aborted due to *Leptospira* infection. These sera had high titers for *L. interrogans* serovar pomona, as determined by the microscopic agglutination test. In most cases, the diagnosis was confirmed by microscopic detection of leptospires in fetal tissues and the placenta. Rabbit anti-leptospiral antibody was obtained from NVSL, Iowa (1098-LEP-FAC). Antisera to LipL32 and LipL36 were kindly provided by D. A. Haake (UCLA, CA).

Genomic DNA library. Genomic DNA was prepared from *L. interrogans* serovar pomona kennewicki as previously described (Chang, Y. F. et al., *DNA Cell. Biol.*, 12:351-362 (1993)). Partial restriction digestion was performed with TSP5091 and the digested fragments were ligated into pre-digested lambda Zap II (Stratagene). Ligated DNA was packaged into Giga pack II Gold packaging extracts and stored in 0.3% chloroform. After transfection into *E. coli* MRF' XL1 blue (Stratagene, CA), the library was plated, amplified, and screened with convalescent mare's serum according to the manufacturer's instructions (Stratagene, CA).

DNA sequencing and analysis. DNA sequencing was done using an ABI model 377 automated nucleic acid sequencer at the Bioresource Center, Cornell University, NY. Homology searches were performed with NCBI, Blast (Altschul, S. F. et al., *Nucleic Acid Res.*, 25:3389-3402 (1997)). Secondary structure, hydrophobicity and antigenic index predictions were obtained by using PCgene and DNA star.

Expression of ligA in *E. coli*.

ligA without the signal sequence (deletion of the N-terminal 31 amino acids) was amplified using primers (sense, 5'-GGGTTTCATATGGCTGGCAAAAGAGGC-3' (SEQ ID NO:35) and antisense, 5'-CCCTCGAGTGGCTCCGTT-TTAAT-3' (SEQ ID NO:36)) and subcloned into NdeI-XhoI sites of pET22b (Novagen, Madison, Wis.). The recombinant plasmid was transformed to *E. coli* BL21 (DE3) and expression was induced by IPTG as previously described (Chang, Y.-F. et al., *Vet. Parasitol.*, 78:137-145 (1998)).

A 90 kDa truncated LigA was subcloned into the XhoI-BamHI sites of pET15b (Novagen) by PCR using primers (sense, 5'-TCGAGGTCTCTCCAGTTTTACC-3' (SEQ ID NO:37) and antisense, 5'-GCGGATCCTGTTTTCATG-TTATGGCTCC-3') (SEQ ID NO:38). The resulting plasmid was transformed into *E. coli* BL21 (DE3) and the truncated recombinant LigA fusion protein was isolated from a lysate of BL21 by affinity chromatography on His Bind Resin (Novagen).

Preparation of LigA specific rabbit antiserum. Antiserum to a 90 kDa truncated LigA was prepared in adult New Zealand rabbits. Recombinant truncate was purified from periplasmic proteins of *E. coli* Nova blue that contained pKS (Stratagene) encoding a 5 kb BamH1-Sal1 fragment or by affinity chromatography on Avidgel F (UniSyn Technology Inc., Tustin, Calif.) to which IgG from convalescent mare's serum had been coupled. The rabbits were immunized subcutaneously with 50 μg of the 90 kDa truncated LigA mixed with complete Freund's adjuvant on day 1 followed by a booster inoculum of 50 μg protein and incomplete Freund's adjuvant on days 10 and 19. On day 35, the rabbits were boosted intravenously with 50 μg of protein and then bled on day 45.

SDS PAGE and Immunoblot Analysis. Purified truncated LigA protein was subjected to SDS-PAGE and immunoblot analysis as previously described (Chang, Y. F. et al., *Infect. Immun.*, 63:3543-3549 (1995); Chang, Y. F. et al., *DNA Cell. Biol.*, 12:351-362 (1993)). Rabbit antiserum to truncated LigA or convalescent mare's sera were used as primary antibodies. Blots were developed with peroxidase conjugated protein G or goat anti-horse IgG conjugated to alkaline phosphatase (KPL). Reactive bands were visualized by using 4-1 chloro-naphthol (0.5 mg/ml) or nitroblue tetrazolium and 5 bromo-3-chloro indolyl phosphate as appropriate.

Immunohistochemistry. Immunohistochemistry was performed on normal and leptospiral infected hamster kidneys using biotin-streptavidin-horseradish peroxidase according to the manufacturer's instructions (Zymed Laboratories, South San Francisco, Calif.). The chromogen was Nova Red (DAKO, Carpinteria, Calif.). The primary antibody was rabbit antiserum specific for truncated LigA and was titrated by using a two-fold serial dilution from 1:10 to 1:320. Negative controls consisted of non-immune rabbit serum diluted 1:10, 1:20 and 1:40. Anti-LipL32 was used as a positive control.

Kidneys were removed from leptospiral infected and normal hamsters euthanized as part of an unrelated research project. These tissues were immediately embedded in O.C.T. Compound (Miles, Elkhart, Ind.) and snap frozen in 2-methyl butane (Sigma, St. Louis, Mo.) prechilled to the point of freezing in liquid nitrogen.

Tissues were sectioned at 6 μm, mounted on Microscope Plus slides (Fisher Scientific), fixed in acetone for 2 minutes and air-dried. Endogenous peroxidase was quenched for 10 minutes in 0.3% hydrogen peroxide in 0.1% w/v sodium azide and rinsed for 3 minutes in 0.01M phosphate buffered saline, pH 7.6 (PBS). Sections were then blocked with 10% heat inactivated goat serum for 10 minutes. The blocking serum was tipped off and the primary antibody applied for 60 minutes at room temperature. After rinsing 3 times in PBS, a 1:400 dilution of biotinylated goat anti-rabbit IgG was added for 20 minutes. Sections were rinsed 3 times and then incubated with a 1:400 dilution of the streptavidin-peroxidase reagent for 10 minutes. After rinsing, the chromogen-substrate mixture was added to the sections and the reaction monitored under the microscope until well developed or until background developed. The slides were again rinsed in PBS, counter-stained lightly with Gill's #1 hematoxylin (about 30 seconds), and then rinsed in tap water. Following dehydration in 2 changes of graded ethanol to 100% for 2 minutes each, the sections were cleared in 4 changes of 100% xylene for 2 minutes each and mounted with Fisher permount.

PCR amplification of ligA in pathogenic serovars. Using a primer pair specific for ligA, PCR was performed on pathogenic serovars including *L. interrogans* serovar pomona, type kennewicki, *L. kirschneri* serovar grippotyphosa, *L. interrogans* serovar hardjo, type hardjobovis, *L. interrogans* serovar icterohaemorrhagiae and *L. interrogans* serovar canicola. The forward primer was "5'-GGAATTCATGTTAAAGTCACT-GCT-3'" (SEQ ID NO:39) and the reverse was "5'-CCGCTC-GAGGTTTTAATAGAGGC-3'" (SEQ ID NO:40). Amplification conditions were as previously described (Chang, Y.-F. et al., *Vet. Pathol.*, 37:68-76 (2000)). PCR products were purified using a gel-purification kit (Qiagen) and digested with BamH1 and HindIII to detect restriction polymorphisms.

Enzyme-linked immunosorbent assay (ELISA). Wells of 96 well polystyrene plates (Falcon 3912 Microtest III, Becton Dickinson, Oxnard, Calif.) were coated overnight at 4° C. with 0.15 µg truncated recombinant LigA in 100 µl PBS, washed, blocked with 2% skim milk in PBS (pH 7.2) with 0.05% Tween 20 and then incubated with a 1:100 dilution of horse serum in triplicate wells for 2 hours at 37° C. After washing, peroxidase conjugated protein G (1:8000) was added (100 µl) to each well and incubated for 2 hours at 37° C. Finally, the plates were washed and developed with fresh substrate consisting of 0.07% orthophenylenediamine and 0.05% hydrogen-peroxide in citric acid-phosphate buffer (pH 5.0). After stopping the reaction with 50 µl 3M sulfuric acid, absorbance was read at 490 nm in an automated plate reader (Biotex, Winooski, Vt.).

Statistical Analysis.

Analysis of variance was used to determine whether there was a significant difference in the mean OD reading for each of the sera used in this study. Multiple comparisons using the least significant difference method were performed to identify which OD mean was significantly different from the other. The analysis was performed using the Statistix software (Analytical Software, Tallahassee, Fla.).

Nucleotide sequence accession numbers. The GenBank accession number for the nucleotide sequences of ligA is AF368236.

Results

Figure 1A:
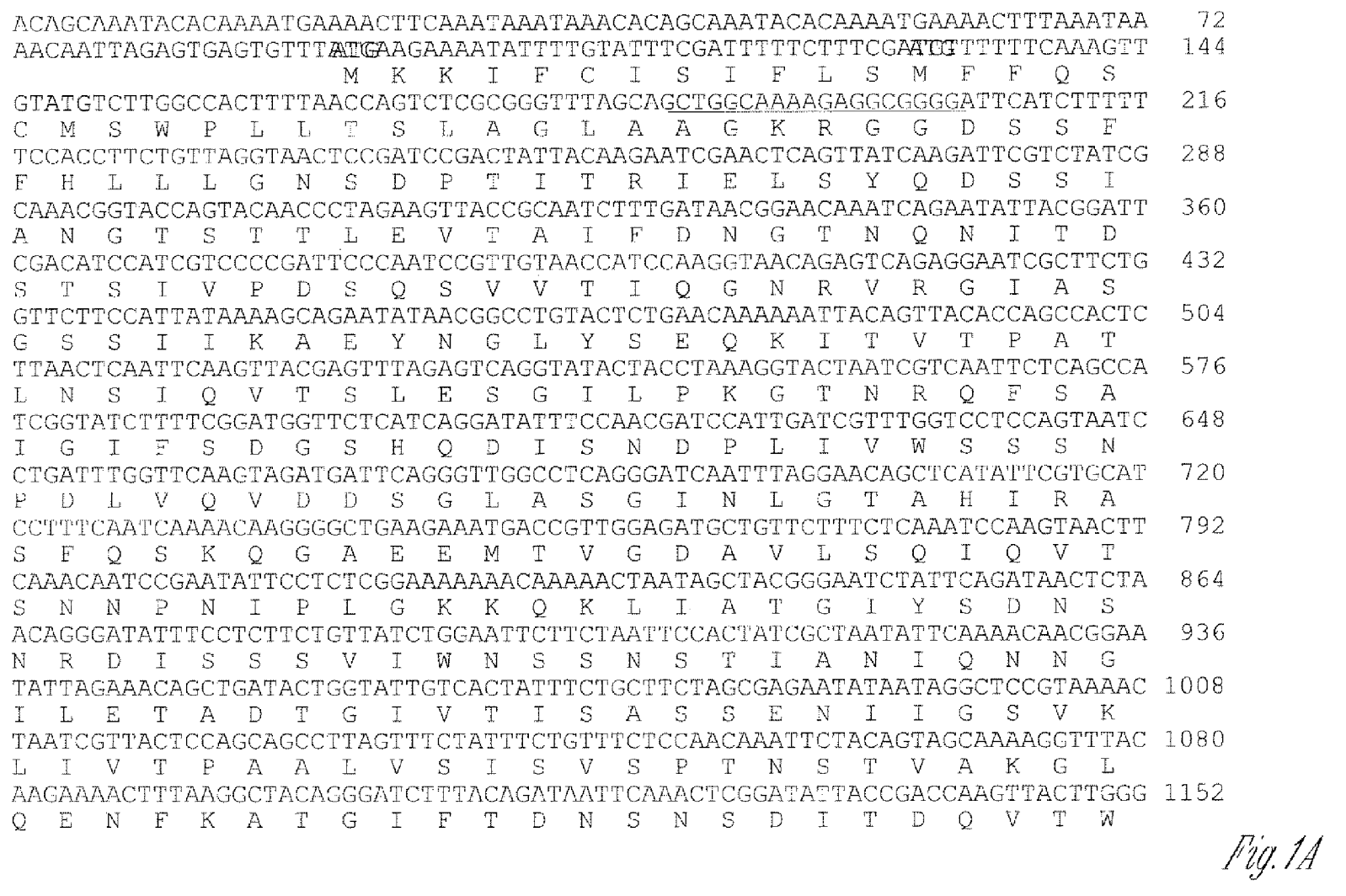
Figure 1B:
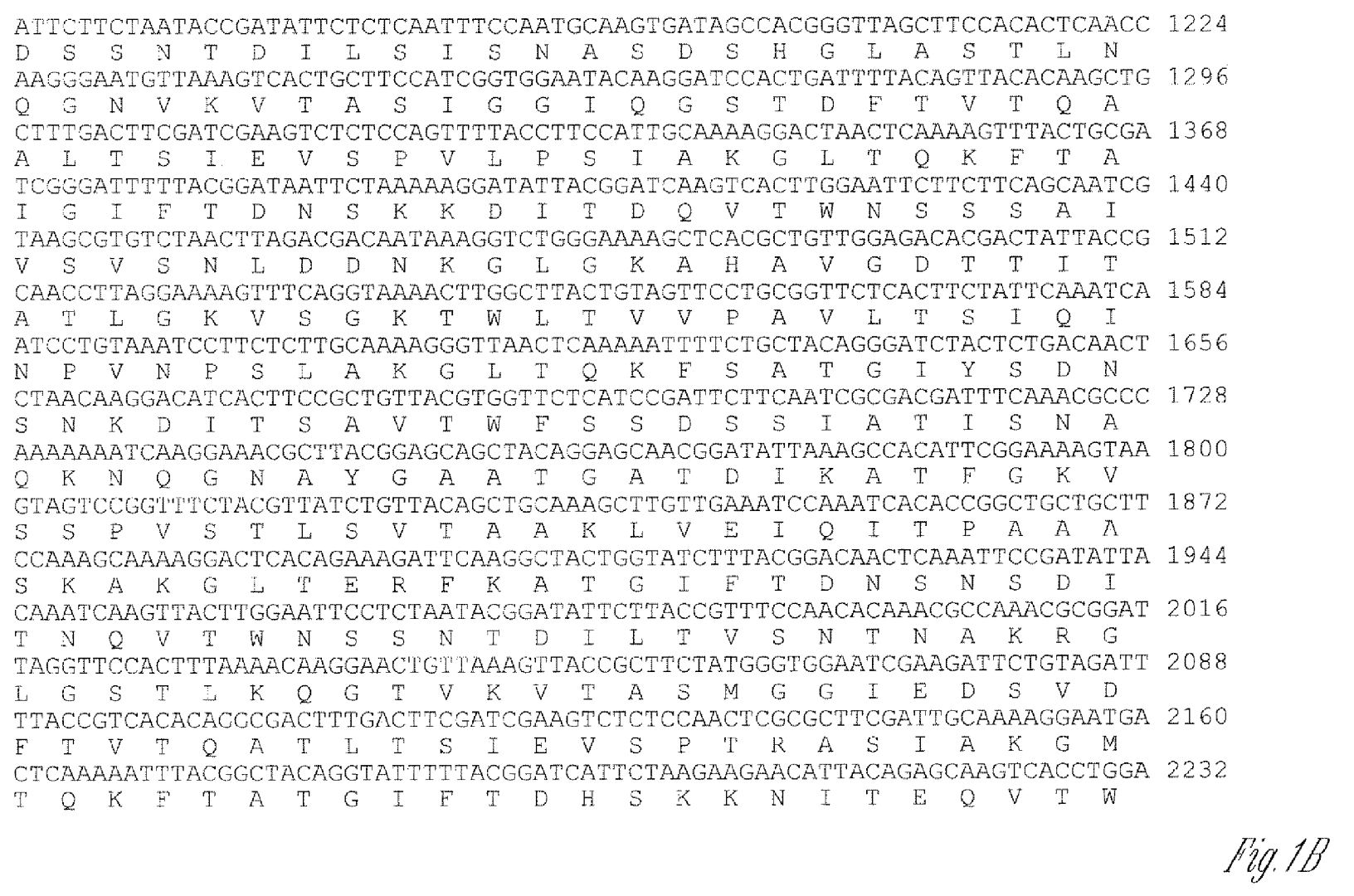
Figure 1C:
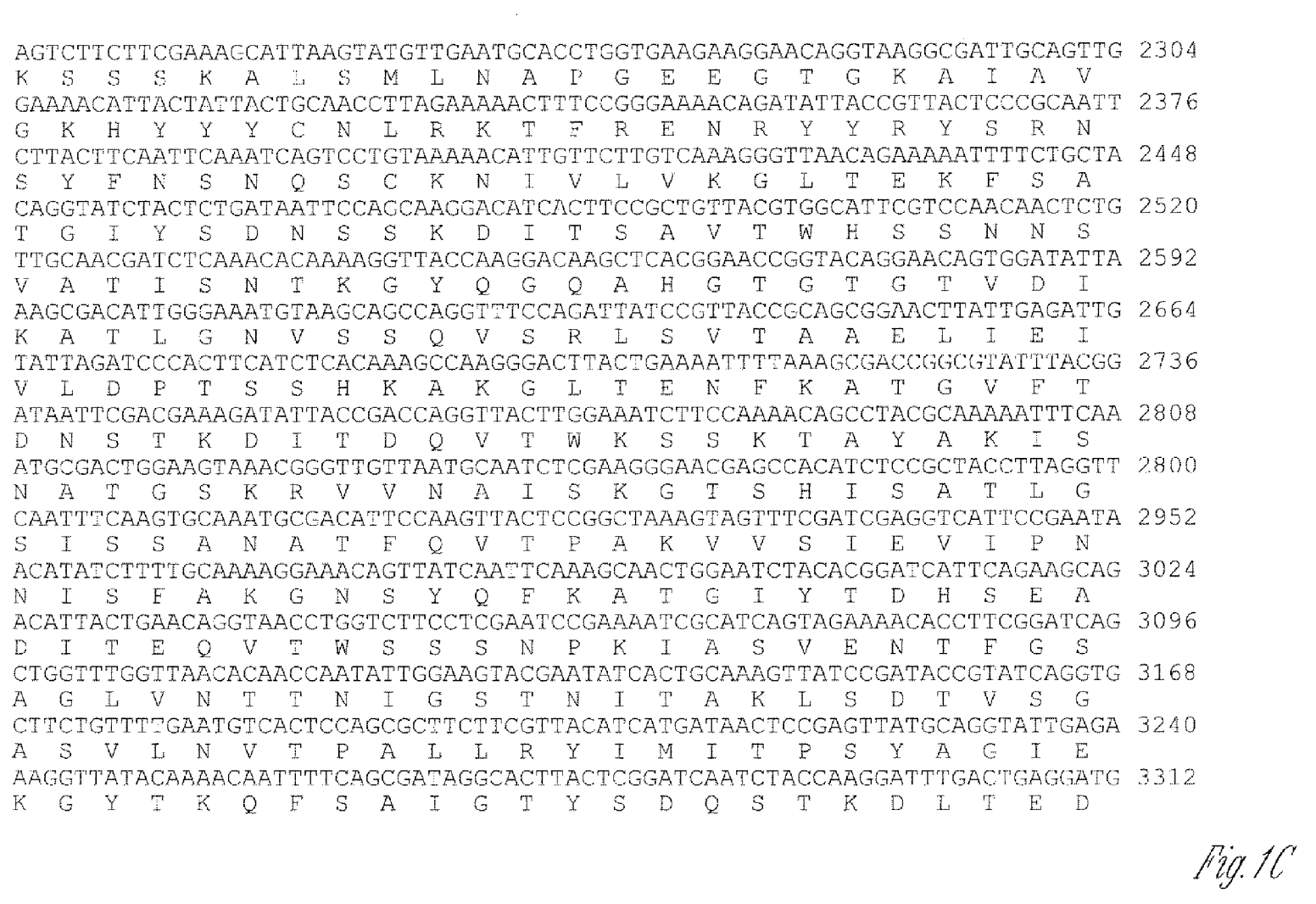

Identification, sequencing and expression of LigA. Screening of the *L. interrogans* genomic library with convalescent mare's serum yielded numerous positive clones, one of which contained an insert of 3,993 bp and expressed a protein that was encoded by an open reading frame of 3,675 bp (FIG. 1). The deduced sequence consisted of 1,225 amino acids with an estimated molecular mass of 129,041 daltons and a pI of 6.35. An N-terminal signal sequence of 31 amino acids was predicted using the Signal P program (Nielsen, H. et al., *Protein Eng.*, 10:1-6 (1997)). Twelve or more tandem repeats of 90 amino acids were detected in LigA (FIG. 2). Analysis of the sequence using NCBI and BLAST revealed homology with the immunoglobulin-like domain of *E. coli* intimin (Genbank accession number AF252560), the putative invasin of *Yersinia pestis* (AJ41459) and the cell adhesion domain of *Clostridium acetobutylicum* (AE007823) (data not shown). LigA tandem repeats that showed homology with bacterial Ig-like domains (Igl1, CD: pfam02368; Igl2, CD: smart00635) are represented in FIG. 2.

Figure 4:
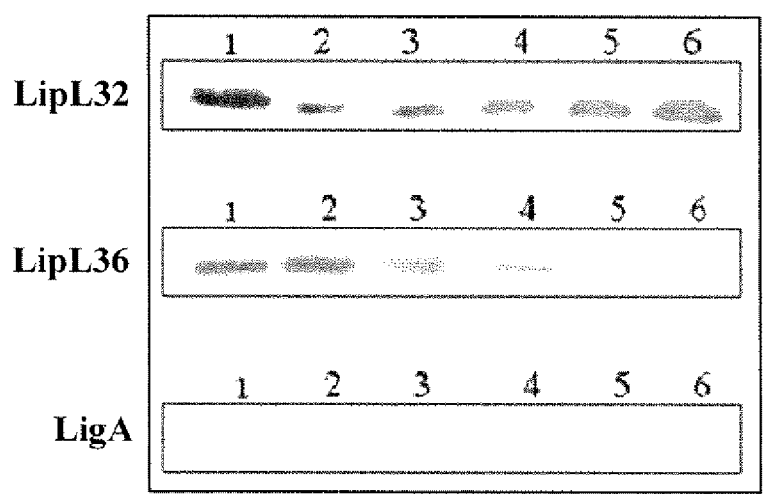
FIG. 4. LipL32 and LipL36 but not LigA expression are temperature regulated. Lane 1. Whole cell lysate of leptospires grown at 30° C. Lanes 2, 3, 4, 5 and 6 represent 2, 3, 4, 5 and 6 day old cultures, respectively, of leptospires grown at 37° C. Each lane was loaded with ~5.0 µg of proteins.

Expression of LigA in *E. coli* but not in *Leptospira* lysates. *E. coli* containing intact ligA without its signal sequence expressed LigA only after IPTG induction (FIG. 3), but LigA expression was toxic to *E. coli* resulting in a 50 fold decrease in viability of cells (data not shown), which is similar to OmpL1 of *Leptospira* (Haake, D. A. et al., *Infect. Immun.*, 67:6572-6582 (1999)). However, the expression of a 90 kDa truncated LigA was not toxic to *E. coli* cells (data not shown). Immunoblotting of whole cell lysates of *L. interrogans* serovar pomona type kennewicki grown at 30 and 37° C. with LigA specific polyclonal rabbit serum did not show any detectable level of LigA (FIG. 4). In contrast, LipL32 was expressed by cultures grown at both 30 and 37° C. whereas LipL36 was down regulated at 37° C.

Figure 5C:
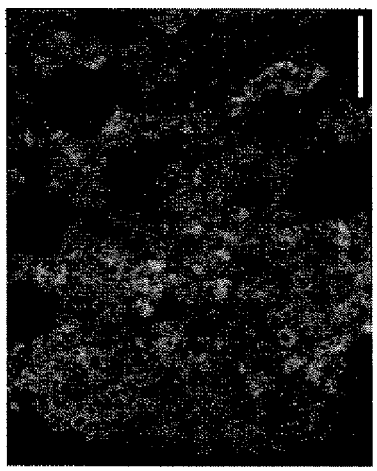
FIG. 5. LigA expression in hamsters infected with *L. interrogans* serovar pomona. Sections of kidney were treated with rabbit antiserum specific for a 90 kDa truncated LigA (A) *L. interrogans* serovar pomona (B), LipL32 (C), LipL36 (D) and with pre-immune serum (E). Kidney sections from non-infected hamsters were unreactive. Bar=67 µm.
Figure 5B:
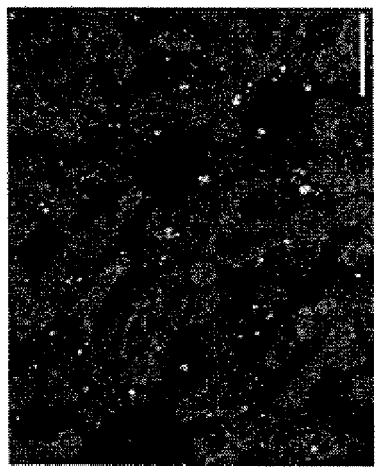
Figure 5E:
Figure 5A:
Figure 5D:
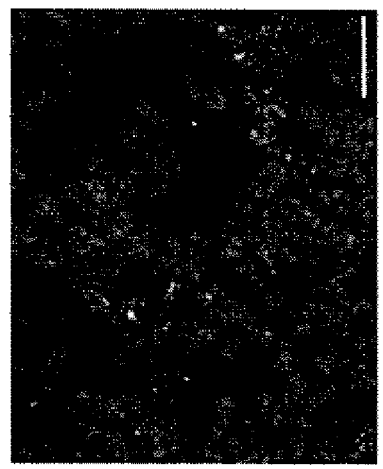

LigA expression in vivo in *Leptospira*-infected hamsters. In order to examine LigA expression during leptospiral infection, immunohistochemistry was performed on kidneys from normal and leptospiral-infected hamsters. LigA was expressed only in leptospiral-infected hamster kidney (FIG. 5A). High titer rabbit anti-leptospiral serum as well as antiserum to LipL32 reacted with leptospires in experimentally infected kidney (FIGS. 5B and 5C). LipL36, which is not expressed by *L. krischneri* serovar grippotyphosa in infected hamster kidney (Barnett, J. K. et al., *Infect. Immun.*, 67:853-861 (1999)), was detected around the proximal convoluted tubules in *L. interrogans* serovar pomona infected hamster kidney at a 1:50 dilution of antiserum to LipL36 (FIG. 5D). Pre-immune rabbit serum did not react (FIG. 5E) and no immune serum reacted with normal hamster kidney (data not shown).

Figure 6:
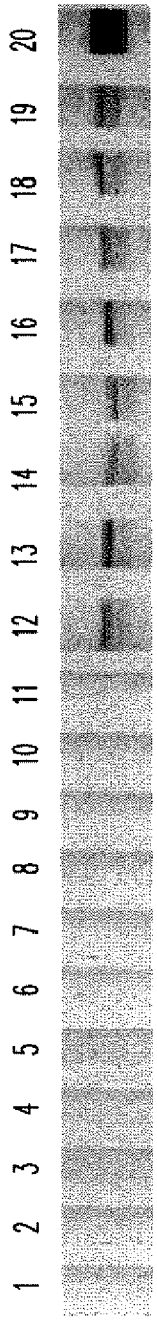
FIG. 6. Recombinant LigA protein purified using metal affinity chromatography and subjected to SDS-PAGE separation was probed with normal horse sera (first 4 lanes), equine lyme disease positive sera (lanes 5-9), human granulocytic ehrlichiosis positive sera (lanes 10-11), aborted mare sera (lanes 12-19), and rabbit serum specific for a 90 kDa truncated LigA (lane 20). Each lane was loaded with ~0.5 µg of protein.

LigA specific antibody in sera of convalescent mares and aborted fetuses. All convalescent sera showed strong reactivity with recombinant LigA by western blot analysis. Negative control horse sera derived from *Borrelia burgdorferi* (Chang, Y.-F. et al., *Vet. Pathol.*, 37:68-76 (2000)), Human Granulocytic Ehrlichiosis agent (HGE) infection (Chang, Y.-F. et al., *Vet. Parasitol.*, 78:137-145 (1998)) and naïve horse sera were unreactive (FIG. 6). The utilization of LigA in ELISA also showed strong reactivity to the convalescent sera (Table 1 below). The mean OD for the leptospiral positive sera (M1-M8) was significantly different from the negative control (L1-L-5) and from sera obtained from HGE (E1-E2) and *B. burgdorferi* (N1-N4) infected animals (P<0.05).

TABLE 1

Table 1. Reactivity in ELISA of rabbit antiserum to recombinant LigA, sera from horses infected with *B. burgdorferi* (L1-5) or *E. equi* (E1 and 2), normal horse sera (N1-4) and aborted mare's sera (M1-8) in ELISA with a 90 kDa truncated LigA (200 ng/well). The ELISA OD values of sera from aborted mares were significantly higher (P < 0.05) than the values for sera from normal, *B. burgdorferi* and *E. equi* infected horses.

| Serum | ELISA OD at serum dilution | | |
|---|---|---|---|
| | 1/200 | 1/400 | 1/800 |
| Rabbit antiserum to a 90 kDa truncated LigA | 1.13 | 1.02 | .58 |
| L1 | .05 | .03 | .01 |
| L2 | .1 | .04 | .02 |
| L3 | .03 | .02 | .02 |
| L4 | .05 | .02 | .03 |
| L5 | .02 | .01 | .01 |
| E1 | .05 | .03 | .05 |
| E2 | .08 | .05 | .04 |
| N1 | .01 | .01 | 0.0 |
| N2 | .01 | .0 | .0 |
| N3 | .02 | .01 | .01 |
| N4 | .03 | .03 | .01 |
| M1 | .39 | .34 | .19 |
| M2 | .38 | .35 | .18 |
| M3 | .45 | .31 | .2 |
| M4 | .6 | .56 | .27 |
| M5 | .28 | .2 | .13 |
| M6 | .47 | .56 | .4 |
| M7 | .73 | .55 | .4 |
| M8 | .56 | .5 | .42 |

Figure 7A:
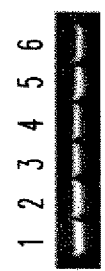
FIG. 7. Agarose gel showing PCR products and restriction analysis of ligA from different pathogenic serovars of *Leptospira* (A) PCR products of ligA (B) HindIII digested PCR product of ligA. Lane 1. *L. interrogans* serovar pomona type kennewicki, 2. *L. interrogans* serovar pomona, 3. *L. interrogans* serovar hardjo, 4. *L. interrogans* serovar icterohemorrhagiae, 5. *L. kirchneri* serovar grippotyphosa, 6. *L. interrogans* serovar wolfii.
Figure 7B:
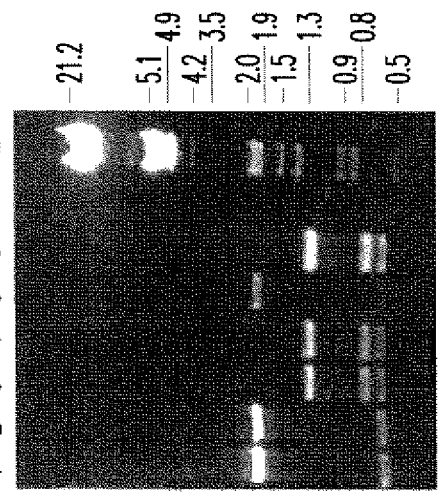

Detection of ligA in other serovars by PCR. PCR amplification revealed the presence of ligA in genomic DNA of the pathogenic serovars hardjo, grippotyphosa, icterohaemorrhagiae and canicola (FIG. 7A). Restriction analysis with BamHI revealed no differences in fragment patterns. However, HindIII digests revealed that ligA was more highly conserved in *L. interrogans* serovar pomona and *L. kirchneri* serovar grippotyphosa than in other serovars (FIG. 7B).

Discussion

LigA is mostly hydrophilic with some hydrophobic regions located at residues 4-24, 306-326, 402-422, 490-510 and 1034-1054 (FIG. 1) and consists of beta sheets with a few alpha helical regions. An Ala-Lys-Glu-Leu-Thr (SEQ ID NO:41) peptide repeat occurs at positions 416, 505, 594 and 867 corresponding to alpha helices. LigA contains 12 or more tandem repeats of a 90 amino acid sequence (FIG. 2). Analysis of the nucleotide sequences using NCBI and BLAST revealed no homology other than that between the repeat region of LigA and the immunoglobulin-like domain of intimin binding protein (int) of *E. coli* (Hamburger, Z. A. et al., *Science*, 286:291-295 (1999); Kelly, G. et al., *Nat. Struct. Biol.*, 6:313-318 (1999); Luo, Y. et al., *Nature*, 405:1073-1077 (2000)), the invasin of *Yersinia pestis* (Isberg, R. R. et al., *Cell*, 50:769-778 (1999); Jerse, A. E. and J. B. Kaper, *Infect. Immun.*, 59:4302-4309 (1991)) and a cell binding domain of *Clostridium acetobutylicum* (Nolling, J. et al., *J. Bacteriol.*, 183:4823-4838 (2001)).

Although sera from recently aborted mares reacted strongly with the 90 kDa truncated LigA, the protein was not detectable by immunoblot in *Leptospira* lysates cultured at 30° and 37° C. In contrast, LipL32 is expressed at both 30° and 37° C. while LipL36 expression is growth-phase dependant (Haake, D. A. et al., *Infect. Immun.*, 68:2276-2285 (2000); Nally, J. E. et al., *Infect. Immun.*, 69:400-404 (2001)). This indicates that LigA is not expressed or thermo-regulated under in vitro culture conditions.

However, immunohistochemistry using rabbit antiserum specific for a 90 kDa truncated LigA revealed expression of LigA in kidneys of infected but not uninfected hamsters. A commercially available high titer anti-leptospiral antiserum showed strong reactivity to the leptospiral organisms in infected hamster kidney. Expression of LipL32 was detected both in vitro (culture) and in vivo (leptospiral-infected hamster kidney) whereas LipL36 expression has been reported only in vitro (Barnett, J. K. et al., *Infect. Immun.*, 67:853-861 (1999)). The in vivo expression of LipL32 has also been confirmed. However, the reactivity of LipL36 rabbit polyclonal antibody with infected hamster kidney at a 1:50 dilution was noted. In contrast, Barnett et al. failed to detect expression of LipL36 in *L. kirschneri* serovar grippotyphosa infected hamster kidney. These positive controls confirm that LigA is expressed only in vivo.

A 90 kDa protein of *Leptospira* has been previously shown to cross-react with polyclonal antiserum to an equine corneal protein (Lucchesi, P. M. and A. E. Parma, *Vet. Immunol. Immunopathol.*, 71:173-179 (1999)). Immunohistochemistry, immunoprecipitation and Western blot analysis revealed no reactivity of LigA specific antiserum with equine cornea, iris, vitreous or lens (data not shown). Thus, LigA does not appear to share antigenic epitopes with equine ocular components and so it is clearly not the reactive protein (Lucchesi, P. M. and A. E. Parma, *Vet. Immunol. Immunopathol.*, 71:173-179 (1999)).

PCR amplification of ligA from genomic DNA of pathogenic serovars such as hardjo, icterohaemorrhagiae, grippotyphosa, and canicola has shown that a similar sequence is widely distributed among the serovars of *L. interrogans*. However, restriction analysis with HindIII showed that the ligA sequence had greater similarity to that of serovars pomona and grippotyphosa than to serovars canicola and icterohaemorrhagiae. Interestingly, *L. interrogans* serovar pomona and *L. kirchneri* serovar grippotyphosa are the serovars most frequently responsible for disease in the horse.

The expression of outer membrane proteins of *Leptospira* such as LipL32, LipL41, OmpL1 and LipL36 has been demonstrated in cultured organisms (Haake, D. A. et al., *J. Bacteriol.*, 175:4225-4234 (1993); Haake, D. A. et al., *Infect. Immun.*, 68:2276-2285 (2000); Haake, D. A. et al., *Infect. Immun.*, 66:1579-1587 (1998); Haake, D. A. et al., *Infect. Immun.*, 67:6572-6582 (1999)). Except for LipL36, these outer membrane proteins are expressed in infected hamsters. Interestingly, this is the first leptospiral protein that is not detectable in vitro (30 or 37° C.) but is expressed in kidneys of infected hamsters.

Example II

Figure 8D:
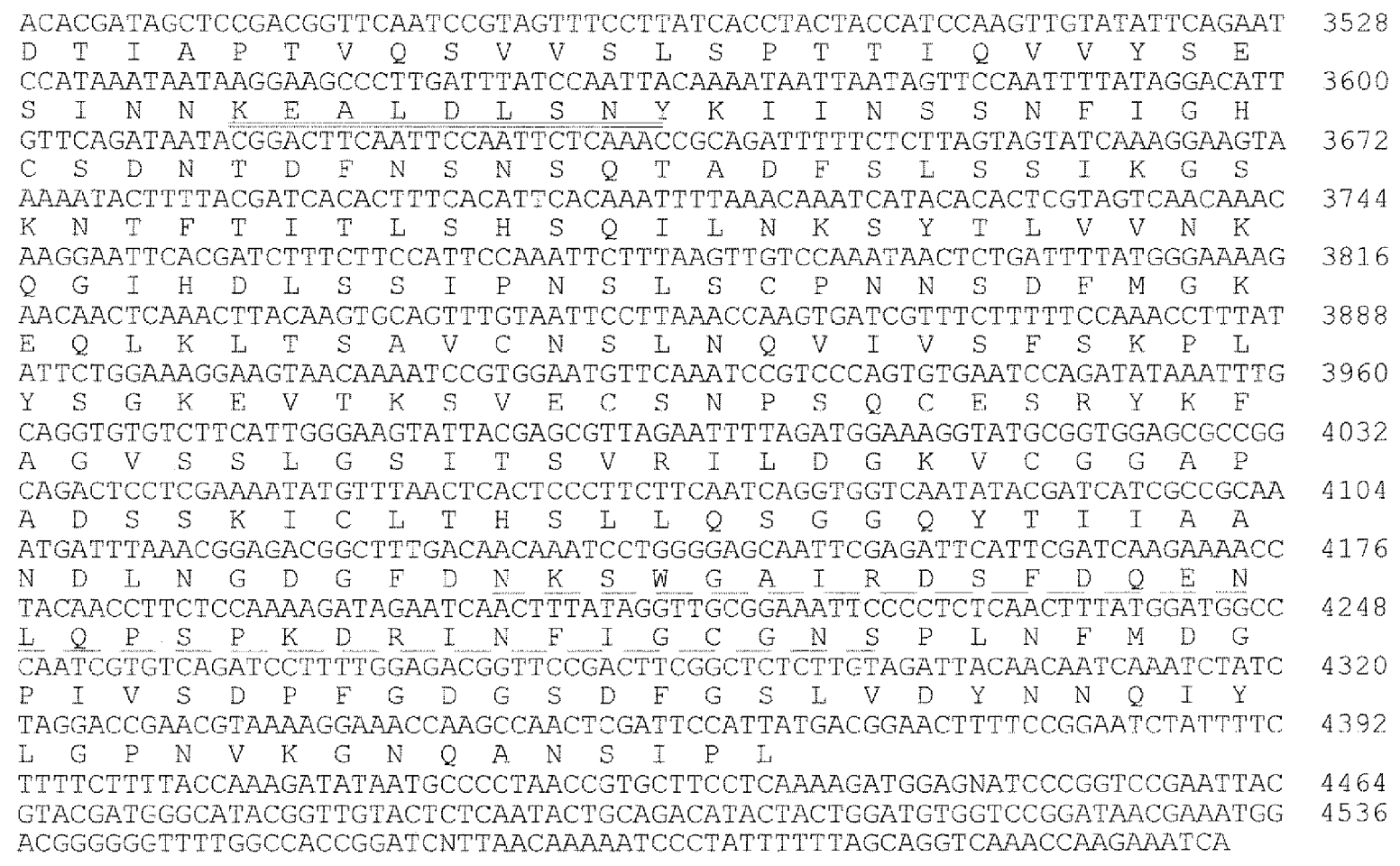

Identification of LigB ligB was obtained using the same procedures as were used to obtain ligA. To summarize, a genomic library of *L. interrogans* serovar Pomona type Kennewicki was constructed as previously described and was screened with convalescent sera from leptospiral infected horses and mares that aborted due to leptospirosis (Palaniappan, R. U. M. et al., *Infect. Immun.*, accepted (2002)). Several positive clones were identified and one of the recombinant clones contained an open reading frame (ORF) of 4200 bp (FIG. 8). The deduced sequence contained 1,420 amino acids with an estimated molecular weight of 140 kDa (SEQ ID NO:4). An N-terminal signal sequence of 31 aa was predicted using the Signal P program (Nielsen, H. et al., *Protein Eng.*, 10:1-6 (1997)). Three possible start codons for this protein were identified and upstream of the start codon of ligB is a potential ribosome-binding site (FIG. 8). NCBI Blast search revealed homology with the conserved bacterial immunoglobulin-like domain (Pfam Big 2) of intimins from *E. coli* (AF319597, AF301015, AF116899) and cell adhesion domain from *C. acetobutylicum* (NC_003030). Nucleotide sequence accession numbers. The GenBank accession number for the nucleotide sequences of ligB is AF534640.

Example III

Comparison of LigA and LigB

LigB has complete homology with LigA in the N-terminal sequences (up to 630 amino acids) but is variable in the carboxyl terminal. The structural analysis reveals that LigA and LigB are present on the surface of *Leptospira*. Interestingly, LigB contains twelve 90 amino acid sequence repeats whereas LigA consists of thirteen repeats. In addition, LigB contains an agglutinin-like domain (lectin type) from residues 1054-1160, and a possible tyrosine kinase phosphorylation site from residues 1150-1158 (KEALDLSNY; SEQ ID NO:42). The comparison of intimin binding domain of translocated intimin receptor (Tir) (272-304 residues) to LigB using Cn3D, NCBI revealed 25% homology to LigB (1353-1378 residues).

Figure 10:
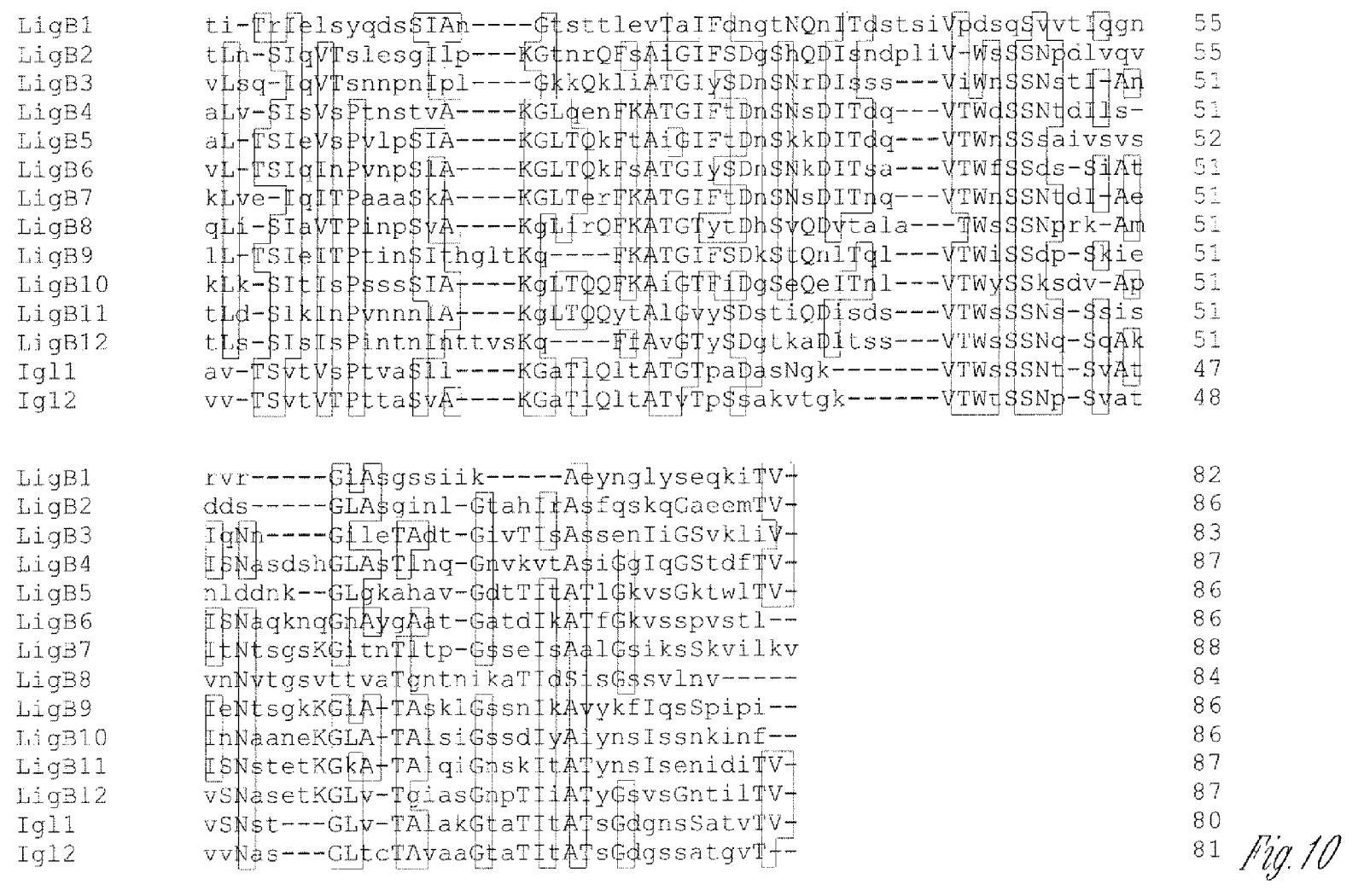

LigA and LigB are similar to intimin with a homology of 24%. Intimin has a Lys motif, two Ig-like domains, D1 and D2 (residues 658-751 & 752-841), and a C-type lectin-like domain D3 (residues 752-841). Similarly, Invasin has four Ig-like domains (D1-D4) and a C-type lectin-like domain (D5) (Bjorkman et al., 1999) whereas LigA and LigB consists of thirteen (D1-13) and twelve repeats (D1-D12) of 90 amino acids motif respectively which have homology to the bacterial domains with Ig-like fold (pfam Big2). Additionally, LigB contained a C-type lectin-like domain, D13 (residues 1014-1165) (FIG. 9). Recently, BipA from *Bordetella bronchiseptica* has been reported to contain 8 tandem repeats of 90 amino acids with a lectin-like carboxyl terminal (Stockbauer, K. E., et al., *Mol. Microbiol.*, 39:67-78 (2001)). The intimin shares 24% homology with LigA and LigB respectively. Twelve repeats of LigB and its homology with bacterial Ig-like domain are depicted in FIG. 10.

Interestingly, LigB is identical in the N-terminal sequences (up to 630 amino acids) with LigA but varies in the carboxyl terminal (FIG. 11). The first 5 tandem repeats (residues 52-133, 137-222, 226-308, 312-398, 402-487 and 491-576) at the N-terminal regions of LigA and LigB are the same. Furthermore, a C-type lectin-like domain, especially the amino acids KEALDLSNY (SEQ ID NO:42; residues 1150-1158) contains tyrosine kinase phosphorylation sites according to the Scanprosite program (SWISSPROT). The alteration in the number of tandem repeats and variation in the carboxyl terminal of LigA and LigB may modify their antigenic determinants to evade the host immune response (Jones, C. J., *West Indian Med. J.* 23:65-68 (1974); Duncan, L. R. et al., *Mol. Biochem. Parasitol.*, 48:11-16 (1991)).

The induction of attachment-effacing lesions by bacteria involves a three-stage model including initial attachment of bacteria to host cells, signal transduction and phosphorylation of host cells, and finally, intimate attachment of bacteria to the host cell membrane. *Yersinia* and *E. coli* mediate internalization into host cells using surface proteins such as invasin and intimin (Isberg, R. R. et al., *Cell*, 50:769-778 (1987); Jerse, A. E. et al., *Proc. Natl. Acad. Sci. U.S.A.*, 87:7839-7843 (1990)). Invasin mediates entry by binding to integrins that activate reorganization of the cytoskeleton (Tran Van Nhieu, G. and Isberg, R. R., *Embo J.*, 12:1887-1895 (1993)). In Enteropathogenic *E. coli* (EPEC), intimin binds to Tir (translocated intimin receptor) produced by this bacterium, which eventually induces cytoskeletal rearrangements (Kenny, B. et al., *Cell*, 91:511-520 (1997)). Although the role of tyrosine phosphorylation in pedestal formation is unclear, Tir is tyrosin phosphorylated in EPEC but not in Enterohemorrhagic *E. coli* (EHEC) (DeVinney, R. et al., *Cell Mol. Life. Sci.*, 55:961-976 (1999)). It has been indicated that synthesis and secretion may be differentially regulated in these pathogens (DeVinney, R. et al., *Cell Mol. Life. Sci.*, 55:961-976 (1999)). These proteins are encoded by the genes in pathogenicity island, also called as locus of enterocyte effacement (LEE) (McDaniel, T. K. et al., *Proc. Natl. Acad. Sci. U.S.A.*, 92:1664-1668 (1995)). LigB also contained a potential tyrosine kinase phosphorylation site but the localization of the gene in the pathogenicity island has not yet been unraveled. NCBI, Cn3D analysis revealed 25% homology to intimin binding region of translocated intimin receptor at the carboxyl terminal (residues 272-304) especially 32 amino acids with C-type lectin like domain of LigB. Since LigB contains an agglutinin-(lectin type) like domain with a possible tyrosine phosphorylation site at the carboxyl terminal and Tir like receptor, it seems that LigB may trigger cellular signaling events in the host cell.

The hydrophobicity of the deduced amino acid sequence and their potential membrane-spanning region was analyzed. Lig A and B are mostly hydrophilic with some hydrophobic regions and they consist of beta sheets with a few alpha helical regions. The predicted transmembrane region of LigB is from 300-319 residues (IIGSVKLIVTPAALVSI) (SEQ ID NO:43). Cysteine reportedly plays an important role in integrin binding and protein folding (Leong, J. M. et al., *J. Biol. Chem.*, 268:20524-20532 (1993)); Frankel, G. et al., *J. Biol. Chem.*, 271:20359-20364 (1996)). Invasin (Cys906 and Cys982) and intimin (Cys860 and Cys937) contain 2 cysteines and mutants lacking cysteine fail to interact with eukaryotic cells. Analysis of amino acids in the carboxyl terminal of Lig A and B revealed two molecules of cysteine in LigA whereas LigB contains eight cysteines. The numbers of serine and threonine residues in LigB are 224 and 147 whereas LigA has 179 and 142. Regardless, they are the most dominant amino acids in both of these proteins. Similar to invasin and intimin, LigB lacks an Arg-Gly-Asp sequence (RGD), which is critical for the interaction of fibronectin Fn-III 10 with integrins (Hynes, R. O., *Cell*, 69:11-25 (1992)). However, Asp911 of invasin is critical for integrin binding (Hamburger, Z. A. et al., *Science*, 286:291-295 (1999)). A WIGL (trp-ile-glu-leu; SEQ ID NO:44) sequence, characteristic for calcium-coordinating residues that are critical for carbohydrate recognition, is not present in intimin, invasin (Hamburger, Z. A. et al., *Science*, 286:291-295 (1999)) and is also missing from LigB.

Example IV

Expression of Leptospiral Immunoglobulin-Like Protein from *Leptospira interrogans* and Evaluation of its Diagnostic Potential in Kinetic Enzyme Linked Immunosorbent Assay Summary The search for vaccine/diagnostic antigens against leptospirosis led to the identification of LigA (Palaniappan et al., *Infect. Immun.*, 70:5924-5930, 2002). Similar to ligA, the ligB gene was obtained by screening a genomic library of *L. interrogans* with convalescent sera. The ligB gene contains an open reading frame of 5,667 bases that encodes 1,889 amino acids. LigB has complete homology with LigA at the amino terminal region, but is variable at the carboxyl terminal. LigB contains twelve, 90 amino acid sequence repeats of an immunoglobulin-like fold and an agglutinin-like domain (lectin type). Structural analysis revealed that LigA and LigB are surface proteins. Lig genes were present in most of the pathogenic serovars of *Leptospira*, but not in the non-pathogenic *L. biflexa*. LigA and LigB expression were not detectable at the translational level, but were detectable at the transcriptional level in in vitro grown leptospires. The conserved region and variable regions of LigA and LigB (Con, VarA and VarB) were cloned and expressed as GST fusion proteins. Kinetics-ELISA (KELA) was performed with GST fusion proteins of Con, VarA and VarB. Ninety-four canine sera positive for leptospirosis by MAT were evaluated in KELA with Con, VarA and VarB. Out of ninety-four, fifty-six MAT positive canine sera were found to be reactive in KELA. The conserved region of LigA and LigB showed stronger reactivity in KELA than variable regions of LigA and LigB. Canine sera with a MAT titer of >1,600 showed reactivity of 76% to Con, 41% to VarA and 35% to VarB respectively in KELA, suggesting the suitability of these antigens for the serological diagnosis of leptospirosis.

Leptospirosis is caused by spirochetes belonging to the genus *Leptospira*, considered the most widespread zoonotic disease in the world (World Health Organization, 1999). Leptospirosis affects both humans and animals (Vinetz, *Curr. Opin. Infect. Dis.*, 14:527-38 (2001)). Infection is mainly contracted by exposure to water, food or soil contaminated with the urine from infected animals (Levett, *Clin. Microbiol.*

Rev., 14:296-326 (2001)). Potential carriers of *Leptospira* include rats, cattle, dogs, horses, and pigs (Goldstein and Charon, 1990). Leptospirosis in dogs is recognized as a risk factor for human leptospirosis (Douglin et al., 1997). Increased rainfall is associated with a rise in the prevalence of leptospirosis in dogs (Ward, *Prev. Vet. Med.,* 56:215-26 (2002)). Infection can lead to pulmonary hemorrhage, renal, hepatic failure and/or multi-organ failure and even death (Levett, *Clin. Microbiol. Rev.,* 14:296-326 (2001)). An infected dog can also act as an asymptomatic carrier and shed infectious organisms in the urine for its entire lifetime (Murray, *Vet. Rec.,* 127:543-7 (1990)). Approximately 250 serovars have been identified. The available leptospiral vaccines, however, elicit only short-term immunity and do not provide cross protection against different serovars.

Diagnosis of leptospirosis is complicated by the high degree of cross-reaction between different serovars of *Leptospira*. Furthermore, the non-pathogenic *L. biflexa* serovar Patoc, considered an environmental contaminant, provides a cross-reactive pattern to rabbit sera from pathogenic serovars of *Leptospira* (Matsuo et al., *Microbiol. Immunol.,* 44:887-90 (2000); Myers, *J. Clin. MicroBiol.,* 3:548-55 (1976); Myers and Coltorti, *J. Clin. Microbiol.,* 8:580-90 (1978)). Currently available diagnostic techniques include the microscopic agglutination test (MAT), which is laborious and not widely available. In addition, ELISA methods have been developed with a number of modifications (da Silva et al., *Am. J. Trop. Med. Hyg.,* 56:650-5 (1997); Gussenhoven et al., *J. Clin. Microbiol.,* 35:92-7 (1997); Hartman et al., *Vet. Immunol. Immunopathol.,* 7:43-51 (1984); Hartman et al., *Vet. Immunol. Immunopathol.,* 7:33-42 (1984); Levett, *Clin. Microbiol. Rev.,* 14:296-326 (2001); Petchclai et al., *Am. J. Trop. Med. Hyg.,* 45:672-5 (1991); Ribeiro et al., *J. Trop. Med. Hyg.,* 98:452-6 (1995)), but most of them depend on the whole cell proteins of *Leptospira*. Recombinant antigens such as LipL32, flagellin and heat shock protein of *Leptospira* have also been recently developed for diagnosis (Flannery et al., *J. Clin. Microbiol,* 39:3303-10 (2001); Park et al., *DNA Cell Biol.,* 18:903-10 (1999)), but the specificity and sensitivity of these antigens in vaccinated animals have not been determined. The major drawback with the MAT and ELISA procedures is that they cannot differentiate between infected and vaccinated animals. Identification of leptospiral antigens expressed only during infection could be used for the development of new diagnostic reagents that differentiate between vaccinated and infected animals.

In order to identify antigens that are expressed during leptospiral infection, a genomic library of *L. interrogans* was screened with sera from infected animals. Several positive clones were obtained. One clone encoded a gene for a leptospiral immunoglobulin like proteins, referred to as LigA, that is only expressed in vivo (Palaniappan et al., *Infect. Immun.,* 70:5924-30 (2002)).

The present application discloses the identification of another leptospiral immunoglobulin-like protein, named LigB. LigB is identical to LigA at the amino terminus, but is variable at the carboxyl terminus. Truncated forms of the conserved region (Con) and variable regions of LigA (VarA) and LigB (VarB) were expressed as GST fusion proteins in *E. coli*. These recombinant antigens were used in a computer controlled kinetics-based enzyme linked immunosorbent assay (KELA) and were evaluated for their diagnostic potential in vaccinated and MAT positive canine sera. Data disclosed herein indicate that these recombinant antigens can serve as diagnostic reagents for the detection of leptospiral infection.

Materials and Methods

Sera. Convalescent sera obtained from mares that had recently aborted due to leptospiral infection were used to a screen genomic library of *L. interrogans*. These sera have high titers for *L. interrogans* serovar Pomona as determined by the microscopic agglutination test.

A total of 94 canine sera positive for leptospirosis by MAT (MAT positive canine sera) were collected from 1999 to 2002 from the New York State Animal Health Diagnostic Laboratory at Cornell University, Ithaca, N.Y.

Vaccinated sera were obtained from eight week old puppies that had been vaccinated with commercially available vaccines, such as Grippotyphosa/Pomona (G/P), Canicola/Icteroheamorragiae (C/IC) and Grippotyphosa, Pomona, Canicola and Icterohaemorragiae (GPIC) followed by booster injection three weeks later. Sera were collected before vaccination and on the $5^{th}$ and $9^{th}$ week after vaccination.

Control sera were obtained from dogs naturally infected with *Leishmania donovoni, Borrelia burgdorferi* or *Trypanosoma cruzi* and stored at New York State Diagnostic Laboratory at Cornell University, Ithaca, N.Y. Sera were also collected from specific pathogen free beagles (SPF) and also lyme-vaccinated dogs (Chang et al., *Infect. Immun.,* 63:3543-3549 (1995); Chang et al., *Am. J. Vet. Res.,* 62:1104-1112 (2001)).

Bacterial strains and culture conditions. *L. interrogans* serovar Pomona type kennewicki was isolated from an equine abortion (Wen et al., *Nature,* 422:888-893 (2003)). Leptospires were maintained on PLM-5 medium (Intergen, NJ), at 30° C. To isolate low passage cultures of leptospires, experimentally infected hamster tissues were homogenized and inoculated into PLM-5 medium. High passage cultures were prepared by repeated passage (<15 times) of leptospires in PLM-5 medium. Growth was monitored by dark field microscopy.

DNA sequencing and analysis. The positive clones containing ligB gene (derived from screening a genomic library, as previously described) were subjected to DNA sequencing (Palaniappan et al., *Infect. Immun.,* 70:5924-5930 (2002)). DNA sequencing was done using an ABI model 377 automated nucleic acid sequencer at the Bioresource Center, Cornell University, Ithaca, N.Y. Homology searches were performed with NCBI, Blast (Altschul et al., *Nucleic Acids Res.,* 25:3389-3402 (1997)).

Construction of GST fusion proteins of Lig A and LigB. LigA and LigB were truncated into conserved (Con, the N-terminal 599 amino acids without the signal sequences) and variable regions (VarA and VarB, the C-terminal 595 and 788 amino acids of LigA and LigB, respectively). The regions were amplified using PCR with the following primers ligConF. 5'-"TCCCCCGGGGCTGGCAAAAGA," (SEQ ID NO:47) ligConR. 5'-"CCCTCGAGAATATCCGTATTAGA," (SEQ ID NO:48) VariAF, 5'-"CCCCCGGGCTTACCGTTCC," (SEQ ID NO:49) VariAR, 5'-"CCCTCGAGTGGCTCCGTTTTAAT," (SEQ ID NO:36) VariBF, 5'-"TCCCCCGGGGCTGAAATTACAAAT," (SEQ ID NO:50) VariBR, 5'-"CCGCTCGAGTTGGTTTCCTTTTACGTT" (SEQ ID NO:51). The underline nucleotides indicate the restriction site. PCR was performed using 0.5 units accuprime Taq polymerase (Invitrogen, CA). Other reagents were added as outlined by the manufacturer's instructions (Invitrogen, CA). The reaction mixture was subjected to 35 cycles after an initial denaturation at 94° C. for 5 minutes. Each cycle consisted of 94° C. for 1 minute, 50° C. for 2 minutes and 72° C. for 5 minutes.

PCR products were subcloned using a TOPO TA cloning kit (Invitrogen, Carlsbad, Calif.) into pGEX4T-2 plasmids (Amersham Pharmacia). The recombinant plasmids (pLigCon, pLigVarA, pLigVarB) were then introduced into *E. coli* BL21 (DE3). The resulting transformants were grown at 37°

C. overnight on LB agar plates containing 50 μg/mL ampicillin. The expression of proteins was induced with 1 mM IPTG.

Purification of GST fusion proteins. IPTG induced *E. coli* BL21 (DE3) containing the recombinant plasmids was harvested by centrifugation at 5000 rpm. The cell pellets were washed and suspended in PBS followed by passing through a French pressure cell (American Instrument, Silver Spring, Md.). The lysates were then centrifuged to remove the cell debris, and the supernatants were subjected to affinity chromatography using glutathione-Sepharose 4B columns. (Amersham Pharmacia Biotech, Piscataway, N.J.). The GST fusion proteins were eluted according to the manufacturer's instructions (Amersham Pharmacia Biotech, Piscataway, N.J.).

Generation of Polyclonal Antibodies. Adult New Zealand white rabbits were immunized intramuscularly with 100 μg of GST fusion proteins and an equal amount of Freund's incomplete adjuvant. Rabbits were boosted subcutaneously with the same dosage on the $19^{th}$ and $35^{th}$ day. On day 45, the rabbits were bled, and the sera were collected for analysis.

SDS-PAGE and Immunoblot analysis. The recombinant proteins were subjected to sodium dodecyl sulfate-polyacrylamide gel electrophoresis followed by immunoblot as previously described (Chang et al., *Infect. Immun.*, 63:3343-9 (1995); Chang et al., *Am. J. Vet. Res.*, 62:1104-12 (2001); Chang et al., *DNA Cell Biol.*, 12:351-62 (1993)).

RT-PCR. RNA was isolated from log phase cultures of leptospires using an RNA mini kit (Qiagen Inc.), treated with RNAase free DNAase, and subjected to one step RT-PCR with gene specific primers (variable region of ligA and B). The following primers were used for RT-PCR: VariAF, 5'-GAAAATCGCATCAGTAGAAAAC (SEQ ID NO:52); VariAR, 5'-CCCTCGAGTGGCTCCGTTT TAAT (SEQ ID NO:36), VariBF, 5'-TAAACAAAACGGACACGATAGC (SEQ ID NO:53); VariBR, 5'-CCGCTCGAGTTGGTTTC-CTTTTACGTT (SEQ ID NO:51). The reactions were carried out according to the manufacturer's instructions (Qiagen). A reaction containing all the reagents except for reverse transcriptase was used as a negative control. Genomic DNA was used as a positive control.

Southern blot analysis. Genomic DNA isolated from leptospiral strains was digested with EcoRI and subjected to gel electrophoresis. DNA was transferred to Hybond N+ nitrocellulose membranes (Amersham Pharmacia). The membranes were processed as outlined in the manufacturer's instructions for ECL direct nuclei labeling and detection system (Amersham Pharmacia, NJ). The conserved region of the lig gene was used as the probe for the Southern blot analysis.

Optimization of antigen concentration. Based on MAT titer, canine sera were categorized into high (MAT titer of 12,800 to Pomona, 6,400 to Grippotyphosa), low (MAT titer of 6,400 to Pomona, 3,200 to Grippotyphosa) and negative (SPF, specific pathogen free serum). A checkerboard titration of recombinant antigens (Con, VarA and VarB), primary antibodies (negative, medium and high) and secondary conjugate (anti-dog conjugated with horseradish peroxidase) was performed to determine the optimum conditions.

Kinetic ELISA (KELA). The optimized concentrations of recombinant antigens were diluted in 0.1 M bicarbonate buffer and added to a 96 well microtiter plate (Nunc, Denmark). The plates were rocked for 1 hour and then incubated overnight at 4° C. The plates were washed three times with 0.1M PBS containing 0.05% Tween 20 (PBST). Canine sera (primary antibody) in PBST were diluted to 1:200. 100 μl of diluted serum was added to each well and the plates were incubated for 1 hour at 37° C. in a humid chamber. The plates were washed three times with PBST, and then incubated with 100 μl of a 1:4000 dilution of goat anti-dog IgG conjugated to horseradish peroxidase (Cappel, Durham, N.C.) for 30 minutes at room temperature. The plates were washed again three times with PBST, and 100 μl of TMB (Kirkegaard, Md.) was added to each well. Each plate was read three times in a microplate spectrophotometer (Bio-Tek EL-312, Winoski, Vt.) at 650 nm OD with an interval of 1-minute. The results were calculated by the KELA computer program (Diagnostic Laboratory, College of Veterinary Medicine, Cornell University) and expressed as the slope of the reaction between enzyme and substrate to the amount of antibody bound (Chang et al., *Infect. Immun.*, 63:3543-3549 (1995); Chang et al., *DNA Cell Biol.*, 12:351-362 (1993)).

Statistical analysis. The significance of differences between the recombinant proteins in relation to KELA units was evaluated using the analysis of variance statistical method. The analysis was performed in STATISTIX (Analytical software, Tallahassee, Fla.). The least square difference post-hoc test was used to determine mean KELA value and the significant difference of the recombinant proteins. The correlation between MAT and KELA for the six serovars of *Leptospira* was evaluated using the Pearsons Correlation in STATISTIX. This correlation was assessed for each recombinant protein separately. Descriptive statistics were performed to determine the cut off value for each protein in relation to KELA.

Nucleotide Sequence Accession Number. The Genbank accession number for the nucleotide sequence of ligB is AF534640.

Results

Identification, sequencing and expression of LigB. A leptospiral genomic library was constructed as previously described. The library was screened with convalescent sera obtained from leptospiral-infected mares that had aborted (Palaniappan et al., *Infect. Immun.*, 70:5924-5930 (2002)). Several positive clones were identified, one of which contained an open reading frame (ORF) of 5,667 bp. The deduced protein sequence contained 1,889 amino acids and had an estimated molecular weight of 206 kDa. An N-terminal signal sequence of 31 amino acids was predicted using the signal P program (Nielsen et al., *Protein Eng.*, 10:1-6 (1997), Nielsen et al., *J. Am. Vet. Med. Assoc.*, 199:351-352 (1991)). Three possible start codons for this protein were identified and upstream of the start codon of ligB is a potential ribosome-binding site. The recently released genomic sequences of *L. icterohaemorrahgiae* serovar lai contained LigB but not LigA (Genbank number AA065920), which shows 98% homology with LigB of *L. interrogans* serovar Pomona (Ren et al., *Nature*, 422:888-893 (2003). NCBI Blast search revealed homology with the conserved bacterial immunoglobin-like domain (Pfam Big 2) of intimins from *E. coli* (AF319597, AF301015, AF116899) and cell adhesion domain from *Clostridium acetobutylicum* (NC-003030).

Figure 13A:
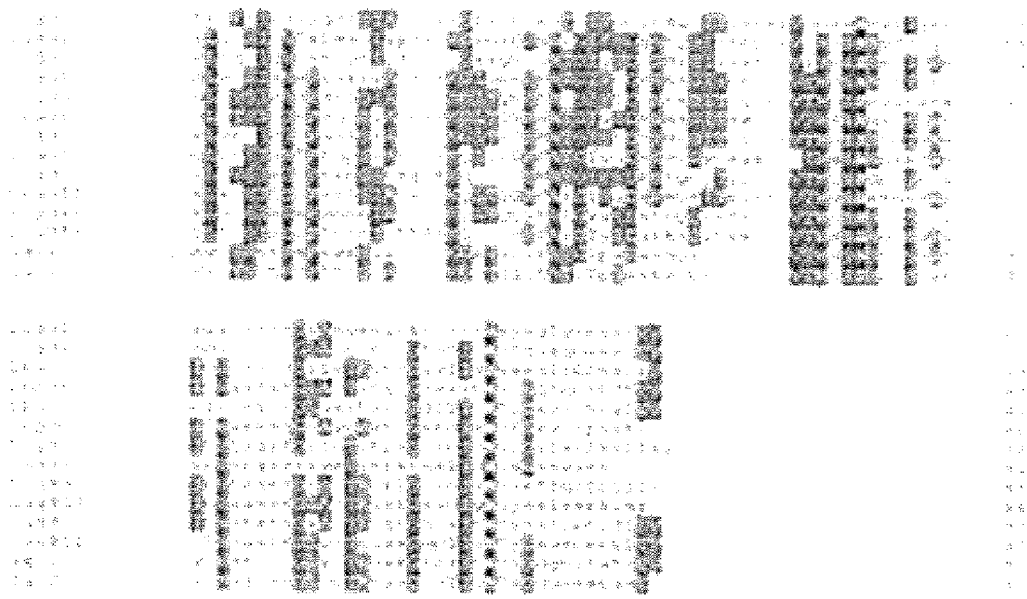
FIG. 13. A. Alignment of twelve repeats of 90 amino acid sequence of LigB indicate homology with the bacterial Ig-like domain from Pfam (Ig1 and Ig2). Gaps have been introduced to optimize alignment among the polypeptides. B. Alignment of variable regions of LigA and LigB.

Primary structure of LigB and comparison with LigA. LigB consists of twelve repeats (D1-D12) of a 90 amino acid motif, which has homology to the bacterial domains with Ig-like fold (pfam Big2) (FIG. 13A). It has been reported that LigA contains twelve repeats of a 90 amino acid motif, but according to pfam, LigA actually has thirteen repeats of the 90 amino acid motif. Additionally, LigB contains a C-type lectin-like domain, D13 (residues 1014-1165).

Figure 13B:
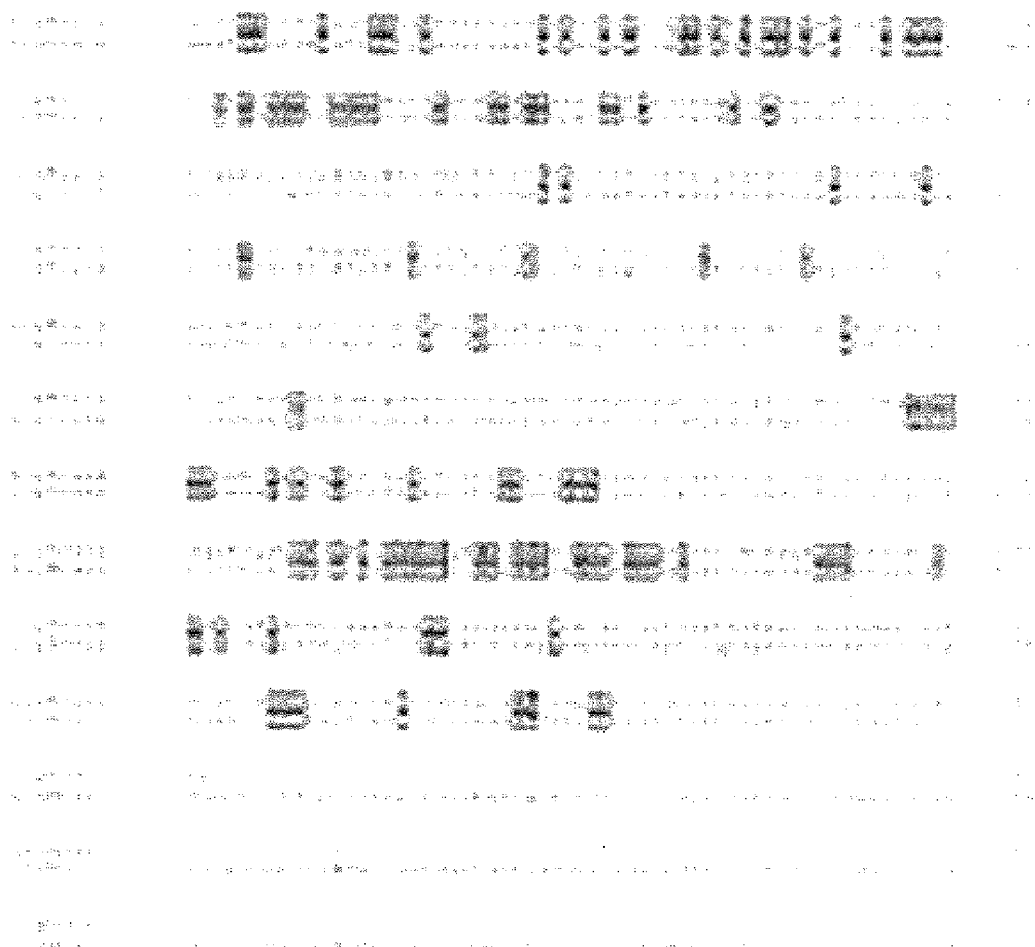

The amino terminal sequence (the first 630 amino acids) of LigB is identical to LigA, but the carboxyl terminus varies (FIG. 13B). The first 5 tandem repeats (residues 52-133, 137-222, 226-308, 312-398, 402-487 and 491-576) at the N-terminal regions of LigA and LigB are identical. Furthermore, a C-type lectin-like domain, especially the amino acids KEALDLSNY (residues 1150-1158), contains tyrosine kinase phosphorylation sites according to the Scanprosite program (SWISSPROT). The numbers of serine and threonine residues in LigB are 224 and 147, whereas LigA has 179 and 142, respectively. Regardless, serine and threonine are the most dominant amino acids in both of these proteins.

Figure 14:
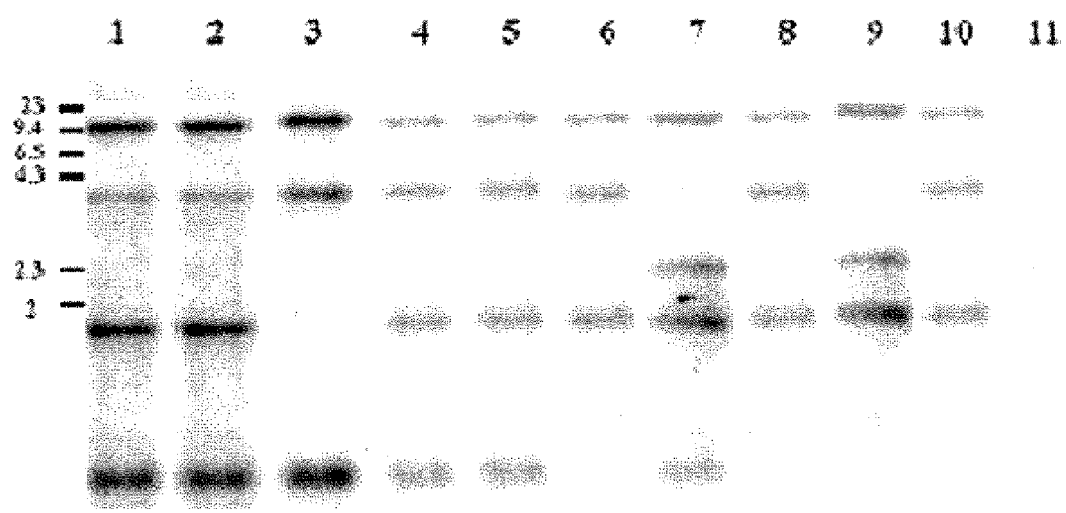
FIG. 14. The presence of lig genes in different serovars of *Leptospira* was determined by Southern blot. The non-radioactively labeled conserved region of LigA and LigB were used to probe EcoRI digested genomic DNA from *Leptospira interrogans* serovars Pomona (Lane 1), Hardjo (Lane 2), Copenhageni (Lane 3), Grippotyphosa (Lane 4), Canicola (Lane 5), Wolffi (Lane 6), Autumnalis (Lane 7), Bataviae (Lane 8), Australis (Lane 9), and Pyrogenes (Lane 10). Non-pathogenic *L. biflexa* serovar Patoc does not contain the lig genes (Lane 11).

The hydrophobicity of the deduced amino acid sequence and the potential membrane-spanning region of LigA and B was analyzed. These two proteins are largely hydrophilic with some hydrophobic patches, and they consist of beta sheets with a few alpha helical regions. The predicted transmembrane region of LigB spans residues 300-319 (IIGSVKLIVT-PAALVSI) (SEQ ID NO:43).

lig genes are widely spread, but only in pathogenic serovars. In order to determine the presence of lig genes in different serovars of *Leptospira*, EcoRI digested genomic DNA from different serovars of *Leptospira* was transferred to nitrocellulose membranes, and probed with a non-radioactively labeled oligonucleotide from the conserved regions of LigA and LigB. Non-pathogenic *L. biflexa* serovar Patoc did not contain lig genes, but the other pathogenic serovars contained copies of lig genes (FIG. 14).

Figure 15A:
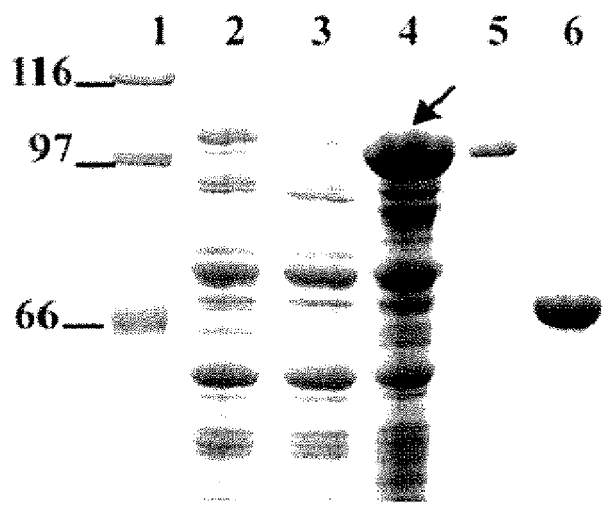
FIG. 15. Expression and purification of GST fusion proteins of LigA and LigB. LigA and LigB were truncated into conserved and variable regions cloned into plasmid pGEX4T-2 and expressed as GST fusion proteins. The fusion proteins were purified by affinity chromatography and subjected to SDS-PAGE. Expression and purification of the conserved regions of LigA and LigB (A); expression of Variable region of LigA (B); expression of Variable region of LigB (C). Lane 1. Molecular Marker (Bio-Rad, CA); lane 2. *E. coli* with vector, pGEX4T-2 only (control); lane 3, un-induced *E. coli* with recombinant construct; lane 4, IPTG induced *E. coli* with recombinant construct; lane 5, Affinity chromatography purified GST fusion proteins; lane 6, Thrombin digested GST fusion protein.
Figure 15B:
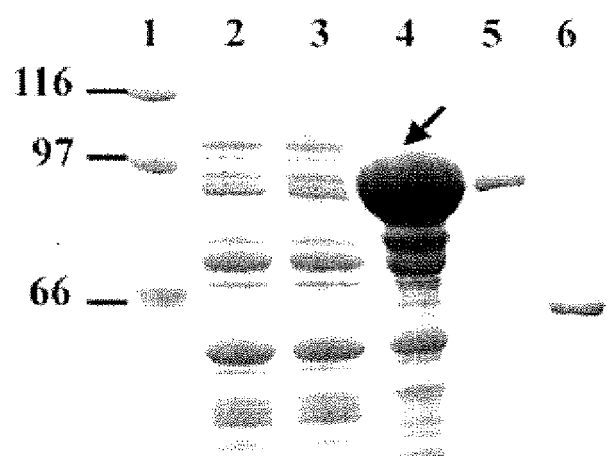
Figure 15C:
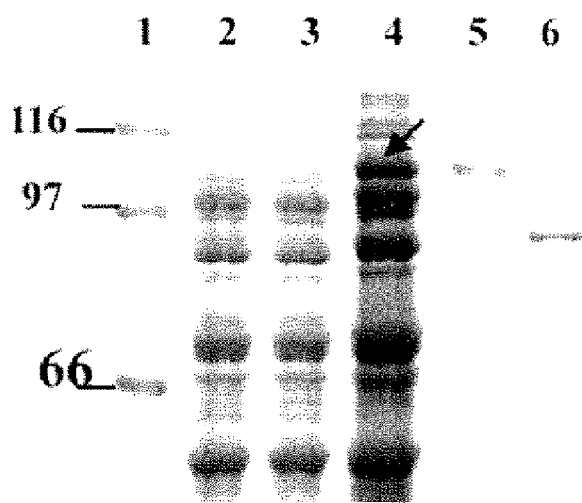

Expression and purification of LigA and B. In order to over express LigA and B, the truncated forms of the conserved and variable regions of LigA and B were cloned and expressed as GST fusion proteins. The expressed recombinant proteins of the conserved and variable regions of LigA and LigB had molecular weights of 92, 93, and 120 kDa, respectively. GST fusion proteins were purified using affinity column chromatography and thrombin cleaved proteins migrated as 62, 63, and 82 kDa, respectively (FIGS. 15A, B and C).

Figure 16A:
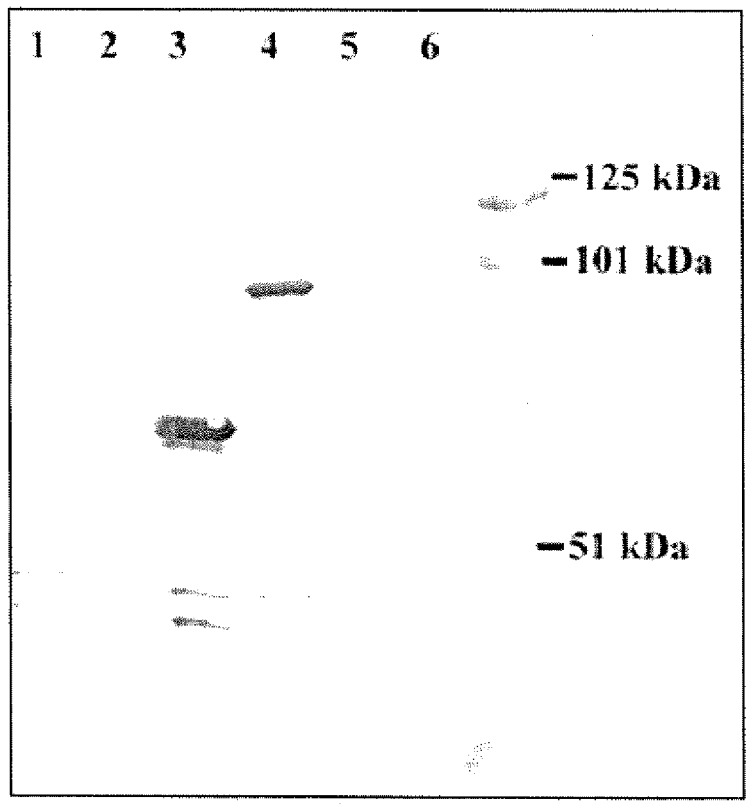
FIG. 16. Immunoblot showing lack of expression of LigA and LigB in leptospires. Whole cell lysates of low passage and high passage cultures of leptospires, purified recombinant GST fusion proteins and thrombin digested GST fusion protein were then subjected to SDS-PAGE and transferred to a nitrocellulose membrane. Membranes were then blotted with a 1:800 dilution of a rabbit antiserum to the variable region of LigA and LigB. 16A and 16B represent the expression of LigA and LigB respectively. Lane 1, *E. coli* with vector; lanes 2 and 4, uninduced and IPTG induced *E. coli* harboring recombinant construct; lane 3, Thrombin digested, purified GST fusion protein; lanes 5 and 6, Low passage and high passage leptospires; lane 7, pre-stained molecular marker (Bio-Rad, CA).
Figure 16B:
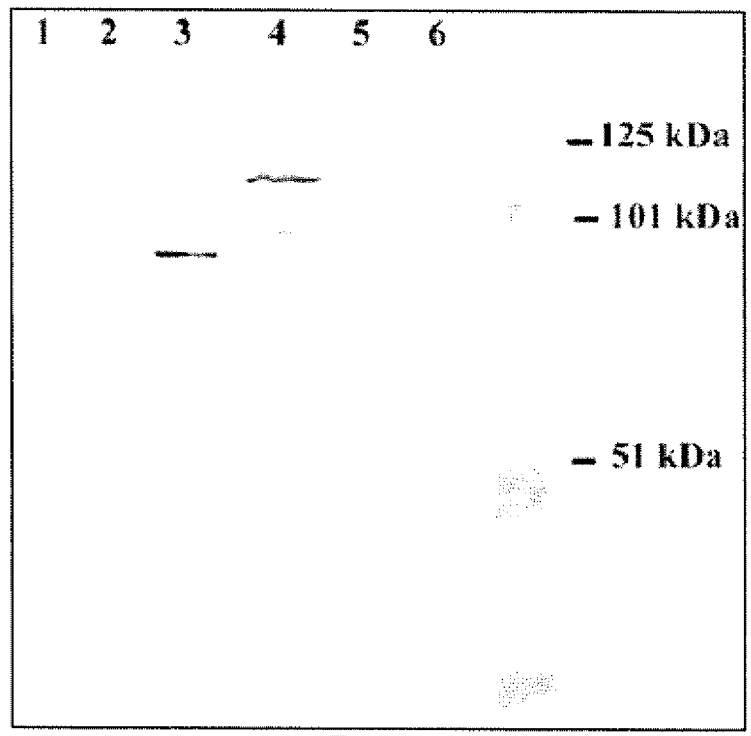

Lack of LigA and LigB expression at the translation level in leptospires. To examine LigA and B expression in leptospires, immunoblots of whole cell proteins of low and high passage cultures of leptospires were probed with polyclonal antibodies to Con, VarA and VarB. LigA and LigB expression was not detectable in leptospires grown in vitro (FIGS. 16A, B and C). In contrast, *E. coli* containing the recombinant plasmids showed strong reactivity. The negative control, *E. coli* without the insert in the vector, showed no reactivity.

Figure 17A:
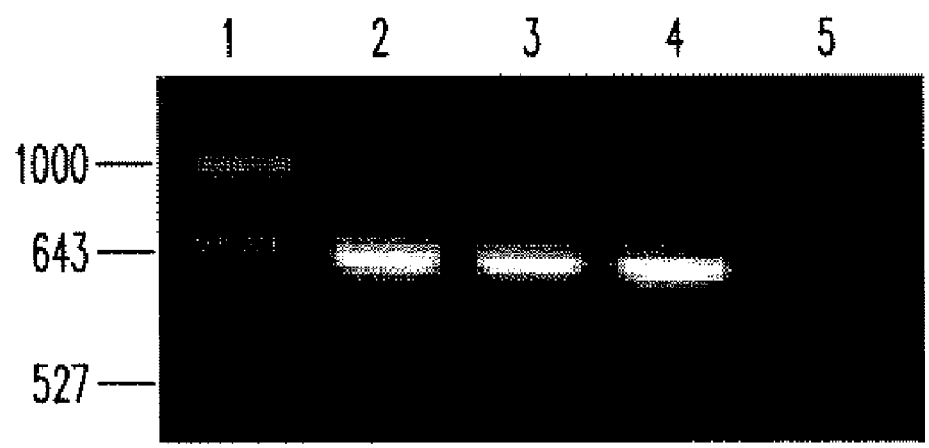
FIGS. 17A and B represent RT-PCR with a ligA and a ligB specific primer, respectively; Lane 1, Marker (pBH20 digested with HinfI); lanes 2 and 3, RNA from Low and high passage cultures; lane 4, genomic DNA from the leptospires (positive control); lane 5, control (RNA without RT in the reaction).
Figure 17B:
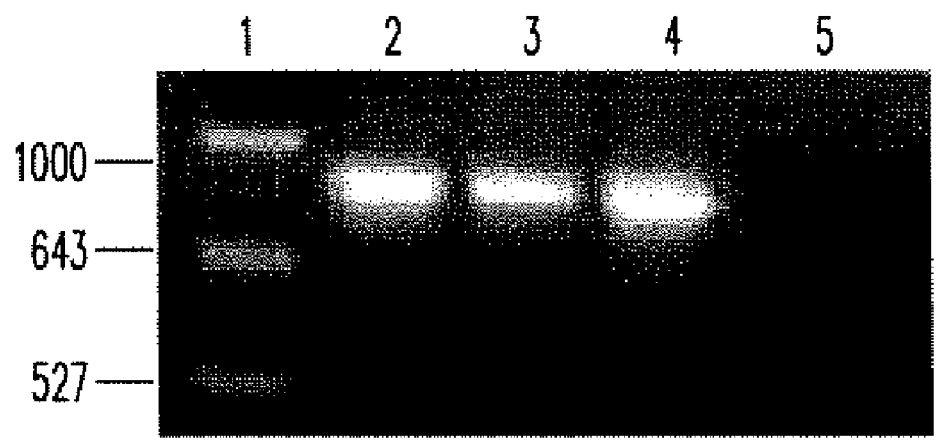
FIG. 17. Expression of LigA and LigB of leptospires at the transcript level. RNA from low and high passage cultures were subjected to one step RT-PCR with ligA and ligB specific primers.

Detection of LigA and B at the transcript level in leptospires grown in vitro. RT-PCR with RNA of low passage and high passage cultures detected the expression of LigA and LigB at the transcript level (FIG. 17). Genomic DNA of leptospires was used as a positive control. The negative control, which lacked reverse transcriptase did not show any amplification. This indicates that LigA and LigB may be poorly expressed under in vitro conditions or the proteins are very unstable.

Optimization of recombinant antigen concentrations. LigA and LigB were truncated into the conserved region of LigA and LigB, variable region of LigA and variable region of LigB and expressed as GST fusion proteins. A checkerboard titration technique was used to determine the optimal concentrations of reagents for ELISA. Based on this, 1 µg of recombinant antigen was chosen and the dilution rate of primary and secondary conjugated antibodies were assessed as 1:200 and 1:4,000, respectively. Since these recombinant antigens were expressed as GST fusion proteins, GST was used as control and the reactivity rate of GST was subtracted for the analysis of samples.

Determination of cut off value: A total of 20 sera collected from unvaccinated/healthy dogs were analyzed in KELA with GST, Con, VarA and VarB. The KELA value for the reactivity of unvaccinated sera to the recombinant antigens was obtained by subtracting the reactivity of GST. The cut off value was determined from the unvaccinated dogs using descriptive statistical analysis (Table 1). All the sera showed negative KELA value in KELA with the recombinant antigens except two sera. The maximum KELA unit of sera from unvaccinated/healthy dogs was considered as the cut off value. The cut off KELA value of Con, VarA and VarB were 7, 42, and 42, respectively.

TABLE 1

Descriptive statistics of KELA value (KELA) to the recombinant antigens in unvaccinated/healthy dogs

| | | Con | VarA | VarB |
|---|---|---|---|---|
| 1 | Lower limit 95% CI | 0 | −1.8578 | 0 |
| 2 | Upper limit 95% CI | 2.0188 | 10.328 | 5.525 |
| 3 | Mean | 0.8235 | 4.2353 | 2.5294 |
| 4 | Standard deviation | 2.3247 | 11.8531 | 8.5855 |
| 5 | Maximum | 7 | 42 | 42 |

Lack of antibodies in the vaccinated sera to recombinant antigens of LigA and LigB. A serial bleed from dogs vaccinated with commercially available vaccines showed MAT titer of less than 400 (Table 2).

TABLE 2

MAT titer value for the sera from vaccinated dogs

| | MAT titer to Pomona for vaccinated sera | | | MAT titer to Grippotyphosa for vaccinated sera | | |
|---|---|---|---|---|---|---|
| Dogs | 5.5 wks | 7 wks | 10 wks | 5.5 wks | 7 wks | 10 wks |
| G/P | — | — | — | — | — | — |
| C/IC | — | — | — | — | — | — |
| GPIC | — | — | — | — | — | — |
| G/P | 200 | 200 | — | — | — | — |
| GPIC | — | — | — | — | — | — |
| G/P | 100 | 400 | — | — | — | 100 |
| C/IC | — | — | — | — | — | — |

G/P represents dogs vaccinated with Grippotyphosa and Pomona vaccine; GPIC denotes dogs vaccinated with Pomona, Grippotyphosa, Icterohaemorrahagiae and Canicola; C/IC represents dogs vaccinated with Canicola and Icterohaemorrahagiae (C/IC)

Figure 18:
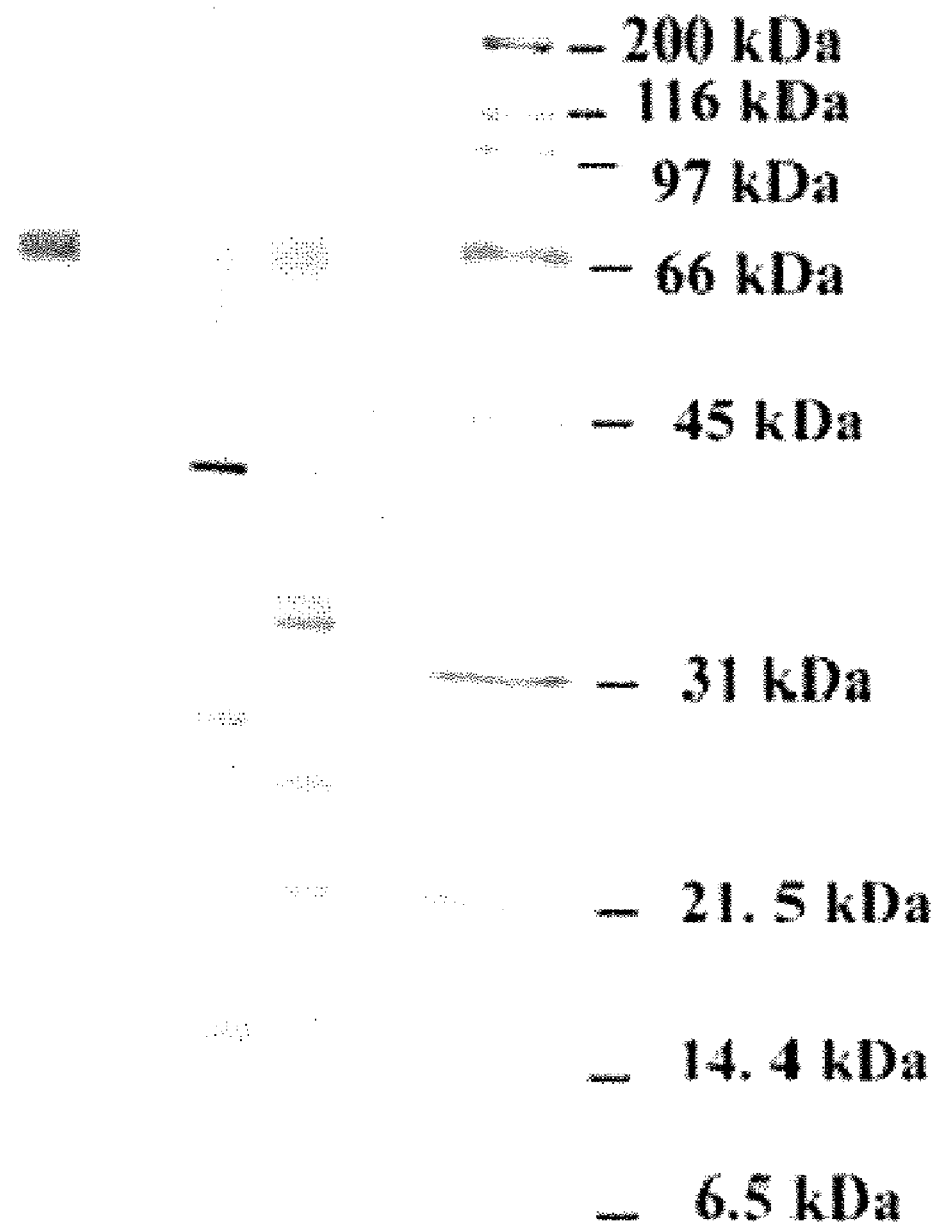
FIG. 18. Reactivity of vaccinated sera to whole cell proteins of leptospires. Whole cell proteins of leptospires were subjected to SDS-PAGE, transferred to nitrocellulose membrane and probed with a 1:10 dilution of pre- and post-vaccinated sera. Lane 1. Pre-vaccinated sera; lane 2. Grippo/pomona Vaccinated sera; lanes 4 and 5. Naturally infected sera from dogs.

Analysis of these vaccinated sera showed no reactivity to recombinant antigens Con, VarA and VarB in KELA but showed reactivity to the whole cell proteins of *Leptospira interrogans* in the western blot analysis (FIG. 18) and in ELISA (our unpublished data). In the western blot analysis with whole cell lysates, most of the vaccinated sera from dogs showed reactivity with leptospiral antigens. For example, Grippo/Pomona combined vaccinated sera reacted with whole cell antigens at 66, 50, and 42 kDa, whereas naturally infected sera from dogs showed reactivity with leptospires antigens at 66, 42, 33, 32, 27 and 21 kDa (FIG. 18). The descriptive statistical analysis of KELA with sera from the vaccinated dogs was below the cut off value (Table 3).

TABLE 3

Descriptive statistics of KELA value (KELA) to the recombinant antigens in vaccinated dogs

| | | Con | VarA | VarB |
|---|---|---|---|---|
| 1 | Lower limit 95% CI | 0.0809 | 0 | 0.1102 |
| 2 | Upper limit 95% CI | 1.5381 | 2.077 | 1.5088 |
| 3 | Mean | 0.8095 | 0.8095 | 0.8095 |
| 4 | Standard deviation | 1.6006 | 2.786 | 2.2441 |
| 5 | Maximum | 6 | 12 | 12 |

Figure 19A:
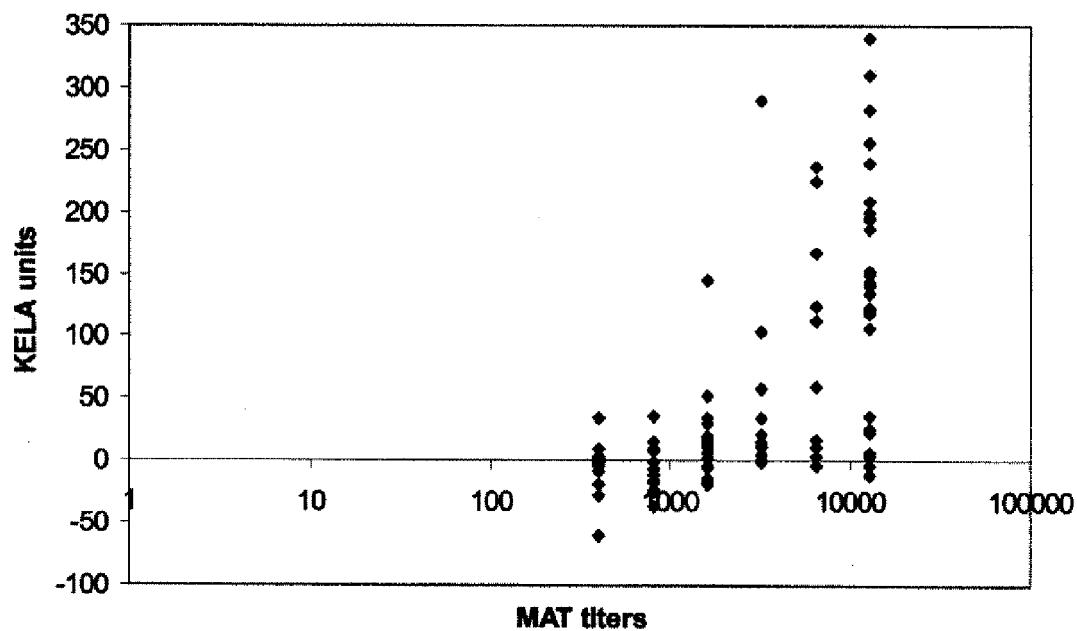
FIGS. 19A, B and C represent the reactivity of KELA using recombinant proteins from conserved regions of LigA and LigB (Con), variable region of LigA (VarA) and variable region of LigB (VarB) to MAT positive canine sera respectively. ◆Represents the reactivity of each sample. Descriptive statistics was used to determine the cut off value for KELA units and the maximum reactivity of sera from healthy dogs was considered as the cut off value (KELA cut off value for Con, VarA and VarB was 7, 42 and 42 respectively).
Figure 19B:
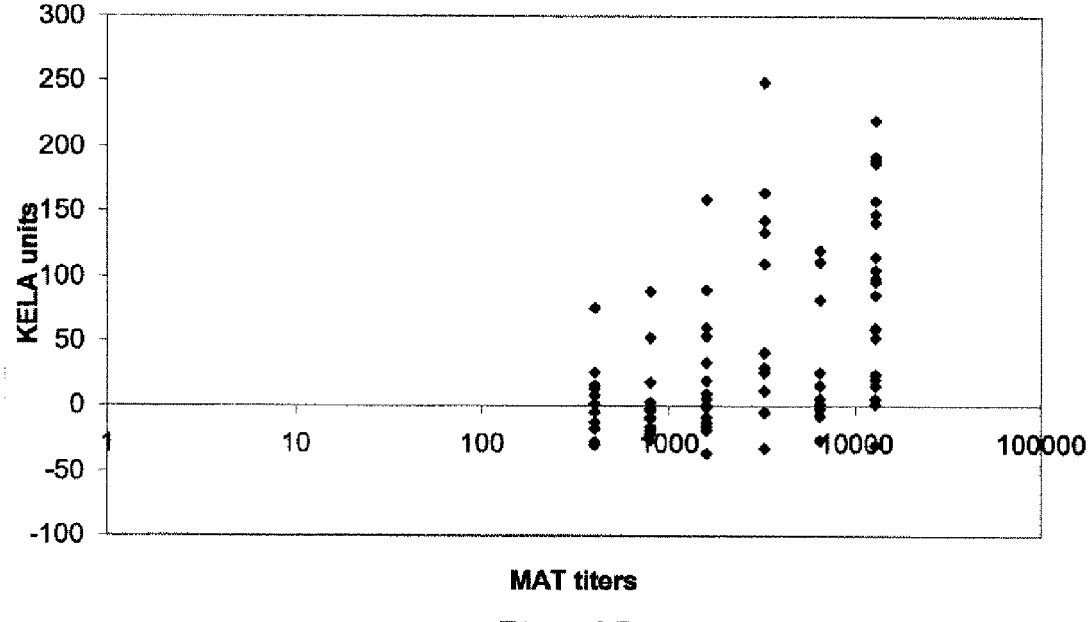
FIG. 19. KELA with recombinant antigens of LigA and LigB to MAT positive canine sera.
Figure 19C:
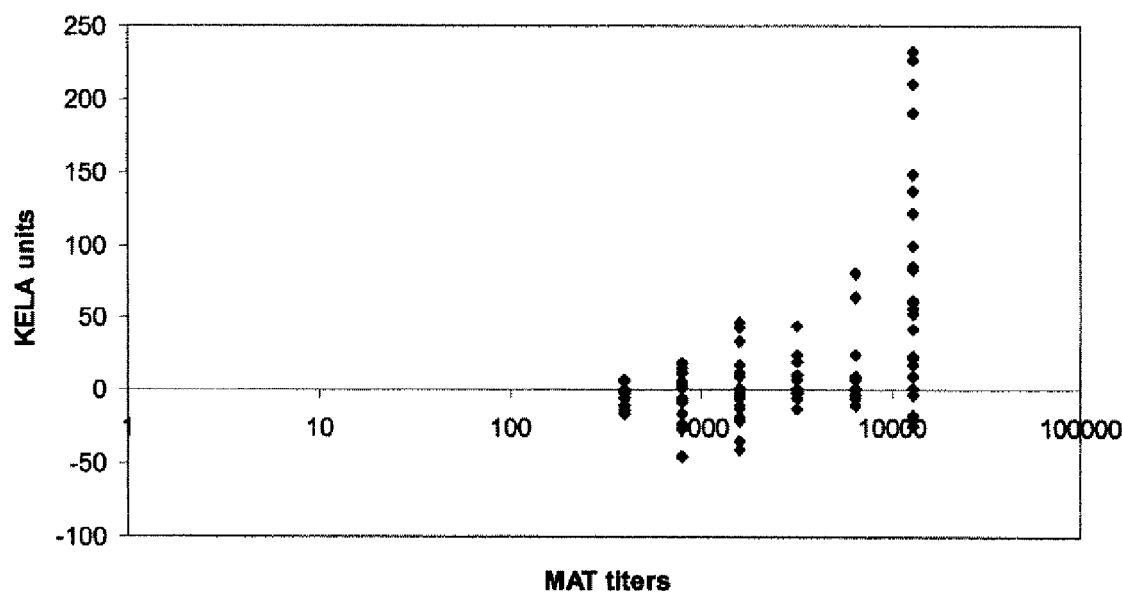

Reactivity of MAT positive canine sera to recombinant antigens in KELA. The diagnostic potential of recombinant antigens of LigA and LigB to detect leptospiral-infected dogs was assessed in KELA using MAT positive canine sera. A total of ninety-four MAT positive canine sera were categorized based on the MAT titer and the reactivity to KELA with recombinant antigens Con, VarA and VarB was established based on the cut off value. FIGS. 19A, B and C represent the reactivity of MAT positive canine sera with recombinant proteins Con, VarA and VarB. The recombinant antigen Con, VarA and VarB in KELA showed reactivity of 76%, 41% and 35%, respectively, to canine sera with MAT titer of more than 1,600, but the overall sensitivity of recombinant antigens Con, VarA and VarB to MAT-positive canine sera was 58%, 30% and 17%, respectively (Table 4).

TABLE 4

Comparison of efficiency of recombinant antigens in KELA to MAT positive canine sera.

| MAT titer | Reactivity of recombinant antigens in KELA | | |
|---|---|---|---|
| | Con | VarA | VarB |
| 12,800 | 88% | 73% | 58% |
| 6,400 | 81% | 27% | 22% |
| 3,200 | 67% | 42% | 8% |
| 1,600 | 67% | 22% | 11% |
| 800 | 28% | 7% | 0 |
| 400 | 15% | 8% | 0 |
| Overall | 58% | 30% | 17% |

The sensitivity of recombinant antigens in KELA was determined from MAT positive canine sera, which did not have a case history for vaccination. Based on the cut off value the percentage of reactivity of recombinant antigens to MAT titer value is represented.

The low titer (below 1,600) MAT-positive canine sera did not show reactivity to the recombinant antigens. Comparing the reactivity of these recombinant antigens with MAT positive canine sera, there are significant differences between Con, VarA and VarB in the KELA units. The mean KELA units for Con and VarA are not significantly different from each other. Post-hoc tests showed that VarB had significantly lower KELA units (19.4) in comparison to Con (53.6) and VarA (41.43). Dogs infected with leishmaniosis, trypanosomosis and borreliosis did not show reactivity to the recombinant antigens suggesting that there is no cross reactivity of these antigens with these agents.

Lack of Correlation between MAT positive and KELA. The correlation between MAT and KELA with recombinant antigens of LigA and LigB was studied but it showed poor correlation (Table 5).

TABLE 5

Correlation between MAT and KELA units in the clinical samples.

| Recombinant proteins | Bratislava | Canicola | Grippotyphosa | Hardjo | Icterohaemorrahgiae | Pomona |
|---|---|---|---|---|---|---|
| Con | 0.0107 | −0.2491 | 0.281 | 0 | 0.525 | 0.2454 |
| VarA | 0.271 | −0.2467 | −0.0348 | 0 | 0.2021 | 0.3273 |
| VarB | 0.2863 | −0.1308 | −0.1741 | 0 | 0.1129 | 0.0125 |

There was poor correlation between MAT and KELA for six serovars of *Leptospira* using pearson correlation in statistix Discussion On first exposure to pathogenic bacteria, a host's immune system generates antibodies directed against cell surface or membrane antigens. Since the antibodies against cells surface antigens may abrogate colonization, recombinant antigens from cell surface or membrane proteins may serve as candidates for the development of novel vaccines and improved diagnostic tests. In this study, LigB was identified by immuno-screening of a genomic library of *L. interrogans* serovar Pomona. Its expression in in vitro grown leptospires was studied. The conserved and variable regions of LigA and LigB were expressed as GST fusion proteins, and a KELA test was developed for the detection of leptospiral infection.

Previously, the lack of expression of LigA in vitro using high passage cultures of leptospires was demonstrated (Palaniappan et al., *Infect. Immun.*, 70:5924-5930 (2002)). Similarly, LigB expression in vitro is not detectable in high and low passage cultures of leptospires. However, both LigA and B are detectable at the transcript level. The lack of detection of LigA and LigB in in vitro grown leptospires suggests that these proteins are either poorly expressed in vitro, or are unstable after expression. Recently, one copy of lig was expressed very weakly in low passage *L. krischneri* RM52 (Matsunaga et al., International Conference on Leptospirosis, Barbados (2002). However, the expression of LigA or LigB at the translational level in low passage strain of *L. interrogans* was not detected herein. The re-establishment of LigA and LigB expression upon infection and the absence of these genes in non-pathogenic leptospires suggests that they are virulence factors of pathogenic leptospires.

The currently available whole cell leptospiral vaccines elicit a short-term immunity. Moreover, they are ineffective in cross protection against different serovars. Thus, vaccinated dogs may contract leptospirosis by the same or different serovars (Brown et al., *J. Am. Vet. Med. Assoc.*, 209:1265-1267 (1996); Cole et al., *J. Am. Vet. Med. Assoc.*, 180:435-437 (1982); Everard et al., *Trop. Geogr. Med.*, 19:126-132 (1987); Harkin and Gargell, *J. Am. Anim. Hosp. Assoc.*, 32:495-501 (1996)). Currently available serological tests are unable to discriminate between vaccine induced leptospiral antibodies and those due to infection. A high MAT titer indicates infection, but a high titer may also be achieved by subsequent vaccination (Goddard et al., *Vet. Microbiol.*, 26:191-201 (1991)). Additionally, MAT is a reliable test for diagnosis, but it is mainly focused on major serovars such as Pomona, Grippotyphosa, Canicola, Icterohaemorragiae and Hardjo. Therefore, there is a need for a diagnostic reagent based on antigens that are expressed only during infection to identify animals that contract leptospirosis despite vaccination. Moreover, the cross-reactivity within various pathogenic serovars in the MAT needs to be validated.

Some of the MAT positive sera having a low MAT titer value of less than 200 to the above-mentioned serovars of *Leptospira* had high KELA values in the KELA assay disclosed herein that uses recombinant antigens of LigA and LigB. Further analyses of these sera for other serovars such as Autmnalis and Bratislava showed high MAT titer value. The KELA disclosed herein having recombinant antigens from the conserved region of LigA and LigB thus can be utilized as a diagnostic tool for leptospirosis.

KELA with recombinant antigens to the conserved regions of LigA and LigB (Con) showed stronger reactivity than VarA and VarB to MAT positive canine sera (Table 4). The overall sensitivity of the recombinant antigens Con, VarA and VarB to MAT positive canine sera was 58%, 33% and 17%, respectively.

In conclusion, the KELA disclosed herein using recombinant LigA and LigB antigen is specific for the serodiagnosis of leptospiral infection. The lack of antibodies to the recombinant LigA and LigB antigens in vaccinated sera suggests that these antigens can be used to identify natural infection of leptospirosis despite vaccination.

Example V

Use of LigA Protein as a Vaccine Candidate Against Infection by *L. interrogans* Serovar Pomona The cloning of LigA protein of *Leptospira interrogans* was previously reported. The potential use of this protein as a vaccine candidate against infection by *L. interrogans* serovar Pomona was evaluated herein. LigA was truncated into the N-terminal 599 amino acids conserved region (Con, without the signal sequence) and the C-terminal 595 amino acid variable region of LigA (VarA) and expressed in *Escherichia coli* as a fusion protein with glutathione-S-transferase (rCon-GST and rVarA-GST). Eight Golden Syrian hamsters were vaccinated with rCon-GST and rVarA-GST along with adjuvant aluminum hydroxide at 4 and 8 week of age. Sixteen hamsters were used as nonvaccinated controls with GST-adjuvant (8 animals) and adjuvant (8 animals). Three weeks after the last vaccination, all animals were intraperitoneally inoculated with $10^8$ of *L. interrogans* serovar Pomona (NVSL 1427-35-093002). All eight vaccinated hamsters survived after challenge. In contrast, 2 or 3 out of 8 animals died 2 weeks after challenge in the GST-adjuvant and adjuvant control group, respectively. Hamsters in the control groups had kidney lesions and were also culture positive in various tissues, but not the vaccinated ones. RCon-GST/rVar-GST elicited an antibody response to rCon in the hamsters by kinetic enzyme-linked immunosorbent assay. Results from this study show that vaccination with rCon-GST/rVar-GST protected hamsters against infection and disease after challenge with *L. interrogans* serovar Pomona.

All publications, patents and patent applications referred to are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A vaccine comprising an immunogenic amount of a purified polypeptide from *Leptospira*, wherein the polypeptide comprises SEQ ID NO: 2, or comprises SEQ ID NO: 33, or consists of at least 50 or more contiguous amino acids of SEQ ID NO: 2; and wherein the purified polypeptide from *Leptospira* is present in an amount that is effective to immunize a susceptible mammal against *Leptospira* infection in combination with a physiologically acceptable, non-toxic vehicle.

2. The vaccine of claim 1, which further comprises an effective amount of an immunological adjuvant.

3. A method of protecting a susceptible mammal against *Leptospira* infection or colonization comprising administering to the mammal an effective amount of a vaccine comprising an immunogenic amount of *Leptospira* protein LigA, wherein the polypeptide comprises SEQ ID NO: 2, or comprises SEQ ID NO: 33, or consists of at least 50 or more contiguous amino acids of SEQ ID NO: 2; and wherein the amount of LigA is effective to immunize the susceptible mammal against *Leptospira* in combination with a physiologically-acceptable, non-toxic vehicle.

4. The method of claim 3, wherein the mammal is a human, dog, bovine, porcine or horse.

5. The method of claim 3, wherein the vaccine is administered orally, mucosally, or by subcutaneous or intramuscular injection.

6. A composition comprising an amount of an immunologically active protein comprising SEQ ID NO:2, or comprising SEQ ID NO: 33, or consisting of at least 50 or more contiguous amino acids of SEQ ID NO: 2, and a pharmaceutically acceptable carrier, which amount is effective to stimulate the formation of antibodies against *Leptospira interrogans* in a susceptible mammal.

7. A composition comprising an amount of an immunologically active protein comprising SEQ ID NO: 2, or comprising SEQ ID NO: 33, or consisting of at least 50 or more contiguous amino acids of SEQ ID NO: 2, which amount is effective to immunize a susceptible mammal against infection caused by *Leptospira*.

8. The composition of claim 6, wherein the composition is effective as a vaccine or an immune stimulating agent.

9. The composition of claim 7, which further comprises an effective amount of an immune stimulating agent.

10. A method of stimulating the formation of antibodies against *Leptospira*, comprising administering to a mammal a composition comprising an effective amount of an immunologically active protein having SEQ ID NO: 2, or comprising SEQ ID NO: 33, or consisting of at least 50 or more contiguous amino acids of SEQ ID NO: 2.

11. The method of claim 10, wherein the composition further comprises an effective amount of an immune stimulating agent.

12. The method of claim 10, wherein the composition is effective as a vaccine.

13. The method of claim 3, wherein the mammal is a human, dog, bovine, porcine or horse.

14. The method of claim 3, wherein the vaccine is administered orally, mucosally, or by subcutaneous or intramuscular injection.

* * * * *